United States Patent [19]

Kuba et al.

[11] Patent Number: 5,815,626
[45] Date of Patent: Sep. 29, 1998

[54] OPTICAL TRANSMISSION DEVICE, SOLID STATE LASER DEVICE, AND LASER BEAM PROCESSING DEVICE

[75] Inventors: Kazuki Kuba; Akira Ishimori; Koji Yasui, all of Hyogo; Kenji Kumamoto; Kuniaki Iwashiro, both of Aichi, all of Japan

[73] Assignee: Mitsubishi Denki Kabushiki Kaisha, Tokyo, Japan

[21] Appl. No.: 714,304

[22] Filed: Sep. 18, 1996

Related U.S. Application Data

[63] Continuation-in-part of Ser. No. 541,042, Oct. 11, 1995, abandoned.

[30] Foreign Application Priority Data

Oct. 14, 1994 [JP] Japan .................................. 6-249459
Sep. 29, 1995 [JP] Japan .................................. 7-253637

[51] Int. Cl.⁶ .................................................. G02B 6/02
[52] U.S. Cl. .......................... 385/124; 385/123; 385/31; 385/33; 385/38
[58] Field of Search ................................. 385/15, 31, 33, 385/34, 38, 39, 88, 92, 93, 123, 124

[56] References Cited

U.S. PATENT DOCUMENTS

| | | | |
|---|---|---|---|
| 4,314,762 | 2/1982 | Gresko | 385/124 X |
| 4,398,790 | 8/1983 | Righini et al. | 385/33 X |
| 4,681,396 | 7/1987 | Jones | 385/33 X |
| 4,762,385 | 8/1988 | Fuse | 385/38 X |
| 4,799,755 | 1/1989 | Jones | 385/38 X |
| 4,842,360 | 6/1989 | Caro et al. | 385/33 X |
| 4,844,574 | 7/1989 | Chande | 385/33 X |
| 4,887,190 | 12/1989 | Sadamune et al. | 385/33 X |
| 5,207,673 | 5/1993 | Ebling et al. | 385/33 X |
| 5,245,682 | 9/1993 | Ortiz, Jr. | 385/33 |
| 5,254,682 | 10/1993 | Ortiz, Jr. | 385/33 |
| 5,370,643 | 12/1994 | Krivoshlykov et al. | 385/124 X |
| 5,418,882 | 5/1995 | Ortiz, Jr. | 385/124 |
| 5,446,816 | 8/1995 | Shiraishi et al. | 385/33 |
| 5,457,759 | 10/1995 | Kalonji et al. | 385/124 X |
| 5,459,802 | 10/1995 | Kyouya et al. | 385/33 |
| 5,684,642 | 11/1997 | Zumoto et al. | 385/38 X |

FOREIGN PATENT DOCUMENTS

| | | | |
|---|---|---|---|
| WO 93/10474 | 10/1992 | European Pat. Off. | 385/33 X |
| 6250702 | 3/1987 | Japan | 385/33 X |
| 255157 | 11/1990 | Japan | 385/33 X |

OTHER PUBLICATIONS

"Laser Handbook", by Laser Institution; Ohm Corp., issued Dec. 30, 1989.

"On–The–Fly Drilling with a Fiber Delivered Face Pumped Laser Beam", General Electric, ICALEO, 1990, pp. 151–166.

"Optical Fiber Transmission of 2 kW CW YAG Laser and its Practical Application to Welding", SPIE vol. 1277, 1990, pp. 188–197.

*Primary Examiner*—Brian Healy
*Attorney, Agent, or Firm*—Sughrue, Mion, Zinn, Macpeak & Seas, PLLC

[57] ABSTRACT

An optical transmission device has an graded index optical fiber having a diameter $\phi_s$ of a core of the optical fiber, a refraction index $n_0$ at a center of the core, and a difference $\Delta n$ between refraction indexes of the center of the core and a peripheral section of the core; and an optical fiber incident system having a smallest focussed point at or near an incident side plane in said optical fiber through which the laser beam being introduced, and a diameter $\phi_{in}$ Of the laser beam at said incident side plane of said optical fiber having a following relationship: $0.5\phi_s \leq \phi_{in} \leq 2\phi_s$, and $\phi_s=(\phi_c\phi_0\theta(2n_0\Delta n)^{-1/2})^{1/2}$, where a diameter and an opening angle of the laser beam waist are $\phi_0$ and $2\theta$. A solid state laser device has an graded index optical fiber in which the diameter $\phi_{in}$ of the laser beam at the optical fiber side having the following relationship: $0.5\phi_s \leq \phi_{in} \leq 2\phi_s$, and $\phi_s=(\phi_c\phi_0\theta(2n_0\Delta n)^{-1/2})^{1/2}$, where a diameter of the laser beam waist at an output level is $\phi_0$, and an opening angle is $2\theta$ (total angle). and a laser processing device incorporating these optical transmission device and the solid state laser device.

48 Claims, 36 Drawing Sheets

(a) $\phi_{in} \ll \phi_s$ (b) $\phi_{in} \sim \phi_s$ (c) $\phi_{in} \gg \phi_s$

◇ : M² VALUE OF INCIDENT BEAM TO FIBER

O : M² VALUE OF OUTPUT BEAM FROM FIBER

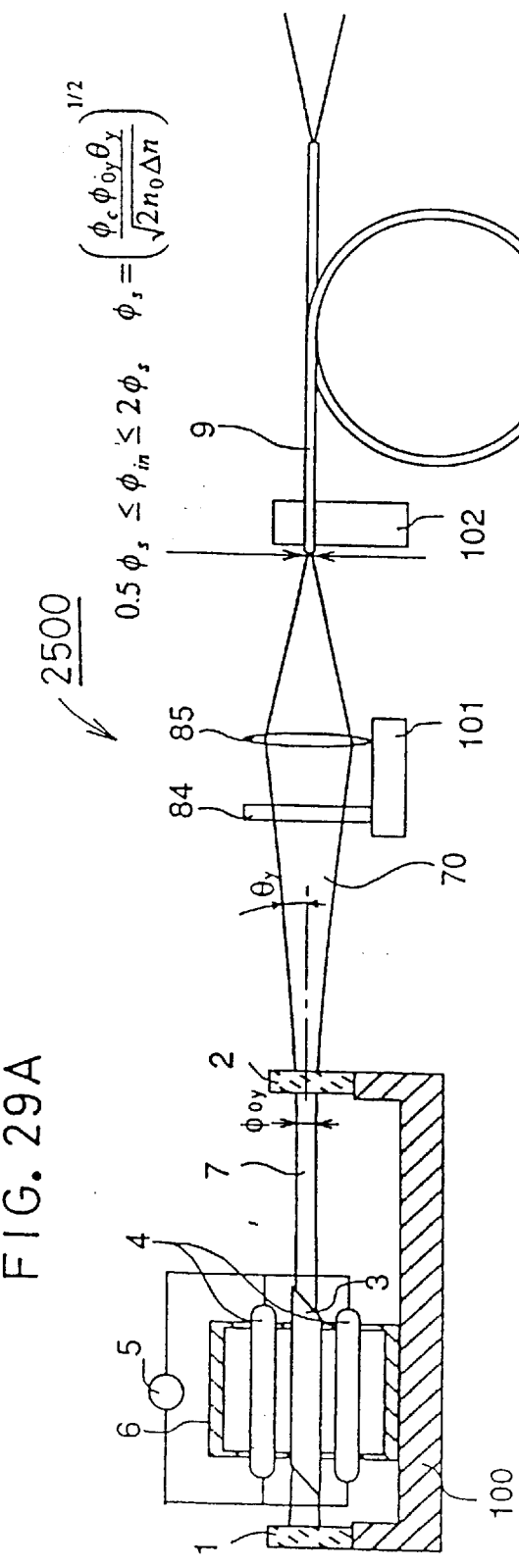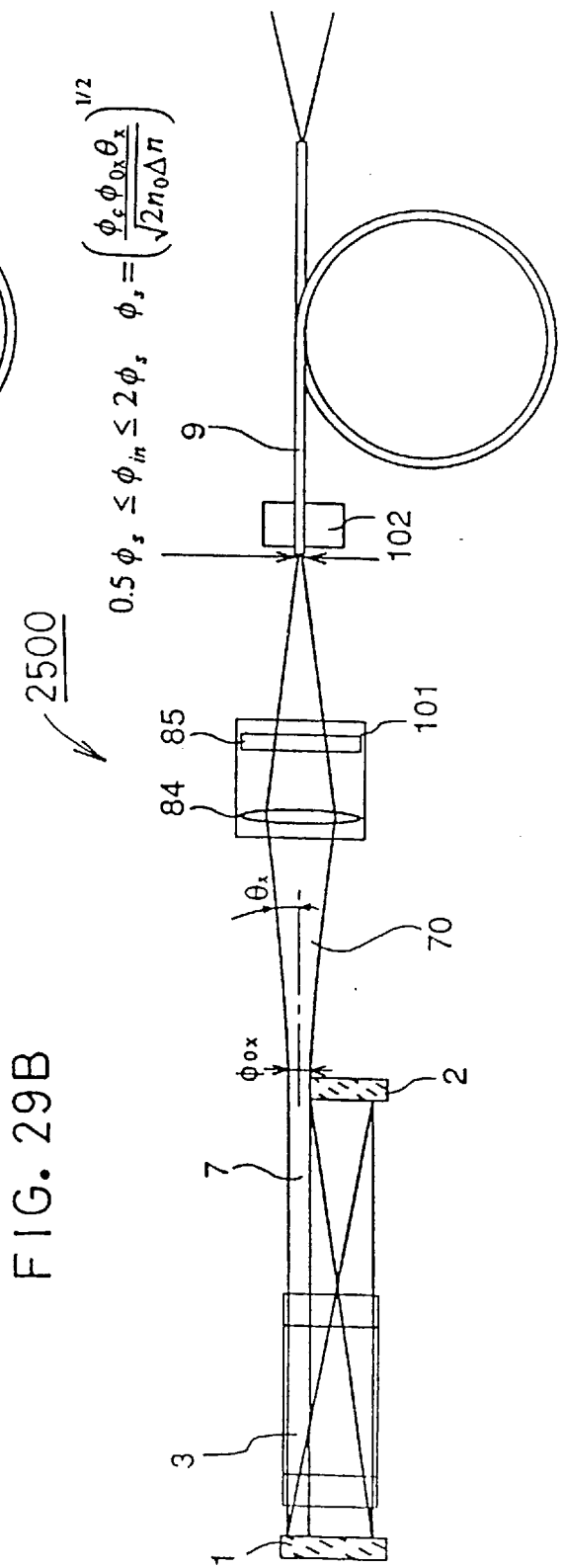

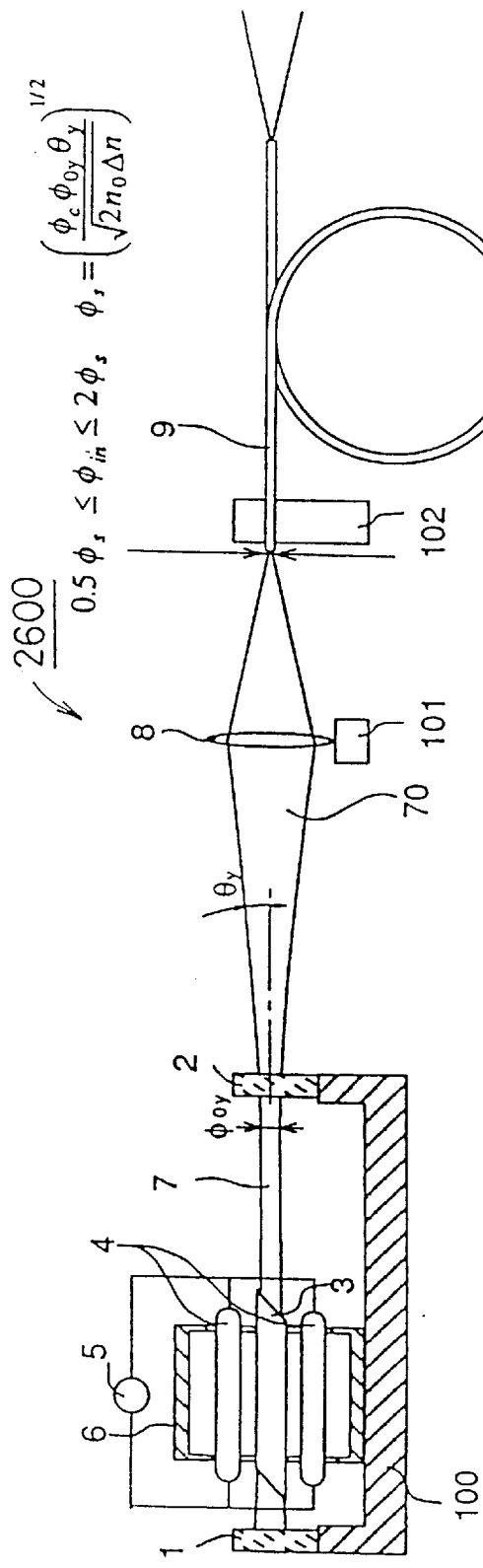
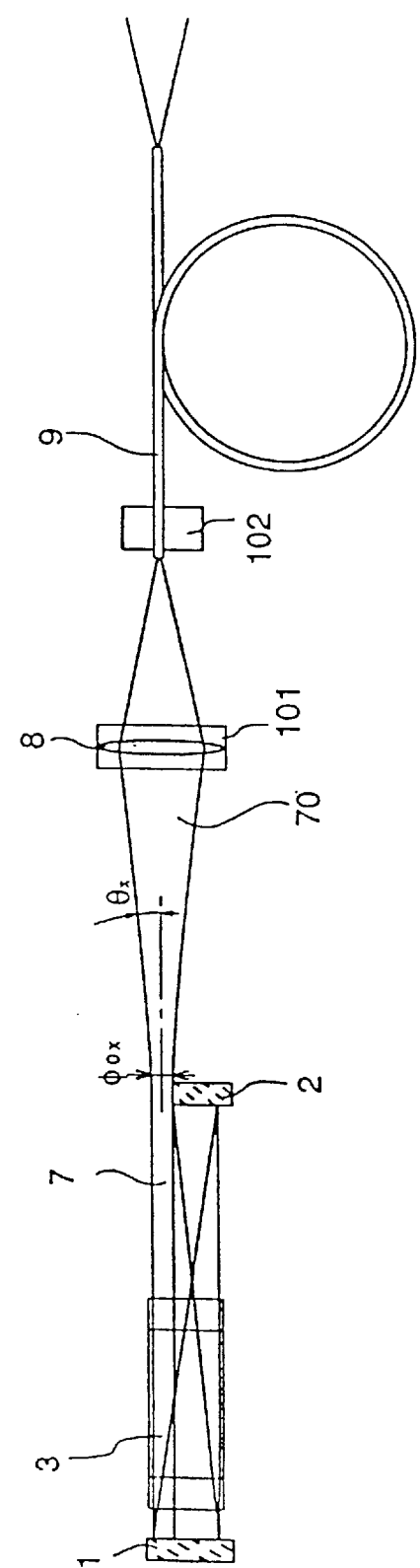
FIG. 30A
FIG. 30B

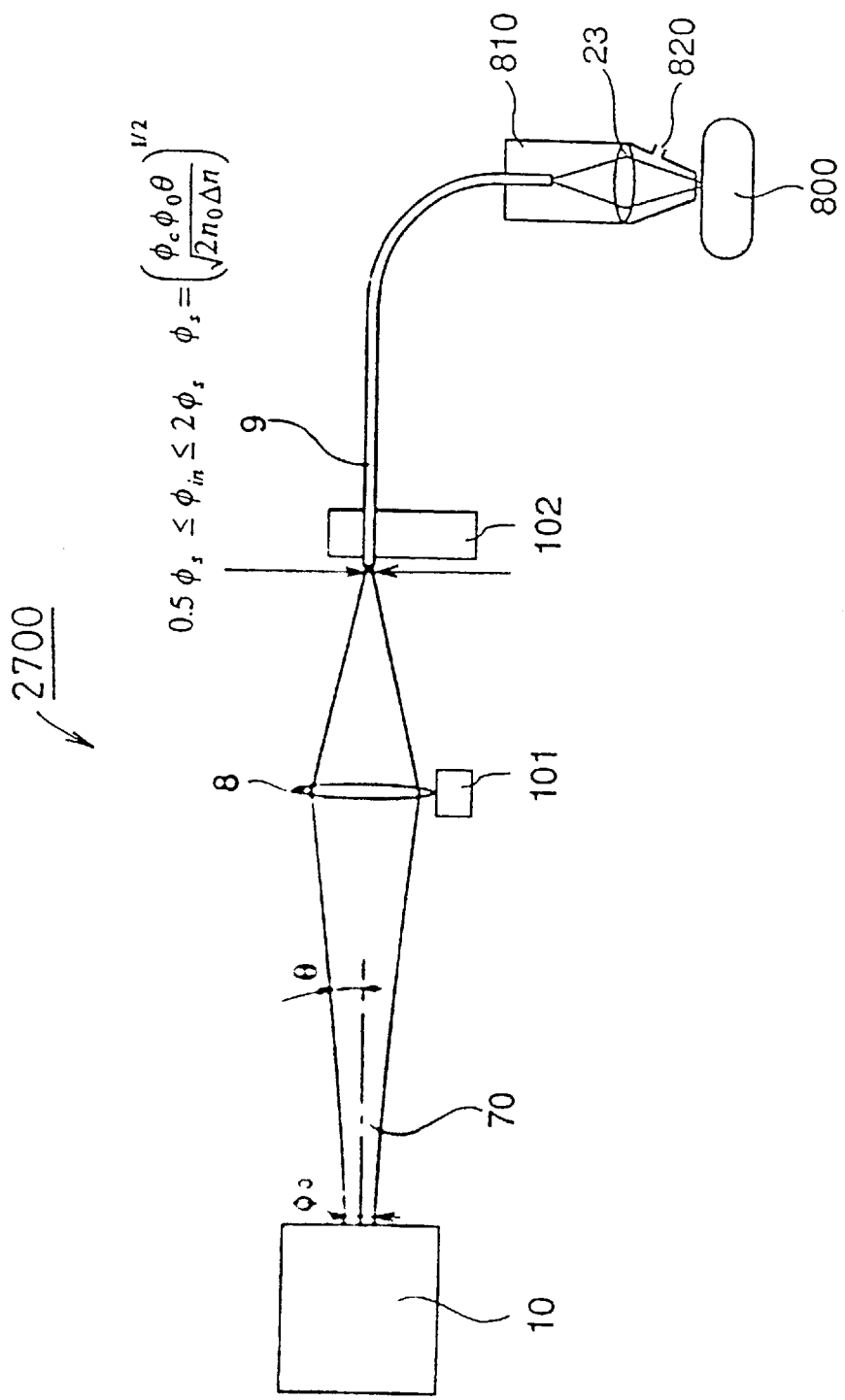

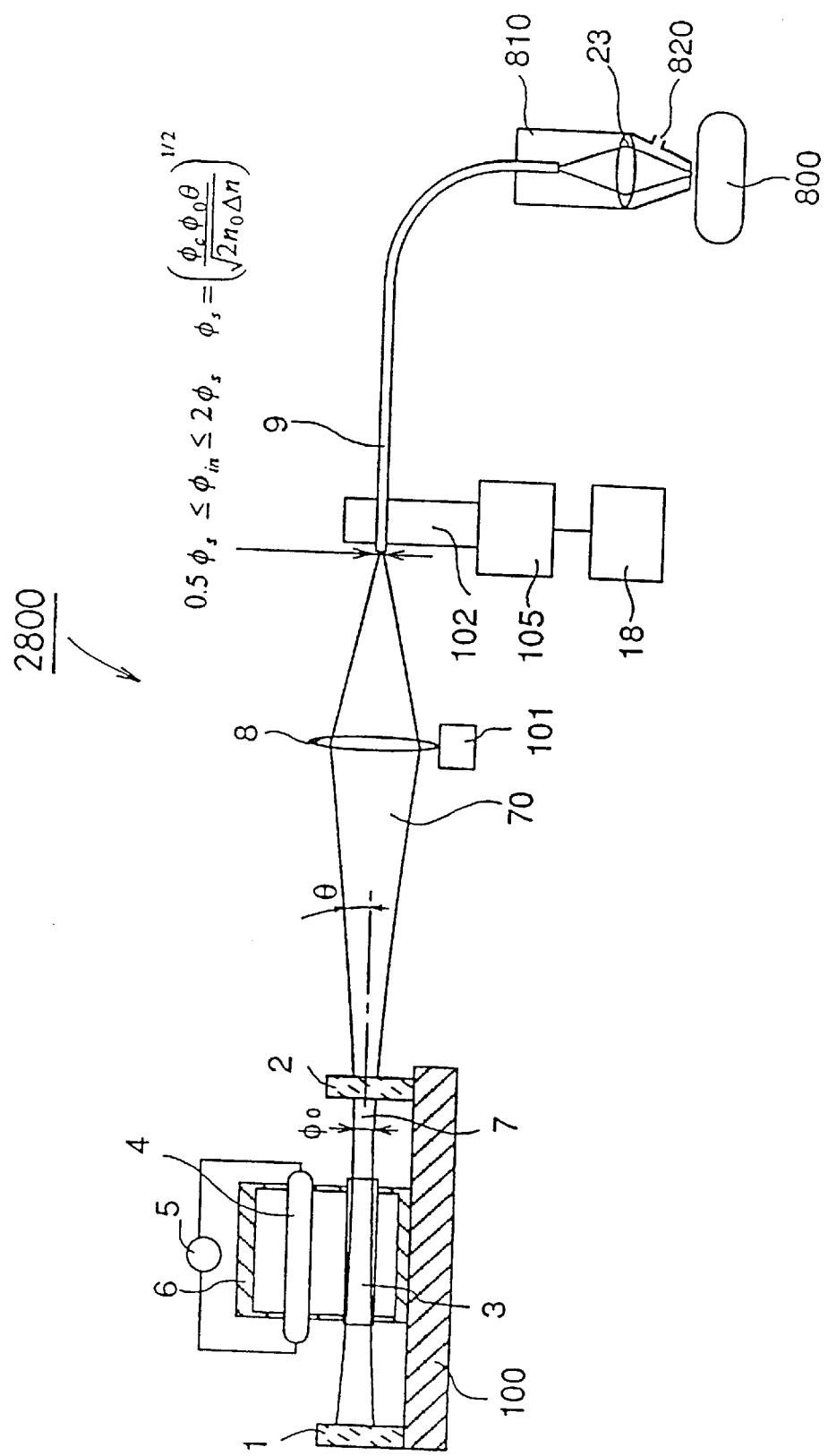

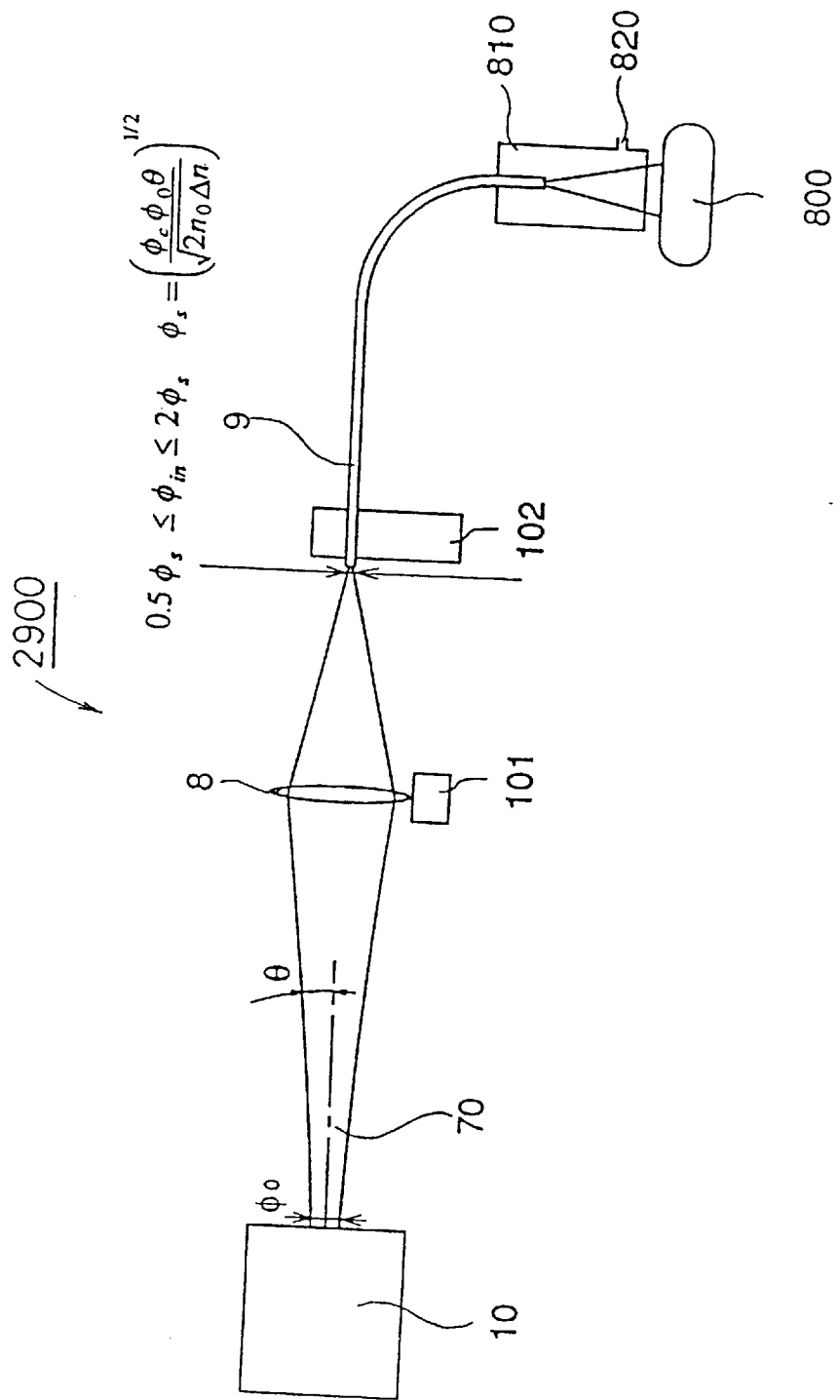

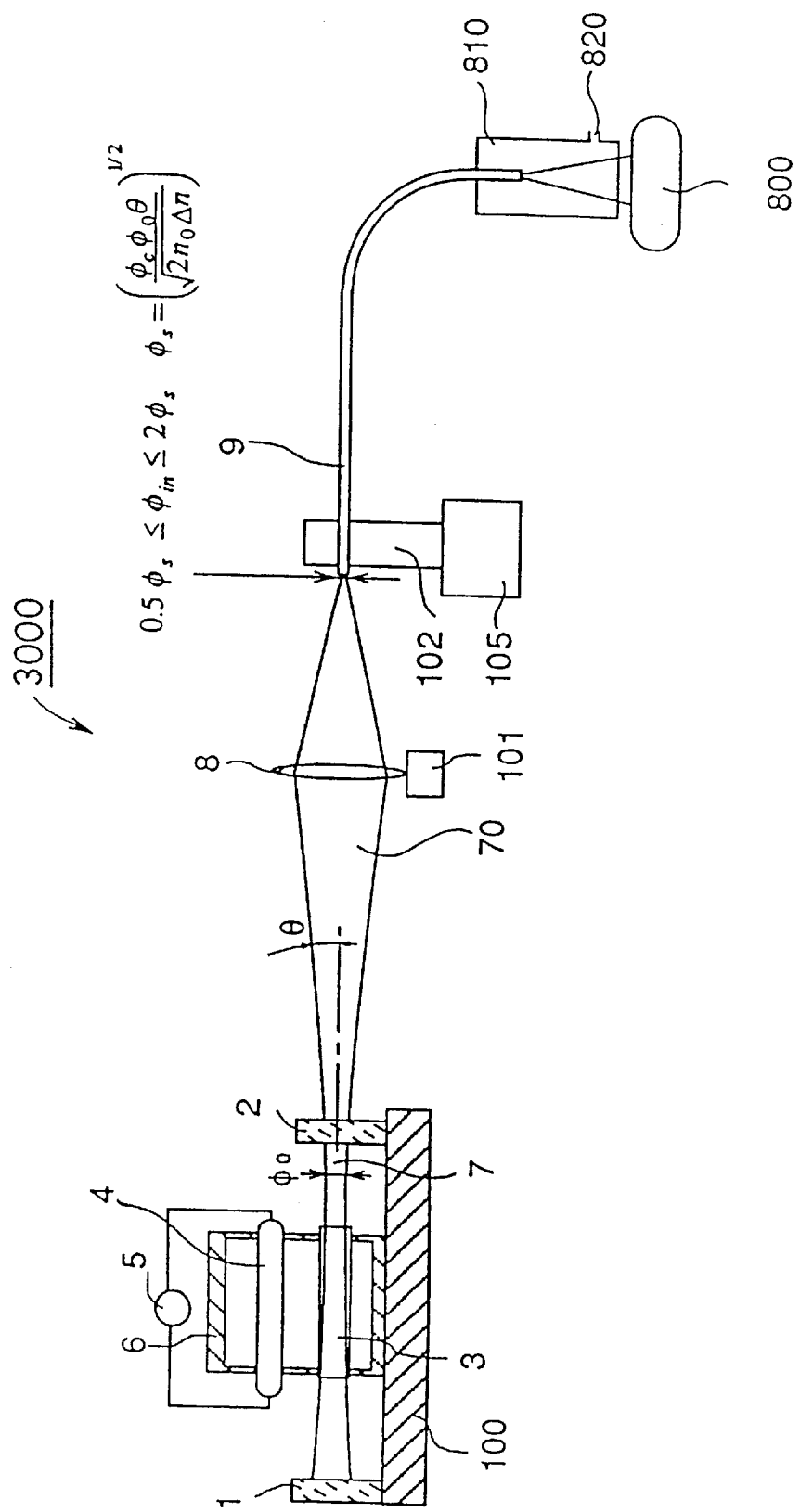

OPTICAL TRANSMISSION DEVICE, SOLID STATE LASER DEVICE, AND LASER BEAM PROCESSING DEVICE

This is a Continuation-in-Part of application Ser. No 08/541,042, filed Oct. 11, 1985 now abandoned.

BACKGROUND OF THE INVENTION

1. Field of the Invention

The present invention relates to an optical transmission device, a solid state laser device, and a laser beam processing device having the optical transmission device or the solid state laser device for transmitting a laser beam with a high focusability used for laser beam processing for industrial processing purposes, medical laser application purpose, and the like.

2. Description of the Prior Art

FIG. 35 is a configuration diagram showing a conventional optical transmission device which has been published in the Japanese publication of the application No. 2-55157, for example.

In the conventional optical transmission device shown in FIG. 35, a reference number 8 designates a focussing lens, a reference number 90 denotes an optical fiber as a waveguide of laser beam, a reference number 10 designates a laser oscillator for generating a laser light or a laser beam, a reference number 70 denotes the laser light or laser beam transmitted from the laser oscillator 10, a reference number 101 designates a lens holder, a reference number 102 denotes an optical fiber holder.

Because the conventional optical transmission device has the configuration described above, the laser light 70 transmitted from the laser oscillator 10 is focused by the focussing lens 8 and transmitted to an incident plane side of the optical fiber 90 and then to the inside of the optical fiber 90. One of or both of the lens holder 101 and the optical fiber holder 102 are mounted on movable stages, respectively. The laser beam 70 can be focused into the incident plane side of the optical fiber 90 by moving or adjusting the position of the movable stage.

In general, in order to transmit the laser beam 70 without losses such as scattering loss, the angle $\theta_{in}$ of incidence to the optical fiber 90 must be $\theta_{in} \sin^{-1}(NA)$, where NA is the inherent value of the optical fiber 90. The inherent value of the optical fiber 90 is expressed as $(n_0^2 - n_1^2)^{1/2}$ when the refractive index of the center of the core of the optical fiber 90 is $n_0$ and the refractive index of a clad in the optical fiber is n1.

On the other hand, when the laser beam 70 is transmitted through the optical fiber 90, the value of the focusability of the laser beam 70 is decreased. For example, dθ is expressed as an index of the focusability of the laser beam when the diameter of the waist of the laser beam is d and an opened angle of the laser beam is 2θ. In this case, the laser beam passed through the lens 8 is scattered in the entire of the core of the optical fiber 90, and the diameter of the laser beam from the output side of the optical fiber 90 becomes approximately the diameter of the core of the optical fiber. Therefore a laser beam having a high focusability can be obtained when the output angle $\theta_{out}$ of the laser beam from the optical fiber is smaller.

We now summarize the index for the focusability of a laser beam. There are many definitions for the diameter of a laser beam. Here, we define the diameter of a laser beam where the energy of the laser beam is 86.5%. In general, the laser beam having the highest focusability is called as Gaussian beam, $TEM_{00}$. The radius (or semidiameter) of the beam waist of the Gaussian beam is $\omega_0$, the opening angle of the Gaussian beam is θ, the following equation (1) is given:

$$\theta_0 = \tan^{-1}\left(\frac{\lambda}{\pi\omega_0 n}\right) \cong \frac{\lambda}{\pi\omega_0 n} \qquad (1)$$

where, λ is a wavelength of the laser beam, n is the refractive index of the laser beam, and $\theta_0$ is adequate smaller than π.

In the air atmosphere, the following equation is given under the condition of n=1:

$$\theta_0 = \lambda/\pi\omega_0 = 2\lambda/\pi\phi_0,$$

where, $\theta_0 = 2\omega_0$ means the diameter of the beam waist.

In addition, it is widely known to use the value $M^2$ to express the focusability of a laser beam. As illustrated in FIG. 36, the value of $M^2$ of the laser beam having the wavelength λ, the diameters $\phi_0$ of the beam waist, the opening angle 2θ of the beam (solid line) is expressed as a rate of the opening angle 2θ of the beam and the opening angle $2\theta_0$ (total angle) of the Gauss beam (dotted line) having the same wavelength, namely $\theta = M^2\theta_0$. Therefore when the Gaussian beam and the laser beam are collimated by the lens 8 having the focus length f and then irradiated to the input side of the optical fiber 90, the beam diameter, or the beam waist diameter at the focussed point of the laser beam 70 becomes $M^2$ times of the Gaussian beam. As apparently by this, a laser beam has higher focusability when the value of $M^2$ becomes smaller. On the other hand, when the opening angle of the laser beam is equal to that of Gaussian beam, the beam waist diameter of the laser beam becomes $M^2$ times of the Gaussian beam. Further, when the opening angle of the laser beam is m times of the beam waist diameter of Gaussian beam, the opening angle of the laser beam becomes M times of that of Gaussian beam. When the equation (1) above is solved by using the $\theta = M^2\theta_0$, we have $M^2 = (\pi\phi_0\theta)/(2\lambda)$. Hence, a laser beam having a smaller opening angle becomes a better focusability beam or a higher brightness beam under the condition that the laser beam has the same diameter of Gaussian beam, and the laser beam having a smaller beam waist diameter becomes a better focusability beam or a higher brightness beam under the condition that the laser beam has the same opening angle of Gaussian beam.

FIG. 37 is a diagram illustrating the relationship between the incident angle θin to the optical fiber 90 and the output angle θout from the optical fiber 90 which is disclosed in the Japanese publication of the application No. 2-55157 like the case shown in FIG.35. This relationship shown in FIG. 37 is used for a step index optical fiber having a unique refractive index. As clearly shown in FIG. 37, when the incident angle is smaller, the output angle becomes also smaller, so that a laser beam having a good focusability can be obtained. However, in this case shown in FIG. 37, there is a lower limit of the output angle θout around 6 to 8 degree. Thereby, the input angle 2θ not more than 8 degree of a lens having a long focal distance is commonly used in the conventional optical transmission device.

As described above, because the conventional optical transmission device has the configuration as shown in FIG. 37, there is a limit of the focusability of a laser beam by the limit of the output angle θout even if a laser beam with a better focusability is used.

In order to increase the focusability of a laser beam, it is possible to use an optical fiber having a smaller core diameter. However, the optical fiber having a smaller core diameter cannot transmit a high power laser beam. In a case of Yttrium Aluminum Garnet (YAG) laser light, it is necessary to use an optical fiber having a core diameter of more than 0.4 mm in order to transmit a laser beam of 500 Watts. Further it is required to use an optical fiber having a core diameter of more than 0.6 mm in order to transmit a laser beam of more than 500 Watts. As shown in FIG. 35, the smallest output angle 2θ out of the laser beam is around 6 degree, the $M^2$ value of the laser beam from the optical fiber having a core diameter of 0.4 mm is around 30 degrees as the smallest value and the $M^2$ value of the laser beam having a core diameter of 0.6 mm is around 46 degrees. Therefore there is a limit of the focusability of a laser beam from the optical fiber even if the laser beam having a higher focusability is transmitted through an optical fiber.

Further, in a prior art, although there is a standard design to obtain an outgoing laser beam having a higher focusability from an optical fiber by using a step index optical fiber, there is no standard design to obtain an outgoing laser beam having a higher focusability from an optical fiber by using a graded index optical fiber. As described in pages 66–67 of "Laser Handbook" (the Laser Society of Japan, 1982, OHMSYA), the graded index optical fiber is equivalent in theory to a state that a plurality of focussing lenses are arranged in no spacing. Although the focusability of an incident laser beam may be kept when ideal focussing lenses are used, there is no report about this. In a common knowledge, the focusability of a laser beam is decreased during the transmission through an optical fiber.

In addition, on pages 66–67 of the Laser Handbook (the Laser Society of Japan, 1982, OHMSYA) described above, there is a description regarding a laser beam of a standard mode of a small output power which is used for optical communication, in other words, there is a description of analysis for a laser beam of $TEM_{00}$ mode. However, there is no description for a high power laser beam used for laser beam processing for industrial processing purposes, and the like. Specifically, because it is common to use a multi-mode oscillation in a solid state laser, it is not known to transmit a multi-mode laser beam through an optical fiber while keeping the focusability of the laser beam.

SUMMARY OF THE INVENTION

An object of the present invention is to solve the drawbacks of such conventional optical transmission devices having the configuration described above.

It is an object of the present invention to provide an optical transmission device capable of keeping a good or high focusability of an incident laser beam by using a graded index optical fiber.

In addition, it is an object of the present invention to provide an optical transmission device capable of keeping a good focusability of an incident laser beam and of adjusting automatically an optical axis of the laser beam at or near an incident side of the optical fiber.

Moreover, it is an object of the present invention to provide an optical transmission device capable of easily controlling a good focusability of an outgoing laser beam from an optical fiber.

Furthermore, it is an object of the present invention to provide a solid state laser device capable of supplying an outgoing laser beam from an optical fiber while keeping a good or highly focusability of the laser beam emitted in the solid state laser device Moreover, it is an object of the present invention to provide a laser processing device capable of performing a laser processing operation while keeping a good focusability of a laser beam or while controlling a focusability of an outgoing laser beam from an optical fiber.

In accordance with one preferred embodiment of the present invention, there is provided an optical transmission device for transmitting a laser beam, comprising: an optical fiber comprising an graded index optical fiber having a diameter $\theta_c$ of a core of said optical fiber, a refraction index $n_0$ at a center of said core of said optical fiber, and a difference $\Delta n$ between refraction indexes of the center of said core of said optical fiber and a peripheral section of said core of said optical fiber; and an optical fiber incident system having a smallest focussed point at an incident side plane in said optical fiber through which the laser beam being introduced into said optical fiber or near said incident side plane of said optical fiber, and a diameter $\theta_{in}$ of the laser beam at said incident side plane of said optical fiber having a following relationship: $0.5\phi_s \leq \phi_{in} \leq 2\phi_s$, and $\phi_s = (\phi_c \phi_0 \theta (2n_0 \Delta n)^{-\frac{1}{2}})^{1/2}$, where a diameter of the laser beam waist of the laser beam is $\phi_0$, and an opening angle of the laser beam is 2θ.

In addition, in the optical transmission device described above, the laser beam is a multi mode laser beam.

Moreover, in the optical transmission device described above, the value $\pi \theta \phi_0 / \lambda$ is not more than 100 when a wavelength of the laser beam is $\lambda$.

Accordingly, the laser beam is focussed at the incident side plane of the optical fiber where the laser beam has the maximum focussed point, and because the laser beam is transmitted through the optical fiber comprising the graded index optical fiber without any change of the focusability of the laser beam, the laser beam may be transferred through the optical fiber without a degradation of the focusability of the laser beam in the optical fiber.

The optical transmission device above, further comprises an aperture which is placed near said incident side plane of said optical fiber, and a diameter of which is smaller than the diameter $\phi_c$ of said core of said optical fiber and greater than said value $\phi_s$.

Accordingly, because the position of the incident laser beam is limited by the aperture so that an effect of a difference from the optical axis may be decreased at the incident side plane of the optical fiber as small as possible, the laser beam may be transmitted without any deterioration of the focusability of the laser beam through the optical fiber.

The optical transmission device above, further comprises an aperture which is placed near an outgoing side plane of said optical fiber through which the laser beam is outgoing, and a diameter of which is smaller than the diameter φc of said core of said optical fiber and greater than said value φs.

Accordingly, a reflection beam at the outgoing side plane of the optical fiber may be prevented by the aperture so that the effect of the reflection beam is decreased as small as possible. In addition, the monitoring of the laser beam may be easily performed and the laser beam may be transmitted without any deterioration of the focusability of the laser beam through the optical fiber.

In the optical transmission device above, said optical fiber incident system further comprises focussing lenses comprising two focussing lenses or a pair of focussing lenses.

Accordingly, the laser beam diameter at the incident side plane of the optical fiber may be easily changed and adjusted based on the feature of the laser beam by adjusting a position of the two focussing lenses or the pair of focussing lenses.

In the optical transmission device above, said lenses placed at or near the incident side plane of said optical fiber comprises a graded index lens, and said graded index lens is placed near said optical fiber or joined to sad optical fiber.

Accordingly, the laser beam diameter at the incident side plane of the optical fiber may be adjusted and changed corresponding to the feature of the laser beam by changing the position of the graded index optical fiber slightly.

In addition, the optical transmission device above, further comprises an aperture which is placed near an incident side plane of said graded index lens.

Accordingly, the aperture placed near the graded index lens prevents to irradiate unnecessary laser beam onto the graded index lens and a peripheral section of the incident side plane of the optical fiber, so that the laser beam may be transmitted without any deterioration of the focusability of the laser beam through the optical fiber.

The optical transmission device above, further comprises an incident laser beam monitor device for measuring a magnitude of an incident laser beam at said incident side plane of said optical fiber and a movable device, on which said optical fiber incident system is mounted, for moving said optical fiber incident system, wherein a position of said optical fiber incident system is adjusted based on output transmitted from said incident beam monitor device.

Accordingly, the position of the focussing lens may be adjusted and changed to a most suitable position by the movable device while the incident laser beam monitor device monitors the position and the diameter of the laser beam at the incident side plane of the optical fiber.

The optical transmission device above, further comprises an outgoing laser beam monitor device for measuring a magnitude of an outgoing laser beam from an outgoing side plane of said optical fiber and a movable device, on which said optical fiber incident system is mounted, for moving said optical fiber incident system, wherein a position of said optical fiber incident system is adjusted based on output transmitted from said incident beam monitor device.

Accordingly, the focusability characteristics of the outgoing laser beam from the optical fiber may be monitored by the outgoing laser beam monitor device, and the position of the focussing lens is adjusted and changed to a most suitable position for the focusability of the outgoing laser beam by the movable device.

In the optical transmission device above, said outgoing laser beam monitor device comprises a power sensor, an aperture is placed near said incident side plane of said optical fiber, and a position of said optical fiber incident system is adjusted so that the output of the laser beam detected by said power sensor becomes the maximum value.

Accordingly, the power sensor monitors the outgoing laser beam from the optical fiber so that the outgoing laser beam has the maximum power by a combination of the power sensor and the aperture placed at the incident side plane of the optical fiber, for example.

In the optical transmission device above, said outgoing laser beam monitor device comprises a photo diode which is placed at a point which is shifted from an optical axis of said outgoing side plane of said optical fiber, and a position of said optical fiber incident system is adjusted so that an output from said photo diode is the maximum value.

Thereby, the position of the focussing lens may be adjusted and changed by using the output from the photo-diode placed at a point which is shifted from the optical axis of the outgoing side plane of the optical fiber so that the output from the photodiode has a minimum value.

In the optical transmission device above, said outgoing laser beam monitor device comprises an aperture which is placed at an outgoing side of said optical fiber and a power sensor for detecting a laser beam which is transmitted through said aperture, and a position of said optical fiber incident system is adjusted so that a power of the laser beam through said aperture becomes the maximum power.

Accordingly, the position of the focussing lens may be adjusted and changed by monitoring the laser beam through the aperture placed at the outgoing side of the optical fiber by using the power sensor so that the output from the power sensor has the maximum value.

In accordance with another preferred embodiment of the present invention, there is provided an optical transmission device comprising an optical fiber incident system comprising: a laser emitting device for emitting a laser beam; an optical fiber incident system comprising: a focussing lens for focussing the laser beam emitted from said laser emitting device, and an optical fiber trough which the laser beam being transmitted, wherein said optical fiber incident system focusses the laser beam concentrated by said focussing lens at an incident side plane of said optical fiber, Characterized in that: said optical fiber comprise a graded index optical fiber; and said optical transmission device further comprises: movable means for moving both of or one of said optical fiber incident system and said optical fiber, wherein a focusability of the laser beam is adjusted by moving both of or one of said optical fiber incident system and said optical fiber by said moving means.

Accordingly, the focusability of the outgoing laser beam from the optical fiber may be changed arbitrary from the focussed point by shifting the position of both or one of the focussing lens and the incident side plane of the optical fiber.

In accordance with another preferred embodiment of the present invention, there is provided a solid state laser device comprising: said optical transmission device as claimed in claim 1; a solid state element for changing into a laser medium when said solid state element being excited by a light from a light source and for emitting a light; a laser resonator for generating a laser beam by using the light generated in said laser medium; an image transfer optical system comprising: a mirror and a focussing lens which being placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

Accordingly, the laser beam having the highly focusability is emitted by the image transfer optical system in the laser resonator and transmitted through the optical fiber while keeping the laser beam of the highly quality.

The solid state laser device above, further comprises an outgoing laser beam monitor device for measuring a magnitude of said outgoing laser beam from said optical fiber, wherein both of or one of said mirror and said focussing lens are moved based on an output from said outgoing laser beam monitor device.

Accordingly, the outgoing laser beam monitor device monitors the outgoing laser beam from the optical fiber, and the position of the image transfer optical system in the laser beam resonant may be adjusted and changed so that the outgoing laser beam has a most highly focusability.

In accordance with another preferred embodiment of the present invention, there is provided a solid state laser device comprising: the optical transmission device described above, a solid state element for changing into a laser medium when said solid state element being excited by a light from a light source and for emitting a light; a laser resonator for generating a laser beam by using the light generated in said laser medium; an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source for exciting the solid state element.

Accordingly, the output from the laser beam resonant may be adjusted by changing the opening diameter of the aperture placed in the laser beam resonant in order to transmit all types of laser beams through the optical fiber while keeping the high quality characteristics.

In accordance with another aspect of the present invention, there is provided a solid state laser device comprising: said optical transmission device described above; a solid state element for changing into a laser medium when said solid state element being excited by a light from a light source and for emitting a light; a laser resonator for generating a laser beam by using the light generated in said laser medium; an aperture placed in said laser resonator; and movable means for moving said aperture toward an optical axis of said laser resonator, wherein a laser power of said laser beam is adjusted by moving a position of said aperture by said movable means while keeping a constant magnitude of the light from said light source for exciting the solid state element.

Accordingly, the output from the laser beam resonant may be controlled by moving the position of the aperture placed in the laser beam resonant in order to transmit all types of laser beams through the optical fiber while keeping the high quality characteristics.

In accordance with another aspect of the present invention, there is provided a solid state laser device comprising: a solid state element for changing into a laser medium when said solid state element being excited by a light from a light source and for emitting a light; a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index n0 at a center of said core of said optical fiber, and a difference $\Delta n$ between refraction indexes of the center of said core of said optical fiber and a peripheral section of said core of said optical fiber; said laser resonator comprises a total internal reflection lens and an output mirror whose curvature are same values, said solid state element is placed near an intermediate point between said total internal reflection mirror and said output mirror, and said total internal reflection mirror is faced to said output mirror as a symmetric resonator, and said solid state laser device further comprises: an optical fiber incident system having a smallest focussed point at an incident side plane in said optical fiber through which the laser beam being introduced into said optical fiber or near said incident side plane of said optical fiber, and a diameter $\phi_{in}$ of the laser beam at said incident side plane of said optical fiber having a following relationship:

$$0.5\phi_s \leq \phi_{in} \leq 2\phi_s,$$

and $$\phi_s = (\phi_c \phi_0 \theta (2n_0 \Delta n)^{-\frac{1}{2}})^{1/2},$$

where a diameter of the laser beam waist of the laser beam at an output level is $\phi_0$, and an opening angle of the laser beam is $2\theta$.

Accordingly, in larger output level of the laser beam having $\phi_0 \theta$, the laser beam is focussed so that the laser beam is irradiated to the smallest focussed point whose diameter has the value: 0.5% at the incident side plane in said optical fiber. Thereby, the laser beam in which the change of the focusability is small may be obtained from the optical fiber even if the output of the laser beam is changed.

In accordance with another aspect of the present invention, there is provided a solid state laser device comprising: a solid state element for changing into a laser medium when said solid state element being excited by a light from a light source and for emitting a light; a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index n0 at a center of said core of said optical fiber, and a difference $\Delta n$ between refraction indexes of the center of said core of said optical fiber and a peripheral section of said core of said optical fiber; the laser beam generated by said solid state resonator has an anisotropic characteristic in which focussing characteristics of the laser beam are different in a first direction (X axis direction) and a second direction (Y axis direction), and said solid state laser device further comprises: an optical fiber incident system has smallest focussed points in the X axis direction and the Y axis direction at an incident side plane in said optical fiber through which the laser beam being introduced into said optical fiber or near said incident side plane of said optical fiber, and diameters $\phi_{inx}$, $\phi_{iny}$ of the laser beam in the X axis direction and the Y axis direction at said incident side plane of said optical fiber has a following relationship:

$$0.5\phi_{sx} \leq \phi_{inx} \leq 2\phi_{sx},$$

$$0.5\phi_{sy} \leq \phi_{iny} \leq 2\phi_{sy},$$

$$\phi_{sx} = (\phi_c \phi_{0x} \theta_x (2n_0 \Delta n)^{-\frac{1}{2}})^{1/2}$$

and $$\phi_{sy} = (\phi_c \phi_{0y} \theta_y (2n_0 \Delta n)^{-\frac{1}{2}})^{1/2}$$

where diameters of the laser beam waist of the laser beam in the X axis direction and the Y axis direction at an output level are $\phi_{0x}$ and $\phi_{0y}$, and opening angles of the laser beam in the X axis direction and the Y axis direction are $2\theta_x$, $2\theta_y$.

Accordingly, the solid state laser device may generate a laser beam having a better focusability and transmit the laser beam through the optical fiber while keeping the focusability of the laser beam even if the solid state laser device has a resonator whose focussing characteristics is different in the X axis direction and the Y axis direction.

In accordance with another aspect of the present invention, there is provided a solid state laser device comprising: a solid state element for changing into a laser medium when said solid state element being excited by a light from a light source and for emitting a light; a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index $n_0$ at a center of said core of said optical fiber, and a difference $\Delta n$ between refraction indexes of the center of said core of said optical fiber and a peripheral section of said core of said optical fiber; the laser beam generated by said solid state resonator has an anisotropic characteristic in which focussing characteristics of the laser beam are different in a first direction (X axis direction) and a second direction (Y axis direction), and said solid state laser device further comprises: an optical fiber incident system has a smallest focussed point at the incident side plane in said optical fiber through which the laser beam being introduced into said optical fiber or near said incident side plane of said optical fiber, and a diameters $\phi_{in}$ having the largest value in $\phi_{0x}\theta_x$ of the X axis direction and $\phi_{0y}\theta_y$ in the Y axis direction at said incident side plane of said optical fiber has a following relationship:

$$0.5\phi_s \leq \phi_{in} \leq 2\phi_s,$$

$$\phi_s = (\phi_c\phi_0\theta(2_{n0}\Delta n)^{-\frac{1}{2}})^{1/2},$$

and $$\phi_0\theta = \max(\phi_{0x}\theta_x, \phi_{0y}\theta_y),$$

where diameters of the laser beam waist of the laser beam in the X axis direction and the Y axis direction at an output level are $\phi_{0x}$ and $\phi_{0y}$, and opening angles of the laser beam in the X axis direction and the Y axis direction are $2\theta_x$, $2\theta_y$.

Accordingly, the solid state laser device having the lens system of a very simple configuration may generates and transmit the laser beam through the optical fiber while keeping the good focusability of the laser beam.

In accordance with another aspect of the present invention, there is provided a laser processing device for processing a target work, comprising: said optical transmission device described above; and a focussing optical system for focussing the laser beam transmitted from said optical transmission device and for irradiating a focussed laser beam to said target work.

Accordingly, it can be performed to process a target work with a high accuracy by focussing the laser beam transmitted through the optical fiber while keeping the focusability of the laser beam onto the target work by the focussing optical system.

In accordance with another aspect of the present invention, there is provided a laser processing device for processing a target work, comprising: said optical transmission device described above, wherein an outgoing laser beam from said optical transmission device is directly irradiated to said target work for processing said target work.

Accordingly, it can be performed to process a relatively wide area in a target work, for example to perform a laser hardening, by directly irradiating the laser beam generated by the solid state laser device and transmitted through the optical fiber while keeping the focusability of the laser beam onto a surface of the target work.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 29A and 29B are configuration diagrams showing a configuration of a solid state laser device of the embodiment 25 according to the present invention.

FIGS. 30A and 30B are configuration diagrams showing a configuration of a solid state laser device of the embodiment 26 according to the present invention.

FIG. 31 is a sectional configuration diagram showing a configuration of a laser processing device as the embodiment 27 according to the present invention.

FIG. 32 is a sectional configuration diagram showing a configuration of a laser processing device as the embodiment 28 according to the present invention.

FIG. 33 is a sectional configuration diagram showing a configuration of a laser processing device as the embodiment 29 according to the present invention.

FIG. 34 is a sectional configuration diagram showing a configuration of a laser processing device as the embodiment 30 according to the present invention.

DESCRIPTION OF THE PREFERRED EMBODIMENTS

Optical transmission devices, solid state devices, and laser processing device according to the present invention will now be described in detail in conduction with exemplary or preferred embodiments by reference to the accompanying drawings.

EMBODIMENT 1

Figure 1:
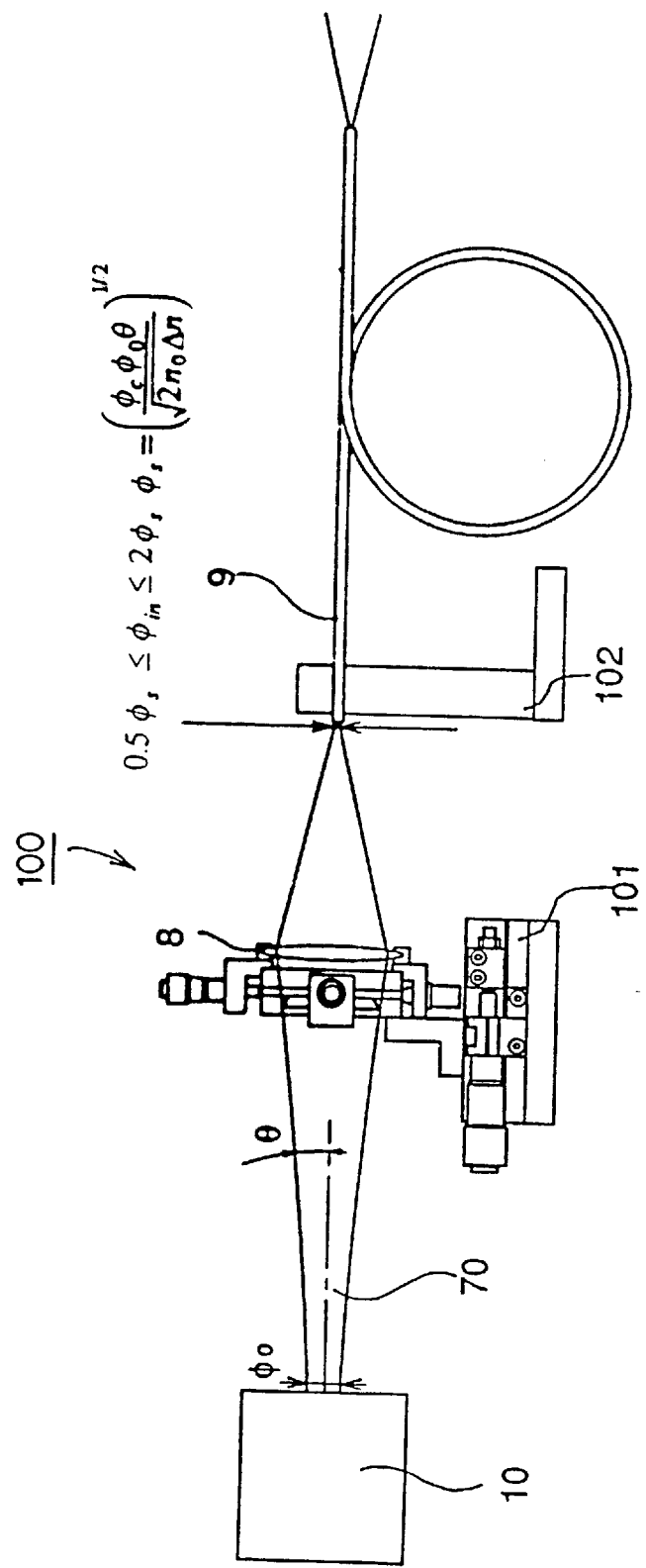
FIG. 1 is a configuration diagram showing a configuration of an optical transmission device as the embodiment 1 according to the present invention.

FIG. 1 is a configuration diagram showing a configuration of an optical transmission device 100 as the embodiment 1 according to the present invention.

Figure 35:
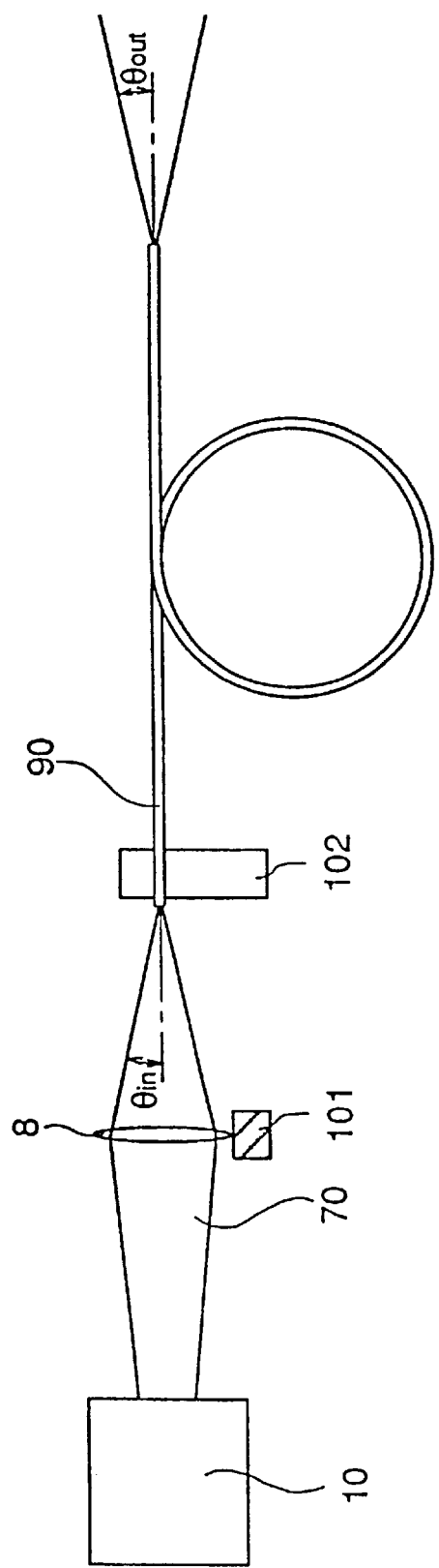
FIG. 35 is a configuration diagram showing a configuration of a conventional optical transmission device.
Figure 36:
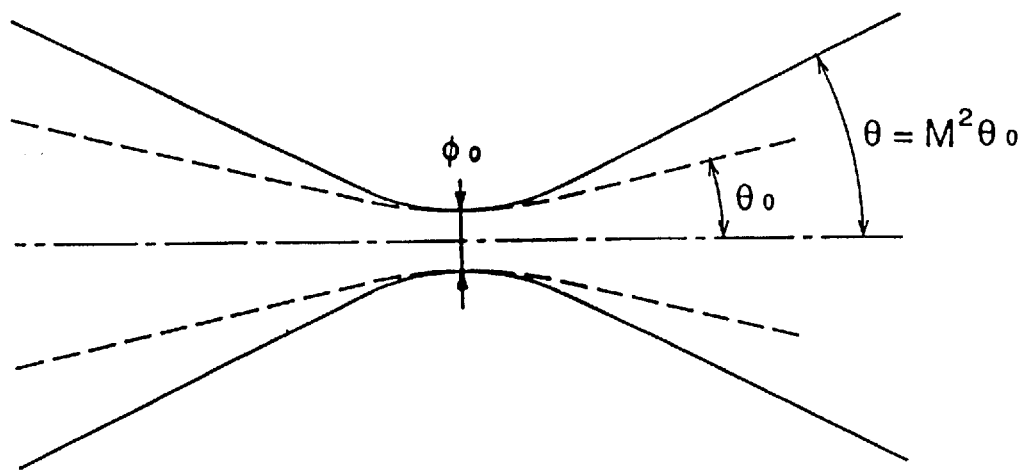
FIG. 36 is an explanately diagram for explaining a focusability index of a laser beam.
Figure 37:
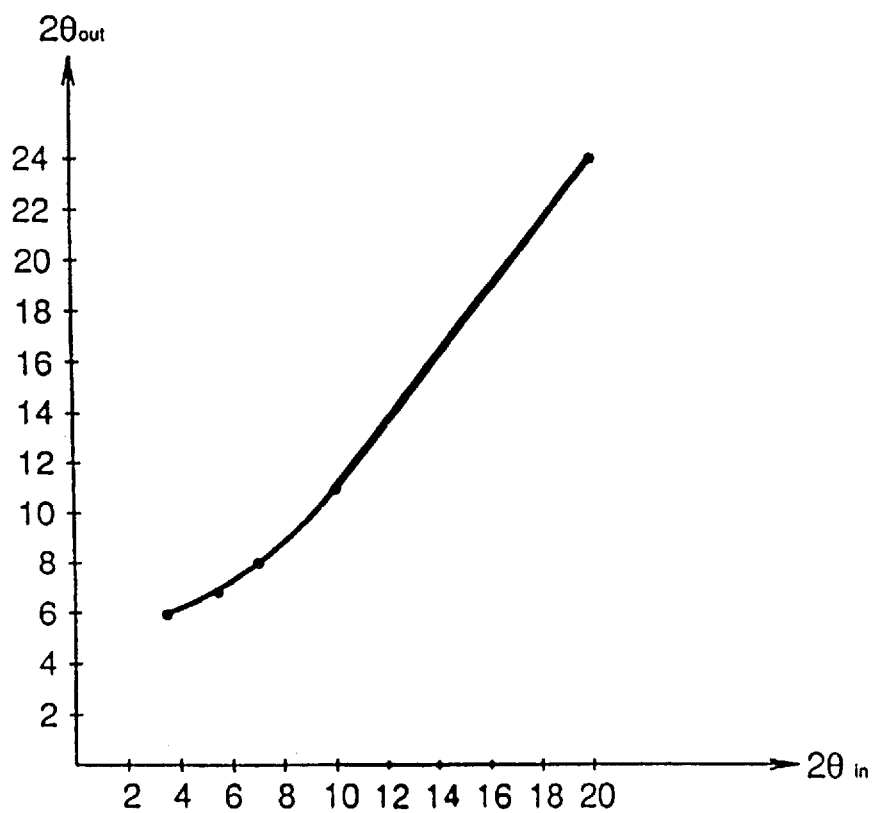
FIG. 37 is an explanately diagram showing the relationship between an incident angle and an outgoing angle of a step index optical fiber.

In the optical transmission device 100 shown in FIG. 1, because the components designated by the reference numbers 8, 10, 70, 101, and 102 are the same components in configuration and function used in the conventional optical transmission device as shown in FIG. 35, so we use the same reference numbers 8, 10, 70, 101, and 102 for these components and omits the explanations therefor.

A reference number 9 designates an graded index optical fiber having a core, the distribution of the refractive index of which has approximately a square form distribution. The focussing lens holder 101 comprises a cross movable stage having a movable stage which may be moved toward an optical axis direction of an optical fiber and a movable stage which may be moved toward a radius direction of the optical fiber by hand operation or manual operation.

As described in the prior art section of this specification, in the conventional transmission device shown in FIG. 35, the incident angle θin of not more than 8 degree of the laser beam is used under the condition where a lens having a long focus length is used as the focussing lens. On the other hand, in the optical transmission device 100 of this embodiment 1, the focus length and the position of the focussing lens 8 is set in order to satisfy the following conditions.

There is the smallest focussed point on the incident side or point nearby the incident side of the optical fiber 9 and the diameter $\phi_{in}$ of the optical fiber 9 is:

$$0.5\phi_s \leq \phi_{in} \leq 2\phi_s,$$

where, $\phi_s = (\phi_c \phi_0 \theta (2 n_0 \Delta n)^{-1/2})^{1/2}$, $\phi_c, \phi_0 \theta$ and $\Delta n$ are a core diameter of the optical fiber 9, a refraction index at the center of the core of the optical fiber 9, the difference of the refraction indexes of the core and the clad of the optical fiber 9, respectively, $\phi_0$, θ are the diameter of the laser beam 70 generated by a laser resonator 10, and the opening angle (a half angle) of the laser beam 70, respectively. In addition, in the optical transmission device 100 of the embodiment 1, there is a beam waist of the laser beam 70 near the output side of the laser oscillator 10 at which the laser beam 70 is emitted.

Next, the operation of the optical transmission device 100 of the embodiment 1 described above will be explained.

The laser beam 70 emitted by the laser oscillator 10 is focussed by the focussing lens 8 whose position is adjusted by the focussing lens holder 101 in order to irradiate the laser beam 70 into the center of the input side plane of the optical fiber 9 by adjusting the position of the focussing lens holder 101.

Figure 2:
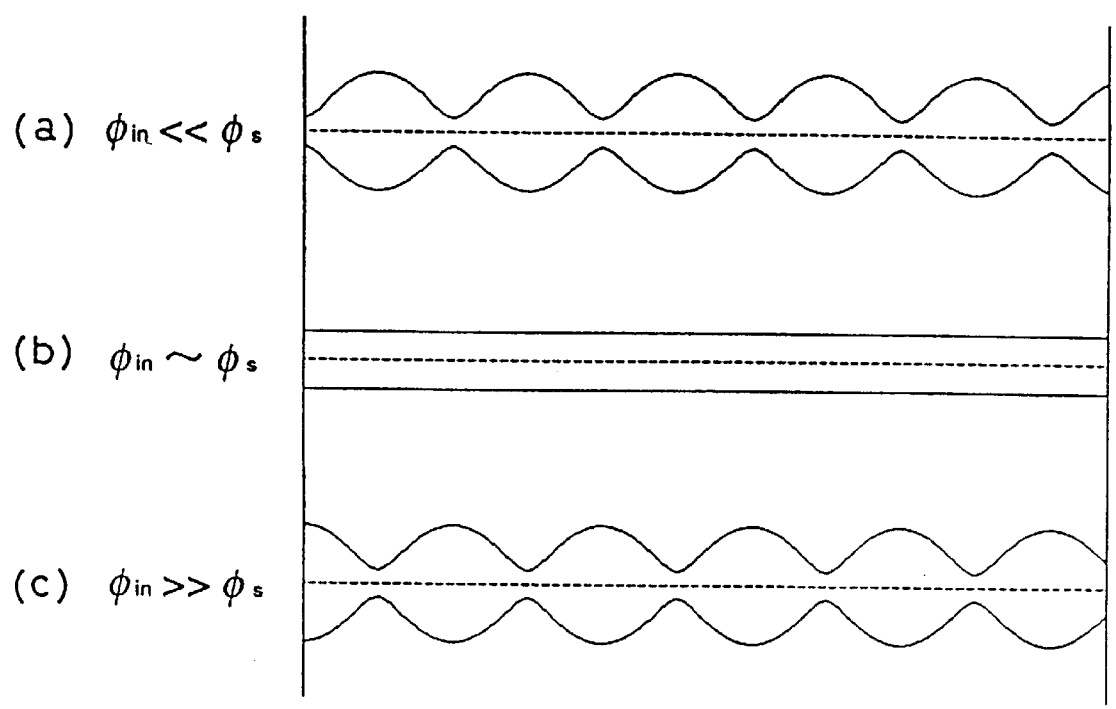
FIG. 2 is an explanately diagram showing propagation states of a laser beam in a graded index optical fiber.

FIG. 2 is a diagram showing the propagation states of the laser beam in the optical fiber 9. Specifically, as shown in FIG. 2, the laser beam 70 is firstly focussed into a smaller diameter rather than an incident diameter at the incident side plane and then passed through the optical fiber 9 while repeating a divergent propagation and a focussed propagation in the optical fiber 9 when the laser beam 70 is focussed by the focussing lens 8 so that the laser beam 70 is irradiated into the incident side plane of the optical fiber at which the laser beam 70 has the smallest focussed point and, as shown in the case (c) in FIG. 2, when the diameter $\phi_{in}$ of the laser beam 70 is greater than the predetermined value$\phi$s, namely, $\phi_{in} >> \phi_s$.

On the other hand, as shown in the case (c) in FIG. 2, the laser beam 70 is firstly diverged in the optical fiber 9 and then transmitted through the optical fiber 9 while repeating the divergent propagation and the focussed propagation in the optical fiber 9 when the diameter $\phi_{in}$ of the laser beam 70 is smaller than the predetermined value$\phi$s, namely, $\phi_{in} << \phi_s$.

In contrast with the propagation shown in the cases (a) and(c) in FIG. 2, the laser beam 70 is passed through the optical fiber 9 without any change of the laser beam diameter of the laser beam 70 when the diameter $\phi_{in}$ of the laser beam 70 is approximately equal to the predetermined value $\phi_s$, specifically $\phi_{in} = \phi_s$, as shown in the case (b) in FIG. 2.

When we consider that the graded index optical fiber is equivalent in theory to a state that a plurality of ideal focussing lenses are arranged without spacing to each other, the focusability of incident laser beam may be kept. However, it is predicted that the focusability of the laser beam 70 is decreased in the optical fiber 9 in the cases (a) and (c) as shown in FIG. 2 because there are an aberration component of the optical fiber 9 as a lens and a dispersion component of the laser beam 70.

In addition, it is required to consider the breakage of the optical fiber 9 when the high power transmission is performed through the optical fiber 9. In this case, there is a problem regarding to the resistance to the high power laser beam transmission where there is a focussed point in the optical fiber 9.

In the consideration described above, it can be concluded that the laser beam transmission state shown in the case (b) in FIG. 2 is the most advantage transmission state in the cases (a), (b), and (c) shown in FIG. 2.

Specifically, as described in the page 66–67 of the Laser Handbook (the Laser Society of Japan, 1982, OHMSYA), it is commonly known that the value $\phi_s$ for a laser beam of a standard mode (or $TEM_{00}$ mode) having a small power laser beam which is commonly used for optical communication can be obtained by analytical method.

Although, in general, a high power laser beam, especially, a laser beam generated by a solid state laser device, used for industrial processing is a multi-mode laser beam, however, there is no reports of the technique for optical communication using a multi-mode laser beam while keeping the state of the highly focusability of the multi-mode laser beam.

We study the optical communication with the high focusability of the high power laser beam and develop the method to obtain the value $\phi_s$ of the laser beam by using the value $M^2$ described above, and find the analytical equation in order to obtain the value $\phi_s$ by using the diameter of the laser beam waist and the opening angle of the laser beam.

Firstly, the following approximation is performed in order to calculate a laser beam whose focusability is expressed by the value $M^2$ like the calculation for the laser mode $TEM_{00}$. In this case, we use the laser beam having the diameter to which the energy of 86.5% of the laser beam is concentrated.

When the laser beam opening angle θ is expressed by the function $\theta(\lambda_1, M^2)$ of the wavelength λ of the laser beam and the value $M^2$, the following equation is obtained:

$$\theta(\lambda_1, M^2) = M^2 \cdot \theta(\lambda_1, 1).$$

On the other hand, when two Gaussian beams whose wavelengths are different to each other are concentrated into a same diameter, because the opening angle of the laser beam is in proportion to the wavelength of this laser beam, we obtain the following equation:

$$\theta(\lambda_2, 1) = (\lambda_2/\lambda_1) \cdot \theta(\lambda_1, 1).$$

Here we obtain $\theta(\lambda_1, M^2) = (\lambda_2, \lambda_1)$ when $\lambda_2 = M^2 \cdot \lambda_1$.

Thereby, the operation of the laser beam whose focusability is defined by the value $M^2$ may be approximately expressed with the Gaussian beam whose wavelength is replaced with the value $M^2 \cdot \lambda_1$.

By using the approximation described above, we obtain the value $\phi_s$ for the laser beam whose focusability is expressed by the $M^2$ value.

In the following operation, when the value $M^2$ is 1 ($M^2=1$), the $\phi_s$ of the laser beam is equal to that of the Gauss beam. The graded index optical fiber has a distribution of the square reflective index. For example, as described in the literature "Optical Electronics", p 42, A. Yariv, Saunder College Publishing, Harcourt Brace Jovanovich College Publishers, fourth Edition, p42, the refractive index of the optical fiber is expressed as following equation (2):

$$n(r) = n_0 \left( 1 - \frac{k_2}{2k} r^2 \right) \quad (2)$$

where, n(r) designates a refractive index at a position r from the center of the core of the optical fiber, $n_0$ is a refractive index at the center of the core of the optical fiber, $k=2\pi n/\lambda_0$ is a wavelength of a laser beam, $k_2$ is a constant value corresponding to the distribution of the refractive index in the optical fiber.

The following optical light matrix (3) in the graded index optical fiber is obtained:

$$\begin{bmatrix} A & B \\ C & D \end{bmatrix} = \begin{bmatrix} \cos\left(\sqrt{\frac{k_2}{k}}\, l\right) & \sqrt{\frac{k}{k_2}} \sin\left(\sqrt{\frac{k_2}{k}}\, l\right) \\ -\sqrt{\frac{k_2}{k}} \sin\left(\sqrt{\frac{k_2}{k}}\, l\right) & \cos\left(\sqrt{\frac{k_2}{k}}\, l\right) \end{bmatrix} \quad (3)$$

It is well known that the propagation of the Gaussian laser beam may be expressed by using the index q and the optical light matrix described by the equation (3). When, a curvature of the Gaussian laser beam is R, the radius of the Gaussian laser beam is ω, the wavelength of the Gaussian laser beam is λ, and the refractive index of the optical fiber is n, the following relationship (4) may be expressed:

$$\frac{1}{q} = \frac{1}{R} - iM^2 \frac{\lambda}{\pi n \omega^2} \quad (4)$$

When we consider that this equation (4) is expanded for a multi-mode laser beam by using the approximation described above, the following equation (5) is obtained:

$$\frac{1}{q} = \frac{1}{R} - i \frac{M^2 \lambda}{\pi n \omega^2} \quad (5)$$

In this case, in order to get the condition that the diameter of a laser beam is not changed in the graded index optical fiber, it is required to irradiate a plane wave of the laser beam into the incident side plane of the graded index optical fiber having a predetermined length and to get the condition that the plane wave of the laser beam having the same laser beam diameter of the incident side plane may be obtained at the outgoing side plane of the optical fiber.

In the plane wave, because R=∞, namely 1/R=0, only the second part of the right component in the equation (5) may be considered. When an incident laser beam and an outgoing laser beam in an optical system are designated by $q_1$ and $q_2$, the following equation (6) is obtained:

$$q_2 = \frac{Aq_1 + B}{Cq_1 + D} \quad (6)$$

Accordingly, when the equation (6) is solved for the value $\omega_s$ under the condition $q_1=q_2=-i\ (\pi n \omega_s^2/M^2\lambda)$, we may obtain the following result (7):

$$\omega_s = \left( \frac{M^2 \lambda}{\pi n \sqrt{\frac{k_2}{k}}} \right)^{\frac{1}{2}} \quad (7)$$

When the core diameter of the graded index optical fiber is $\phi_s$, and the difference of the refractive indexes of the center of the core and the side section of the core in the graded index optical fiber is Δn, the following equation (8) is obtained:

$$n_0 \frac{k_2}{2k} \left( \frac{\phi}{2} \right)^2 = \Delta n \quad (8)$$

The above equation (8) is inserted into the equation (7) for $\omega_s$ and when $n=n_0$, the following equation (9) is obtained:

$$\omega_s = \left( M^2 \frac{\phi_c}{2} \frac{\lambda}{\pi \sqrt{2n_0 \Delta n}} \right)^{\frac{1}{2}} \quad (9)$$

Accordingly, $\phi_s = 2\omega_s$ for the multi mode laser beam is given by the following equation (10):

$$\phi_s = 2 \left( M^2 \frac{\phi_c}{2} \frac{\lambda}{\pi \sqrt{2n_0 \Delta n}} \right)^{\frac{1}{2}} \quad (10)$$

By the discussion as described above, a standard incident laser beam diameter $\phi_s$ for highly focussed optical fiber transmission may be obtained.

Next, the equation $\phi_s$ as the index for focusability of a normal or an usual laser beam will be explained based on the beam waist diameter $\phi_0$, and the opening angle $\theta$ of a laser beam. As described above, there is the relationship, $M^2 = \pi \phi_0 \theta / 2\lambda$ between the laser beam opening angle $\theta$ and the value $M^2$. When this relationship is inserted into the equation $\phi_s$, the following equation (11) is given by:

$$\phi_s = \left( \frac{\phi_c \phi_0 \theta}{\pi \sqrt{2n_0 \Delta n}} \right)^{\frac{1}{2}} \quad (11)$$

Thereby, the value $\phi_s$ as the standard incident diameter of an optical fiber may be obtained for the laser beam whose focusability is expressed with the laser beam waist diameter and the laser beam opening angle in the highly focussed optical fiber transmission.

Here, we will explain an example how to obtain the value $\phi_s$.

For example, when the Nd: YAG laser beam having a wavelength $\lambda = 1.0649$ μm is propagated through a graded index optical fiber having $n_0 = 1.473$, $\Delta n = 0.021$, and the core diameter of 400 μm, the value $\phi_s$ becomes 148 μm. In this case, the incident angle $2\theta$in of the laser beam into the optical fiber becomes approximately 10.5 degree.

Figure 3:
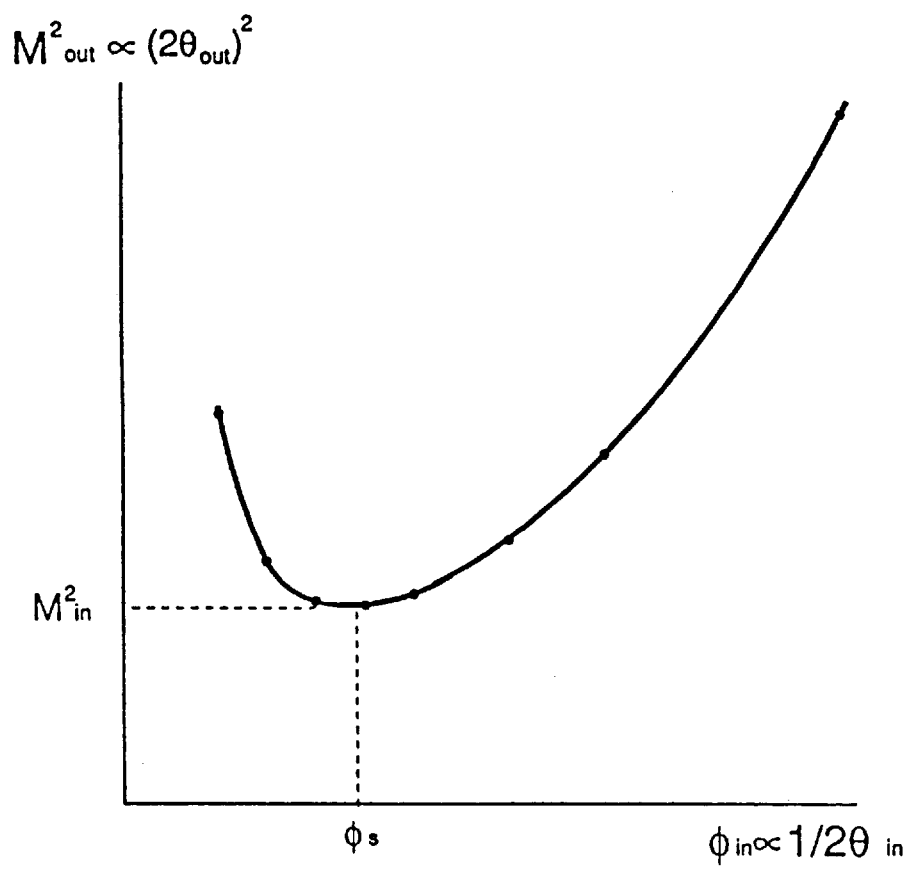
FIG. 3 is an explanately diagram showing the relationship between an incident side diameter and the focusability of an outgoing laser beam in a graded index optical fiber.

FIG. 3 is a diagram showing the experimental result for the measured $M^2$ value ($M^2$ out) of the outgoing laser beam corresponding to the change of the focus distance of the focussing lens 8 where the laser beam 70 is focussed at the incident side plane of the optical fiber 9 so that at the incident side plane of the optical fiber 9 the laser beam has the smallest focussed point of this laser beam.

In the experimental result shown in FIG. 3, the diameter $\phi_s$ of the incident laser beam is in proportion to the reciprocal of the incident angle $2\theta_{in}$.

As apparently shown in FIG. 3, the most highly focusability of the laser beam may be obtained because the value $M^2_{out}$ of the outgoing laser beam becomes approximately equal to the value $M^2_{in}$ of the incident laser beam when the diameter of the incident laser beam is set to near the value $\phi_s$.

On the other hand, the focusability of the outgoing laser beam is decreased when the incident angle $2\theta_{in}$ is not more than 8 degree by using the laser beam and the optical fiber 90 in the conventional optical transmission device shown in FIG. 35. This state is apparently different from the feature of incident/outgoing laser beam by using the ideal step index optical fiber as described in FIG. 35.

In addition, FIG. 3 clearly shows that it can be performed to transmit a laser beam without deterioration of the focusability of the incident laser beam if the diameter $\phi_{in}$ of the incident laser beam is in the range of $\phi_s \pm 50\%$ ($0.5 \leq \phi_{in} \leq 1.5\phi_s$). $0.5\phi_s$ to $2\phi_s$ ($0.5 \phi_s - < \phi_{in} - < 2\phi$)

In addition, it is now revealed that the focusability of the outgoing laser beam is deteriorated when the focussed point of the laser beam is shifted from the center point of the core of the optical fiber, the opening angle $\theta$out (a half angle) of the outgoing laser beam becomes small when the focusability of the outgoing laser beam from the graded index optical fiber is high, and the opening angle $\theta$out (half angle) is proportion to value of $$\sqrt{M^2_{out}}.$$

In the optical transmission device 100 of the embodiment 1 shown in FIG. 1, as described above, there is the smallest focussed point closed to the incident side plane of the optical fiber 9, the position of the focussing lens 8 is set so that the diameter of the smallest focussed point is a range of $0.5\phi_s$ to $2\phi_s$ clearly shown in the above discussion, the laser beam can be transmitted through the optical fiber 9 while keeping the high focusability of the laser beam. Accordingly, the laser beam having a higher focusability generated in a laser oscillator can be obtained from the optical fiber 9 while keeping the focusability of the laser beam.

The optical transmission device 100 of the embodiment 1 having the configuration shown in FIG. 1 may be applied to a transmission of a multi mode laser beam of $M^2 < 50$, especially $M^2 < 40$ in addition to the transmission of the Gaussian laser beam while keeping the focusability of the laser beam. In other words, the optical transmission device 100 may be applied to the transmission of a laser beam having $\pi \phi 0 \theta / \lambda$ is not more than 100, especially, not more than 80 based on the relationship of $M^2 = \pi \phi_0 \theta / 2\lambda$.

In addition, in the optical transmission device 100 of the embodiment 1, there is the beam waist of the laser beam 70 near the output side of the laser oscillator 10. If this condition is not satisfied, the value $\phi$s and the focus length fs for $\phi_s$ can be easily obtained when the diameter of the laser beam waist $\phi_1$ and the opening angle $\theta_1$ of the laser beam are measured. Specifically, by utilizing the characteristics that the product of the diameter of the laser beam and the opening angle of the laser beam takes a constant value during the transmission through the optical lens system, firstly, the value $\phi_s$ is obtained by using the relationship $\phi_1 \theta_1 = \phi_0 \theta$, and we obtain: $f_s = f_1 \phi_s / \phi_1$ by using $\phi = 2f_{74}$.

In addition, when the beam waist of the laser beam is in the laser oscillator 10, a calculation error of the focus point fs becomes small by using the diameter of the laser beam at the outgoing side of the laser oscillator 10 so long as the opening angle of the laser beam is not extremely larger. Therefore it may be acceptable to calculate the focus point by using the diameter and the opening angle of the laser beam described in a catalog.

In addition, in the optical transmission device 100 of the embodiment 1, the combination of the movable stage to Z axis and the cross movable stage is used, however, it may be acceptable to use a holder having another configuration which is capable of slightly adjusting the position of the optical lens.

Furthermore, in the optical transmission device 100 of the embodiment 1, the focussing lens holder 101 is capable of adjusting the position of the focussing lens, however, it may be acceptable that the incident side holder 102 of the optical fiber has the same adjusting function.

Moreover, in the optical transmission device 100 of the embodiment 1, the focussing lens 8 focuses the laser beam 70 in order to irradiate the laser beam 70 onto or near the smallest focussed point on the incident side plane of the optical fiber 9, and the diameter of the laser beam 70 has a predetermined value at the smallest focussed point, however, a mirror may be used instead of the focussing lens 8.

EMBODIMENT 2

Figure 4:
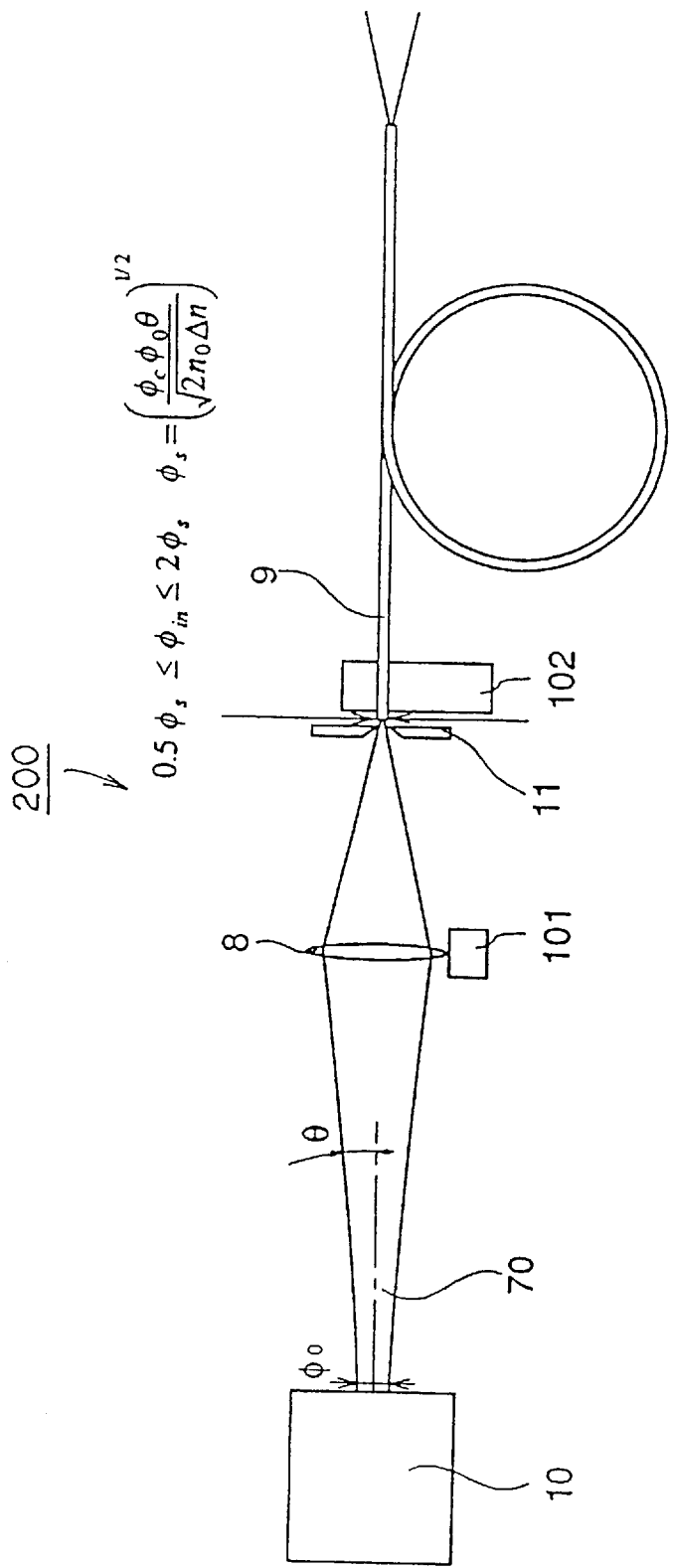
FIG. 4 is a configuration diagram showing a configuration of an optical transmission device as the embodiment 2 according to the present invention.

FIG. 4 is a configuration diagram showing a configuration of an optical transmission device 200 of the embodiment 2 according to the present invention.

In the optical transmission device 200 shown in FIG. 4, components which are the same components used in the optical transmission device 100 of the embodiment 1 shown in FIG. 1 in configuration and function are referenced with the same reference numbers and the explanations for them are omitted here.

In the optical transmission device 200 shown in FIG. 4, a reference number designates an aperture whose opening diameter is larger than the value $\phi_s$, and smaller than the diameter $\phi_c$ of the core of the optical fiber. In addition, the center position of the opening of the aperture 11 is approximately equal to the center position of the core of the optical fiber 9. The aperture 11 is placed near the incident side plane of the optical fiber 9.

Although the configuration of the focussing lens holder 101 is shown briefly in FIG. 4, like the focussing lens holder 101 in the optical transmission device 100 shown in FIG. 1, the configuration of the focussing lens holder 101 in the embodiment 2 also has the combination of a movable stage for moving it toward the optical axis direction by hand and a cross movable stage for moving it toward the diameter direction of the optical fiber 9.

In the optical transmission device 200, the laser beam 70 emitted from the laser oscillator 10 having the diameter $\phi_0$ of the beam waist and the opening angle $\theta$ of the laser beam is transmitted to the focussing lens 8 and the aperture 11 and focussed to the laser beam whose diameter is $\phi_{in}$ having a range of 0.5$\phi_s$ to 2$\phi_s$ and irradiated onto the incident side plane of the optical fiber 9. Then, the laser beam is passed through the optical fiber 9 while keeping the focusability of the laser beam and then transmitted to outside of the optical fiber 9.

In this case, the laser beam which is shifted from the center of the optical fiber 9 is intercepted by the aperture 11.

By the optical transmission device 200 of the embodiment 2 shown in FIG. 4, even if the laser beam 9 is irradiated to another point which is different from the center of the optical fiber 9 during optical axis adjusting operation, the aperture 11 can prevent to irradiate the laser beam to a clad of the optical fiber and to a seal portion of the optical fiber.

In addition, when various types of errors are caused, such as an irradiating position error where the laser beam irradiation position is different from the center of the optical fiber 9, and a distance error where the distance between the focussing lens 8 and the incident side plane of the optical fiber 9 is shifted from a predetermined most suitable distance, the output of the laser beam is decreased because the laser beam is irradiated to the aperture 11. In this case, the position of the focussing lens 8 may be adjusted easily by monitoring the power of the laser beam by using the power meter which is placed at the outgoing side of the optical fiber.

EMBODIMENT 3

Figure 5:
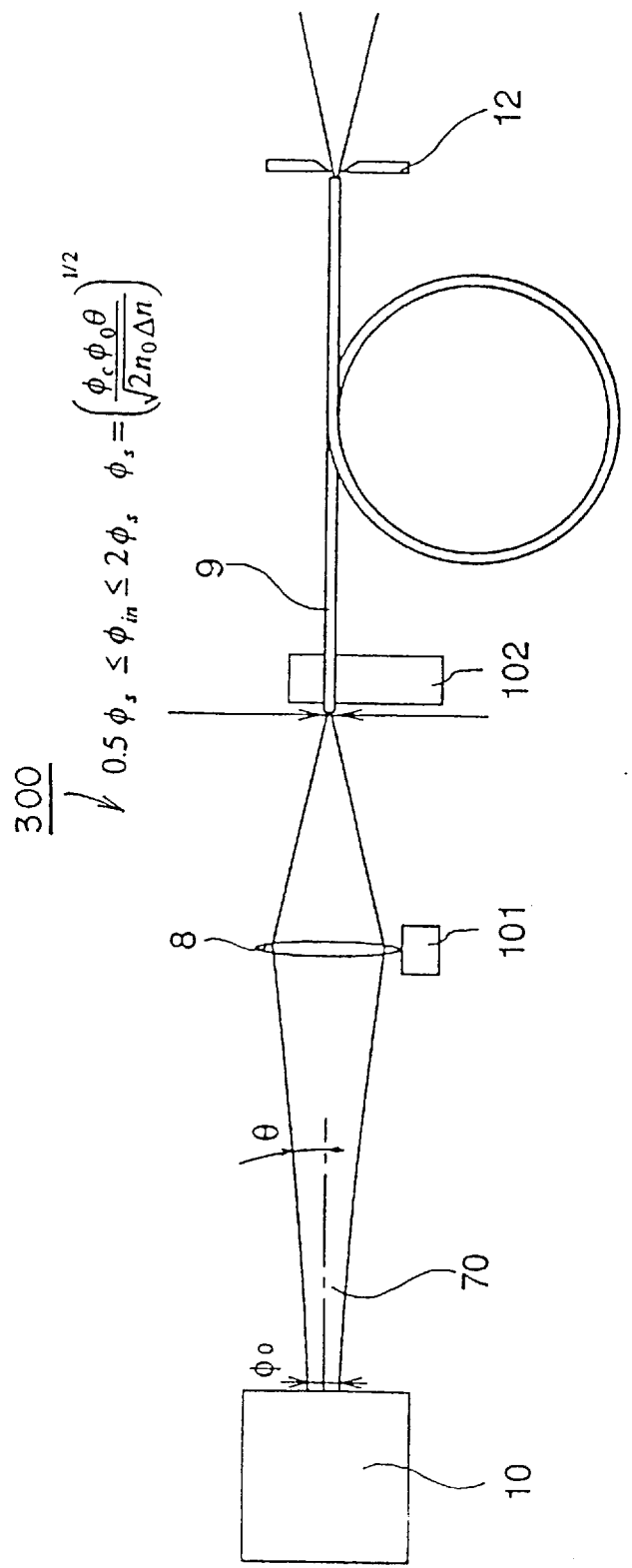
FIG. 5 is a configuration diagram showing a configuration of an optical transmission device as the embodiment 3 according to the present invention.

FIG. 5 is a configuration diagram showing a configuration of an optical transmission device 300 of the embodiment 3 according to the present invention.

In the optical transmission device 300 shown in FIG. 5, components which are the same components used in the optical transmission device 100 of the embodiment 1 shown in FIG. 1 in configuration and function are referenced with the same reference numbers and the explanations for them are omitted here.

In the optical transmission device 300 shown in FIG. 5, a reference number 12 designates an aperture whose opening diameter is greater than the value $\phi_s$ and smaller than the diameter of the core of the optical fiber 9. In addition, the center of the opening of the aperture 12 is approximately equal to the center of the core of the optical fiber 9. The aperture 12 is placed near the outgoing side of the optical fiber 9.

In the optical transmission device 300, the laser beam 70 emitted from the laser oscillator 10 having the diameter $\phi_0$ of the beam waist and the opening angle $\theta$ of the laser beam is transmitted to the focussing lens 8 and focussed to the laser beam whose diameter is $\phi_{in}$ having a range of 0.5 $\phi_s$ to 2$\phi_s$ and irradiated onto the incident side plane of the optical fiber 9. Then, the laser beam is passed through the optical fiber 9 while keeping the focusability of the laser beam and through the aperture 12, and then transmitted to outside of the optical fiber 9.

By the optical transmission device 300 of the embodiment 3 shown in FIG. 5, when the outgoing laser beam from the optical fiber 9 is used for processing a target work, for example, even if the laser beam is reflected by a target work and then irradiated into the optical fiber 9, the aperture 12 prevents to damage the optical fiber 9 by the reflected laser beam from the target work.

In addition, when various types of errors are caused, such as an irradiating position error where the laser beam irradiation position is different from the center of the optical fiber 9, and a distance error where the distance between the focussing lens 8 and the incident side plane of the optical fiber 9 is shifted from a predetermined most suitable distance, the output of the laser beam through the aperture 12 is decreased because the opening angle of the laser beam becomes large and a part of the laser beam is also irradiated to the aperture 12. In this case, a power meter is placed near the outgoing side of the aperture 12 in order to monitor the power of the laser beam through the aperture 12, so that the position of the focussing lens 8 may be adjusted easily by using the output of the power meter.

EMBODIMENT 4

Figure 6:
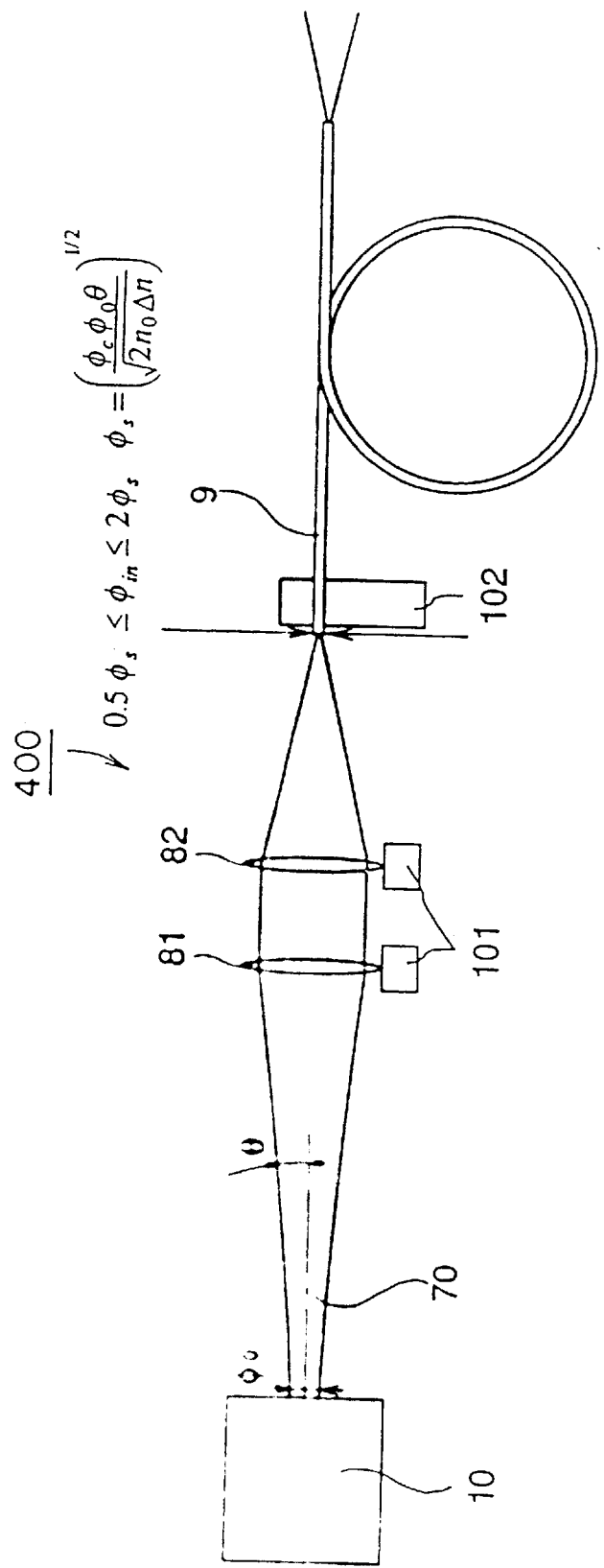
FIG. 6 is a configuration diagram showing a configuration of an optical transmission device as the embodiment 4 according to the present invention.

FIG. 6 is a configuration diagram showing a configuration of an optical transmission device 400 of the embodiment 4 according to the present invention.

In the optical transmission device 400 shown in FIG. 6, components which are the same components used in the optical transmission device 100 of the embodiment 1 shown in FIG. 1 in configuration and function are referenced with the same reference numbers and the explanations for them are omitted here.

In the optical transmission device 400 shown in FIG. 6, reference numbers 81 and 82, each of which designates a focussing lens, and a reference number 101 denotes a focussing lens holder on which each focussing lens is mounted.

In the optical transmission device 400, the laser beam 70 emitted from the laser oscillator 10 having the diameter $\phi_0$ of the beam waist and the opening angle $\theta$ of the laser beam is transmitted to the focussing lenses 81 and 82 and focussed into the laser beam whose diameter is $\phi_{in}$ having a range of 0.5 $\phi_s$ to 2$\phi_s$ and irradiated onto the incident side plane of the optical fiber 9. Then, the laser beam is passed through the optical fiber 9 while keeping the focusability of the laser beam, and then transmitted to outside of the optical fiber 9.

In the optical transmission device 400 of the embodiment 4, the diameter of the laser beam 70 at the incident side plane of the optical fiber 9 may be easily changed by changing the distance between the two focussing lenses 81 and 82. Accordingly, the focussing lenses 81 and 82 in the optical transmission device 400 is made by using available lenses in a low cost.

In addition, by the optical transmission device 400, even if the diameter of the beam waist of the laser beam emitted from the laser oscillator 10, the position of the beam waist, and the opening angle of the laser beam are changed, the diameter $\phi_{in}$ of the laser beam over a range of 0.5 $\phi_s$ to 2 $\phi_s$ may be easily obtained.

In addition, the focussing lenses 81 and 82 are a separate type which are separated to each other in the optical transmission device 400 of the embodiment 4, but these focussing lenses 81 and 82 may be made up of a single integral focussing lens.

EMBODIMENT 5

Figure 7:
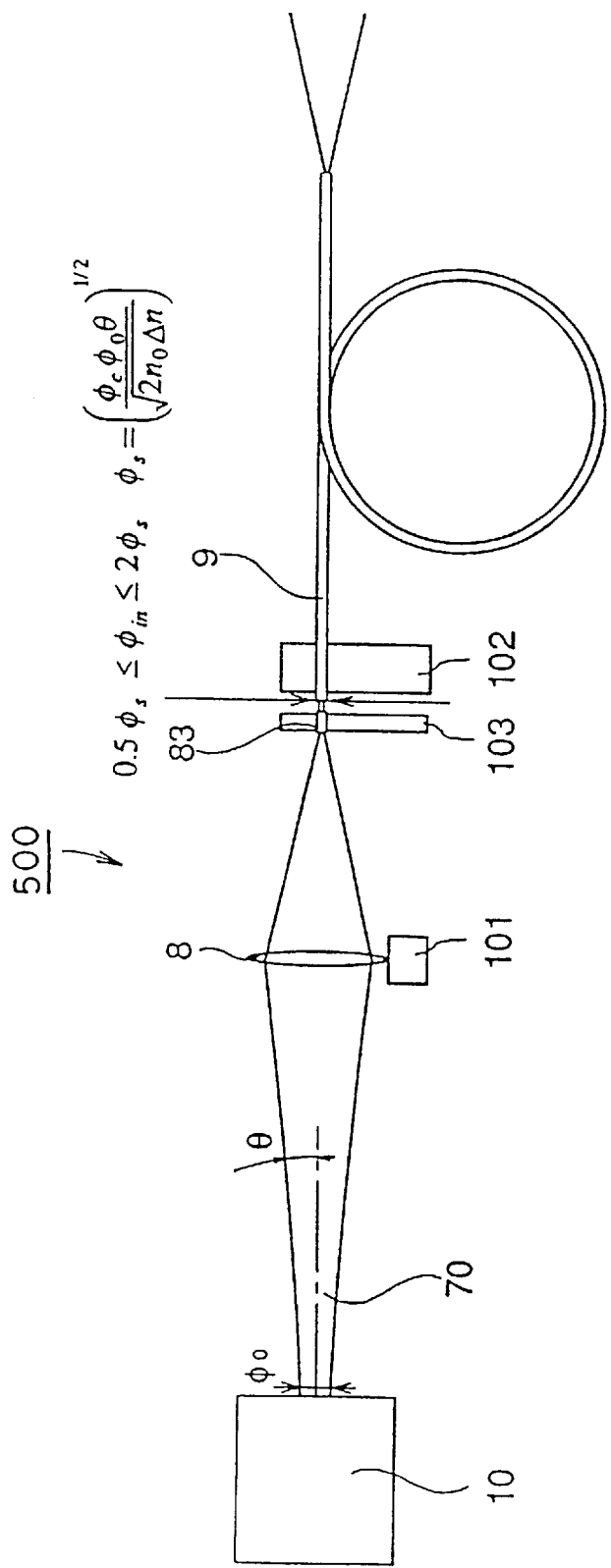
FIG. 7 is a configuration diagram showing a configuration of an optical transmission device as the embodiment 5 according to the present invention.

FIG. 7 is a configuration diagram showing a configuration of an optical transmission device 500 of the embodiment 5 according to the present invention.

In the optical transmission device 500 shown in FIG. 7, components which are the same components used in the optical transmission device 100 of the embodiment 1 shown in FIG. 1 in configuration and function are referenced with the same reference numbers and the explanations for them are omitted here.

In the optical transmission device 500 shown in FIG. 7, a reference number 83 designates a graded index optical lens which is placed connected to or near the incident side plane of the optical fiber 9. Both surfaces of the lenses 83 are coated with a non-reflective material which does not reflect the wavelength of the laser beam 70. a reference number 103 denotes a graded index optical lens holder. The graded index optical lens 83 is mounted on the holder 103 so that the center axis of the graded index optical lens 83 is equal to the optical axis of the optical fiber 9.

In the optical transmission device 500, the laser beam 70 emitted from the laser oscillator 10 having the diameter $\phi_0$ of the beam waist and the opening angle θ of the laser beam is transmitted to the focussing lens 8, and focussed, and further transmitted to the graded index optical fiber 83. In this case, the laser beam 70 is further focussed into the laser beam whose diameter is in having a range of 0.5 $\phi$to at the incident side plane of the optical fiber 9 and irradiated onto the incident side plane of the optical fiber 9. Then, the laser beam 70 is passed through the optical fiber 9 while keeping the focusability of the laser beam, and then transmitted to outside of the optical fiber 9.

As comparing with the optical transmission device 400 of the embodiment 4, the graded index optical fiber 83 is used as one of the focussing lenses 83 and 84, so that the diameter of the laser beam 70 may be widely changed in the optical transmission derive 500. Accordingly, the diameter of the laser beam 70 is widely changed at the incident side plane of the optical fiber 9 by moving slightly the position of the focussing lens 8 and the graded index optical fiber 83. Thereby, the optical transmission device may easily deal with the change of the focusability of the laser beam emitted from the laser oscillator.

In the optical transmission derive 500 of the embodiment 5 described above, the graded index optical fiber 83 is located near the incident side plane of the optical fiber 9, but the present invention is not limited by this configuration, it may be acceptable that the graded index optical lens 83 is connected to the optical fiber 9 by an optical contact member. In addition, it may also be acceptable that the graded index optical lens 83 is joined to the optical fiber 9 with an index matching fluid. In this case, there is no reflection loss at the side plane between the graded index optical lens 83 and the optical fiber 9, so that the transmission efficiency of the laser beam may be increased.

EMBODIMENT 6

Figure 8:
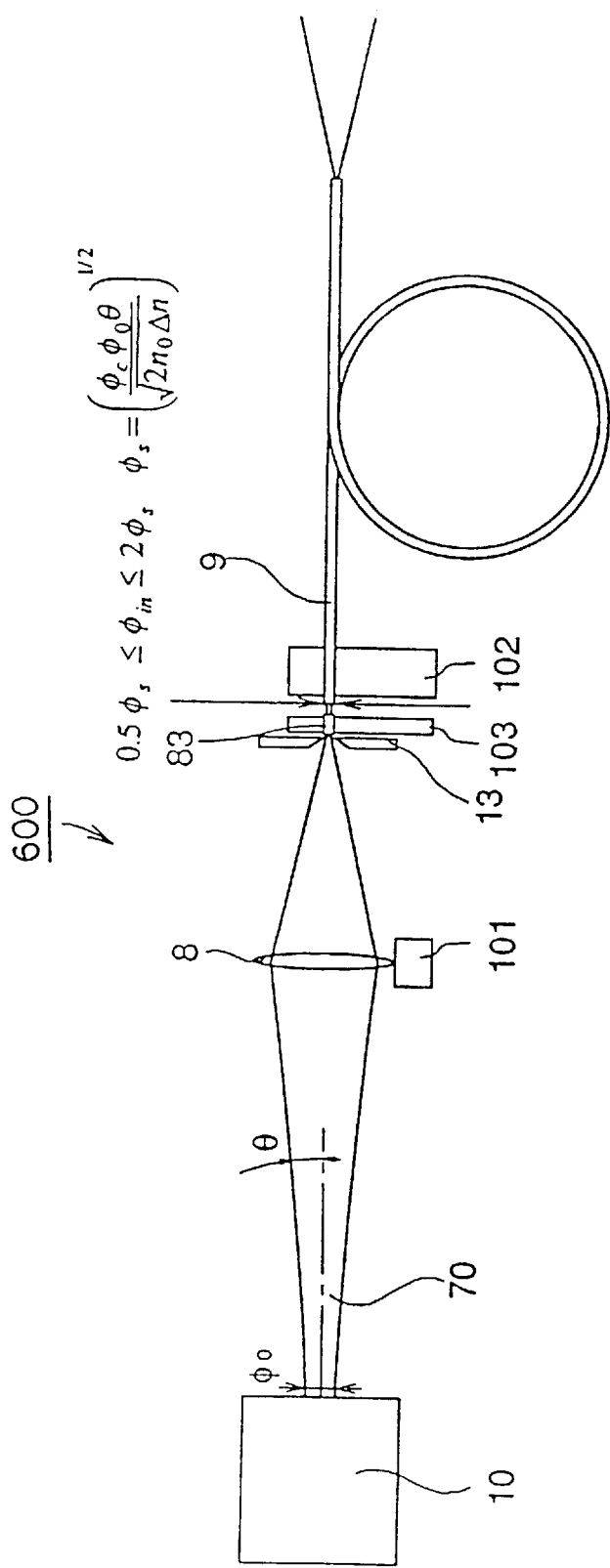
FIG. 8 is a configuration diagram showing a configuration of an optical transmission device as the embodiment 6 according to the present invention.

FIG. 8 is a configuration diagram showing a configuration of an optical transmission device 600 of the embodiment 6 according to the present invention.

In the optical transmission device 600 shown in FIG. 8, components which are the same components used in the optical transmission device 500 of the embodiment 5 shown in FIG. 7 in configuration and function are referenced with the same reference numbers and the explanations for them are omitted here.

In the optical transmission device 600 shown in FIG. 8, a reference number 13 designates an aperture, the center of the opening of the aperture 13 is approximately equal to the optical axis of the optical fiber 9. The aperture 13 is placed near the graded index optical fiber 83.

In the optical transmission device 600, the laser beam 70 emitted from the laser oscillator 10 having the diameter $\phi_0$ of the beam waist and the opening angle θ of the laser beam is transmitted to the focussing lens 8 and the aperture 13. The laser beam passed through the aperture 13 is transmitted to the graded index optical lens 83 and focussed into the laser beam whose diameter is $\phi_{in}$ having a range of 2$\phi_s$ by the graded index optical lens 83 and irradiated onto the incident side plane of the optical fiber 9. Then, the laser beam is passed through the optical fiber 9 while keeping the focusability of the laser beam, and then transmitted to outside of the optical fiber 9. In this case, a part of the laser beam which is shifted from the optical axis of the graded index optical lens 83 is cut by the aperture 13.

By using the optical transmission device 600 of the embodiment 6, even if the laser beam 70 is irradiated to another point which is different from the graded index optical lens 83 during optical axis adjusting operation, the aperture 11 can prevent to irradiate the laser beam to a clad of the optical fiber and to a seal portion of the optical fiber.

In addition, when various types of errors are caused, such as an irradiating position error where the laser beam irradiation position is different from the center of the optical axis of the graded index optical lens 83, and a distance error where the distance between the focussing lens 8 and the incident side plane of the optical fiber 9 is shifted from a predetermined most suitable distance, the output of the laser beam is decreased because the laser beam is irradiated to the aperture 11. In this case, the position of the focussing lens 8 may be adjusted easily by monitoring the power of the laser beam by using the power meter which is placed at the outgoing side of the optical fiber.

EMBODIMENT 7

Figure 9:
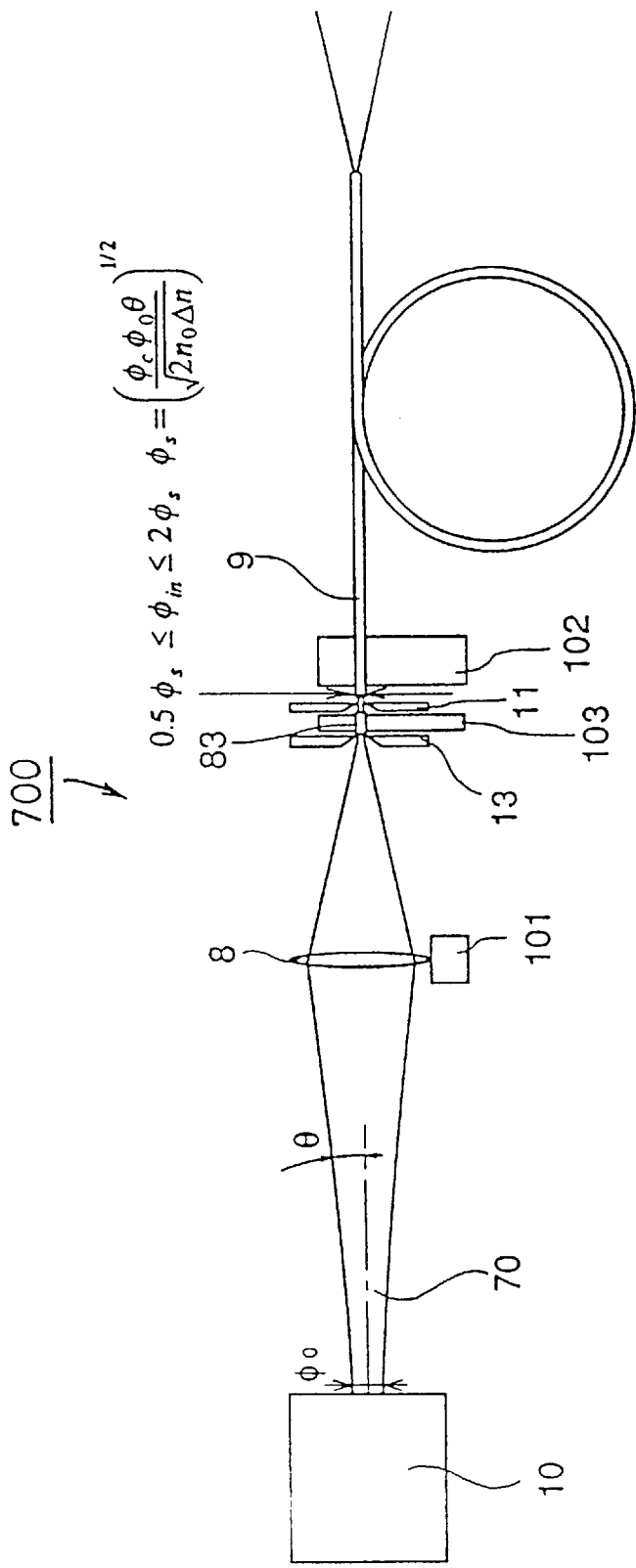
FIG. 9 is a configuration diagram showing a configuration of an optical transmission device as the embodiment 7 according to the present invention.

FIG. 9 is a configuration diagram showing a configuration of an optical transmission device 700 of the embodiment 7 according to the present invention.

In the optical transmission device 700 shown in FIG. 9, components which are the same components used in the optical transmission device 600 of the embodiment 6 shown in FIG. 8 in configuration and function are referenced with the same reference numbers and the explanations for them are omitted here.

The optical transmission device 700 shown in FIG. 9 has the configuration where apertures 13 and 11 are placed near the incident side of the graded index optical lens 83 and near the incident side of the optical fiber 9, respectively.

In the optical transmission device 700, the laser beam 70 emitted from the laser oscillator 10 having the diameter $\theta_0$ of the beam waist and the opening angle θ of the laser beam is transmitted to the focussing lens 8 and the aperture 13. The laser beam passed through the aperture 13 is transmitted to the graded index optical lens 83. Then the laser beam is transmitted to the incident side plane of the optical fiber 9 after through the graded index optical lens 83 and the aperture 11. The laser beam is focussed into the laser beam whose diameter is $\phi_{in}$ having a range of 0.5 $\phi_s$ to 2 $\phi_s$ by the graded index optical lens 83 and irradiated onto the incident side plane of the optical fiber 9. Then, the laser beam is passed through the optical fiber 9 while keeping the focusability of the laser beam, and then transmitted to outside of the optical fiber 9. In this case, a part of the laser beam which is shifted from the optical axis of the graded index optical lens 83 and the center of the core of the optical fiber 9 is cut by the aperture 11.

In the optical transmission device 700 of the embodiment 7, only because the laser beam whose optical axis is equal to the optical axis of the graded index optical lens 83 and the center of the core of the optical fiber 9 is transmitted through the optical fiber 9, so that it may be prevented to damage the optical fiber 9 caused by the position-shift from the optical axis.

In addition, by incorporating the power meter and the like in the optical transmission device, it may be performed to adjust or change the position of the focussing lens and the graded index optical lens.

EMBODIMENT 8

Figure 10:
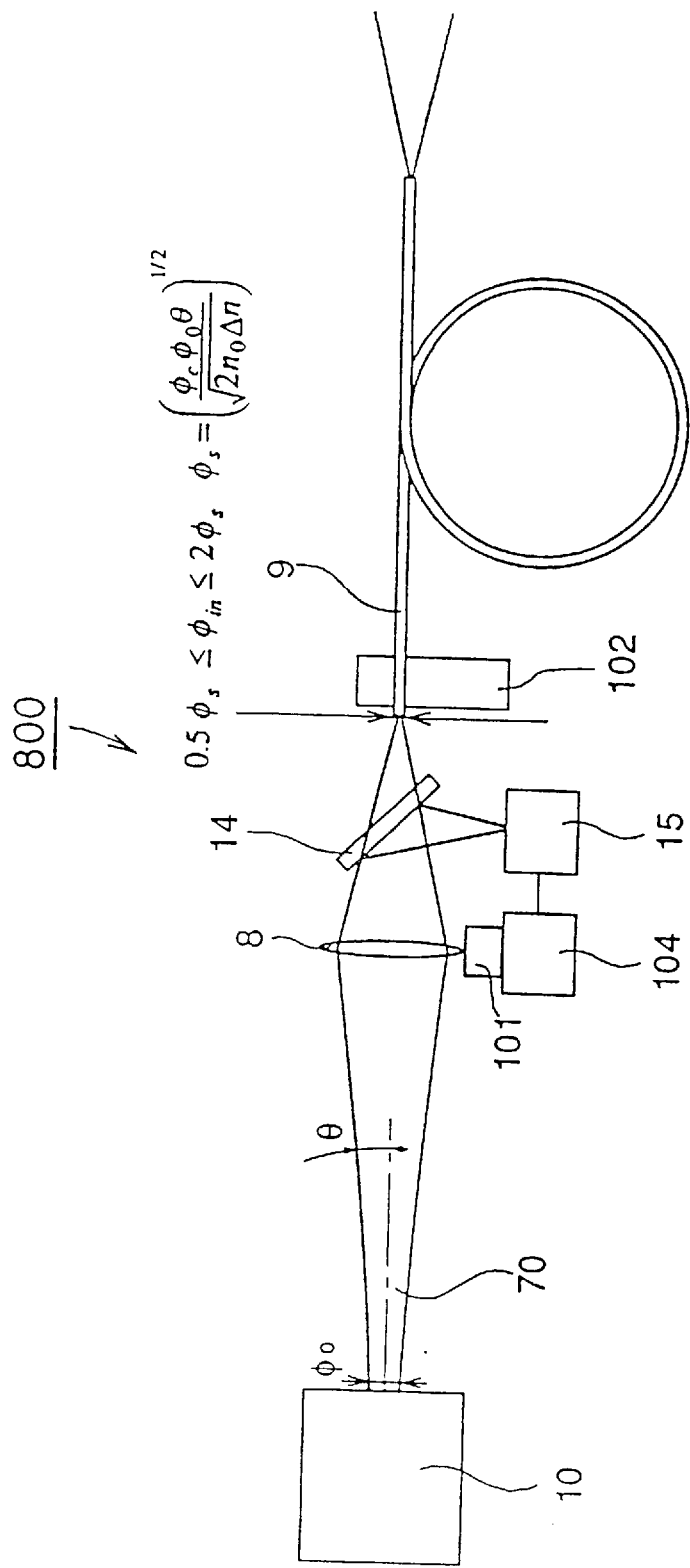
FIG. 10 is a configuration diagram showing a configuration of an optical transmission device as the embodiment 8 according to the present invention.

FIG. 10 is a configuration diagram showing a configuration of an optical transmission device 800 of the embodiment 8 according to the present invention.

In the optical transmission device 800 shown in FIG. 10, components which are the same components used in the optical transmission device 100 of the embodiment 1 shown in FIG. 1 in configuration and function are referenced with the same reference numbers and the explanations for them are omitted here.

In the optical transmission device 800 shown in FIG. 10, a reference number 14 designates a laser beam splitter for transmitting a part of the laser beam 70 to the optical fiber 9. A reference number 15 denotes an incident laser beam monitor device for detecting the power of the laser beam 70 after the laser beam 70 is passed through the laser beam splitter 14. The incident laser beam monitor device 15 is placed so that the distance between a laser beam detection plane of the monitor device 15 and the laser beam splitter 14 is approximately equal to the distance between the incident side plane of the optical fiber 9 and the laser beam splitter 14. For example, the position of the laser beam and the diameter of the laser beam are calculated by using the monitor device 15 which detects the power of the laser beam 70 after the laser beam 70 is passed through the laser beam splitter 14.

A reference number 104 designates an optical lens holder movable device for moving the optical lens holder 101 so that the diameter and the position of the laser beam 70 detected by the incident laser beam monitor device 105 become designed values.

Specifically, although it is not shown in the optical transmission device 800 of the embodiment 8 shown in FIG. 10, the optical lens holder movable device 104 comprises a Direct Current (DC) motor and a piezo element having a piezoelectric property, for example, which is connected to the movable stage and the cross movable stage forming the optical lens holder 101 in the optical transmission device 100 shown in FIG. 1 so that the position of the laser beam 70 is adjusted automatically.

In the optical transmission device 800, the laser beam 70 emitted from the laser oscillator 10 having the diameter $\phi_0$ of the beam waist and the opening angle θ of the laser beam is transmitted to the focussing lens 8 and the laser beam splitter 14. Most power of the laser beam 70 is passed through the splitter 14 because the focussing lens 8 provides the focussed laser beam to the splitter 14. A part of the laser beam reflected by the laser beam splitter 14 is focussed into a laser beam, whose diameter is equal to the laser beam passed through the splitter 14 and transmitted to the incident side plane of the optical fiber 9. The laser beam reflected by the splitter 14 is detected by the incident laser beam monitor device 15. The incident laser beam monitor device 15 calculates the diameter of the laser beam and the position of the laser beam. Based on the output from the monitor device 15, the optical lens holder device 104 moves the focussing lens holder 101 by using the DC motor or the piezo element. In an actual example, for example, the value of the position-shift for the optical lens holder 101 is determined based on a value of the position-shift from the predetermined value in the X axis direction and the Y axis direction.

In addition, about the most suitable position of the focussing lens 8 in the X axis direction, the stage in the optical lens holder 101 is moved so that the diameter of the laser beam has the smallest value, namely most focused value. As the result, the laser beam 70 is focussed and transmitted to the center of the incident side plane of the optical fiber 9. The diameter of the focussed laser beam is $\phi_{in}$ having a range of 0.5$\phi_s$ to 2 $\phi_s$ Then, the laser beam is passed through the optical fiber 9 while keeping the focusability of the laser beam, and then transmitted to outside of the optical fiber 9.

In the optical transmission device 800 of the embodiment 8, it may be performed automatically to focus the laser beam in the most suitable way, and to adjust and change the optical axis of the laser beam corresponding to the change of the incident direction of the laser beam.

EMBODIMENT 9

Figure 11:
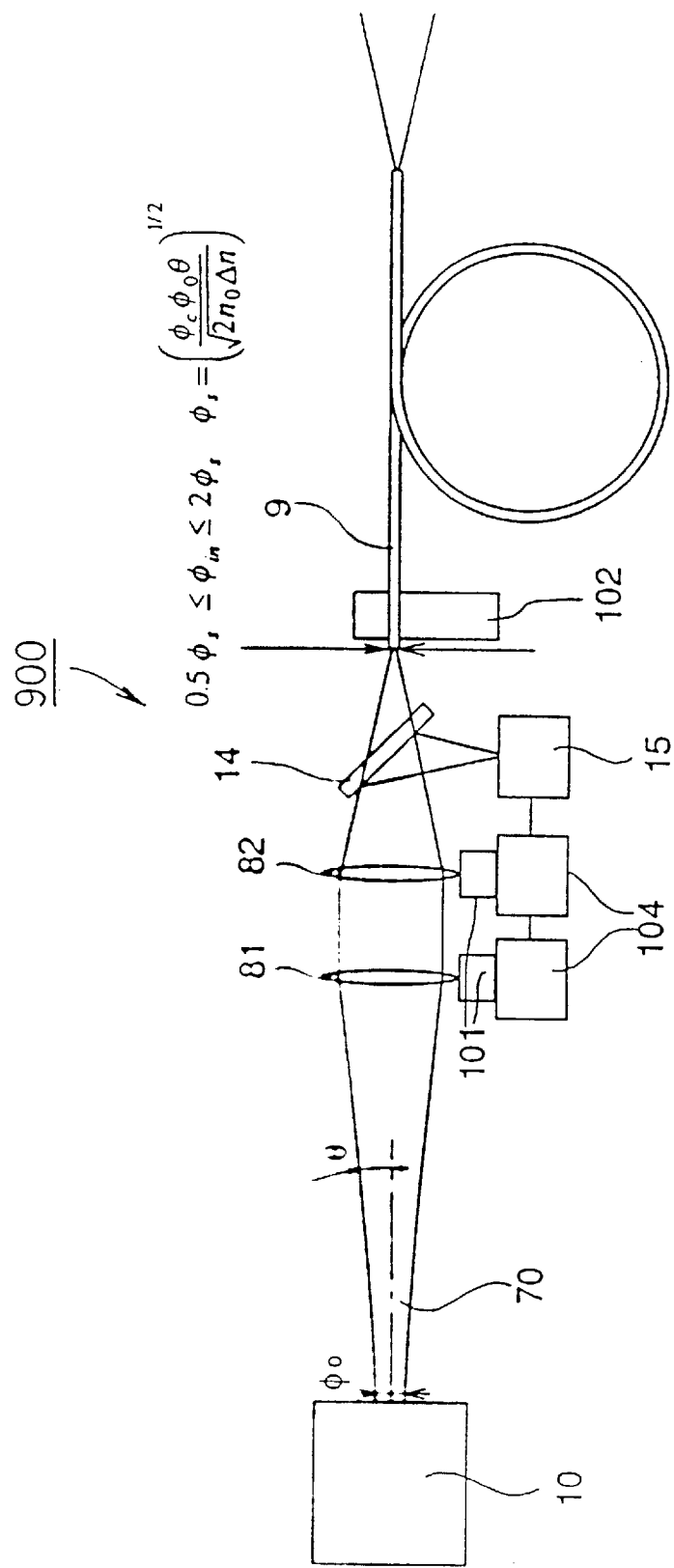
FIG. 11 is a configuration diagram showing a configuration of an optical transmission device as the embodiment 9 according to the present invention.

FIG. 11 is a configuration diagram showing a configuration of an optical transmission device 900 of the embodiment 9 according to the present invention.

In the optical transmission device 900 shown in FIG. 11, components which are the same components used in the optical transmission device 800 of the embodiment 8 shown in FIG. 10 in configuration and function are referenced with the same reference numbers and the explanations for them are omitted here.

In the optical transmission device 900 of the embodiment 9, two focussing lenses 81 and 82 or a pair of focussing lenses 81 and 82 are incorporated in addition to the configuration of the optical transmission device 800 of the embodiment 8 shown in FIG. 10.

In the optical transmission device 900, the positions of the focussing lenses 81 and 82 may be changed while monitoring the diameter and the position of the laser beam 70 at the incident side plane of the optical fiber 9 by the incident laser beam monitor device 15, so that the laser beam may be irradiated to the center of the core of the optical fiber 9 by tracing automatically the change of the focusability and the laser beam waist so that the diameter of the laser beam 70 is in a range of 2$\phi_s$ even if the focusability and the laser beam waist of the laser beam 70 are changed.

The explanations for effects, operation and configuration of other components in the optical transmission device 900 are omitted here because these are same as that of the optical transmission device 800 of the embodiment 8 shown in FIG. 10.

EMBODIMENT 10

Figure 12:
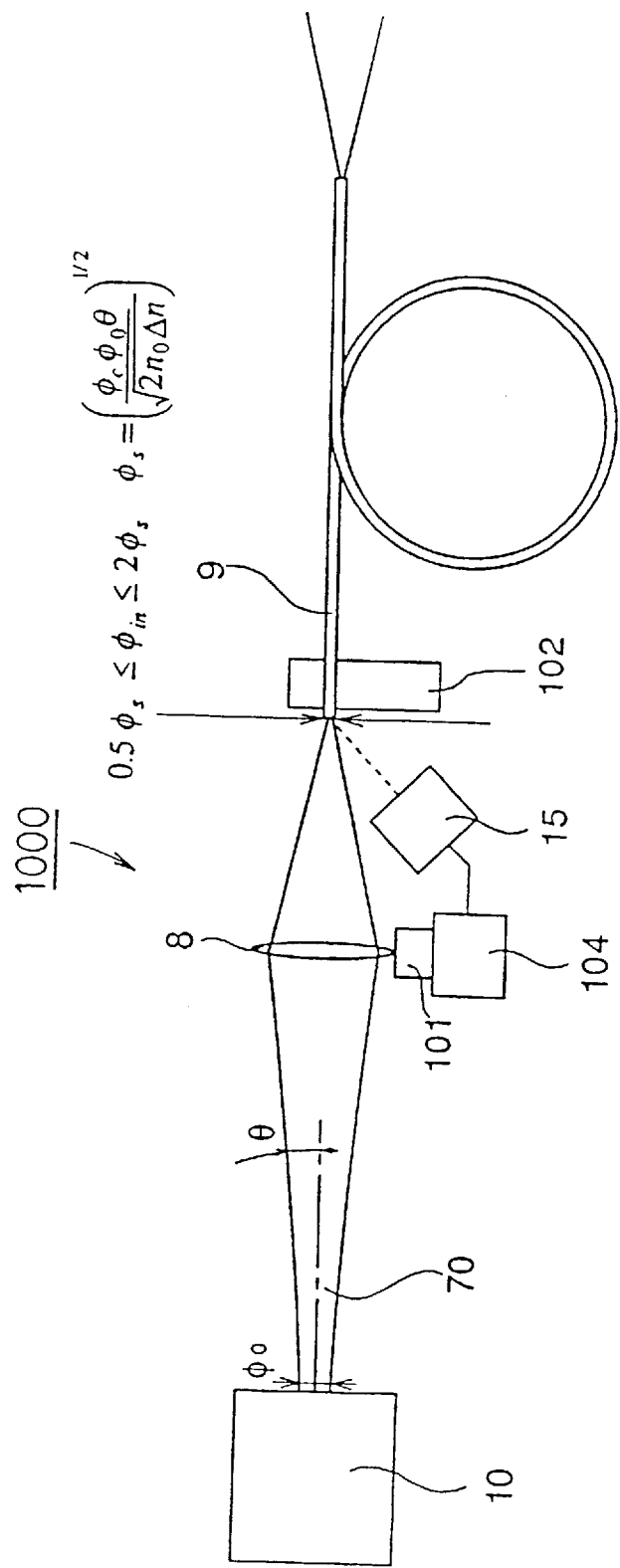
FIG. 12 is a configuration diagram showing a configuration of an optical transmission device as the embodiment 10 according to the present invention.

FIG. 12 is a configuration diagram showing a configuration of an optical transmission device 1000 of the embodiment 10 according to the present invention.

In the optical transmission device 1000 shown in FIG. 12, components which are the same components used in the optical transmission device 900 of the embodiment 9 shown in FIG. 11 in configuration and function are referenced with the same reference numbers and the explanations for them are omitted here.

In the optical transmission device 1000 of the embodiment 10 shown in FIG. 12, a reference number 15 designates an incident laser beam monitor device like the incident laser beam monitor device used in the optical transmission devices 800 and 900 as the embodiments 8 and 9 as shown in FIGS. 10 and 11 basically, but the incident laser beam monitor device 15 of the embodiment 10 has an image input device such as a Charge Coupled Device (CCD) camera device. The incident laser beam monitor device 15 of the embodiment 10 detects directly the incident side plane of the optical fiber 9. Similar to the optical transmission device 800 of the embodiment 8, the optical transmission device 1000 of this embodiment 10 is capable of adjusting the optical axis of the laser beam automatically. In addition, because the optical transmission device 1000 detects directly the incident side plane of the optical fiber 9, it may be performed to detect a damage of the incident side of the optical fiber 9 and used as a safety device.

EMBODIMENT 11

Figure 13:
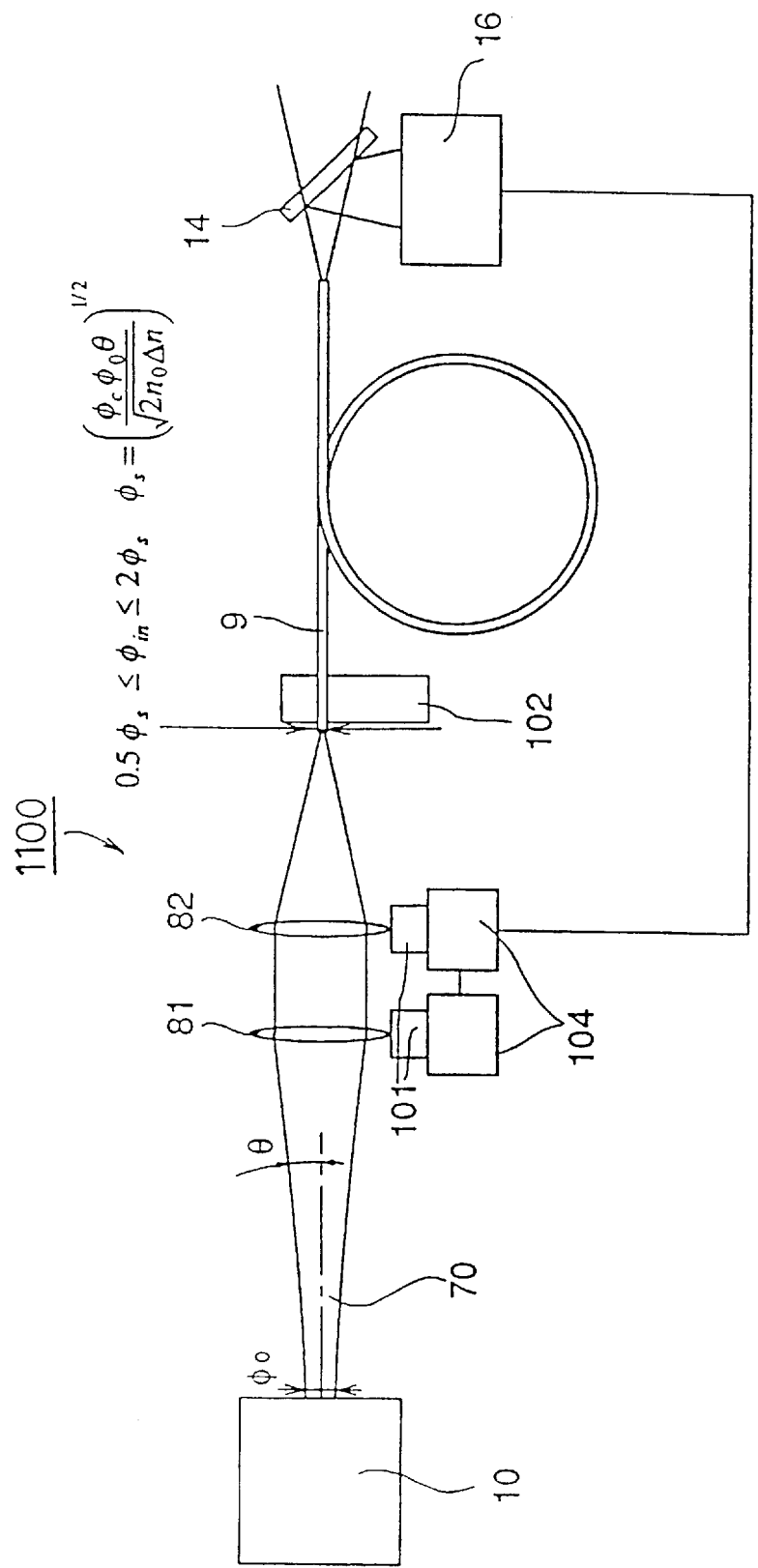
FIG. 13 is a configuration diagram showing a configuration of an optical transmission device as the embodiment 11 according to the present invention.

FIG. 13 is a configuration diagram showing a configuration of an optical transmission device 1100 of the embodiment 11 according to the present invention.

In the optical transmission device 1100 shown in FIG. 13, components which are the same components used in the optical transmission device 900 of the embodiment 9 shown in FIG. 11 in configuration and function are referenced with the same reference numbers and the explanations for them are omitted here.

In the optical transmission device 1100 of the embodiment 11, a reference number 14 designates a laser beam splitter for reflecting a part of the laser beam from the optical fiber 9. A reference number 16 denotes an outgoing laser beam monitor device for measuring the diameter of the outgoing laser beam from the optical fiber 9 by detecting the power of the laser beam passed through the laser beam splitter 16.

In the optical transmission device 1100, the laser beam 70 emitted from the laser oscillator 10 having the diameter $\phi_0$ of the beam waist and the opening angle $\theta$ of the laser beam is transmitted to the focussing lenses 81 and 82 and then transmitted to the incident side plane of the optical fiber 9. The laser beam is focussed into the laser beam whose diameter is $\phi_{in}$ having a range of $0.5\phi_s$ to $2\phi_s$ by the focussing lenses 81 and 82 and irradiated onto the incident side plane of the optical fiber 9. Then, the laser beam is passed through the optical fiber 9 while keeping the focusability of the laser beam, and then transmitted to outside of the optical fiber 9.

Most of the laser beam passed through the laser beam splitter 14 is used for processing operation and other part of the laser beam which is reflected by the laser beam splitter 14 is transmitted to the outgoing laser beam monitor device 16. The outgoing laser beam monitor device 16 calculates the data regarding to the diameter of the outgoing laser beam from the optical fiber 9 and transmits the data to the optical lens holder 104. The optical lens holder 104 receives the data from the outgoing laser beam monitor device 16 and adjusts and moves the positions of the focussing lenses 81 and 82 so that the diameter of the outgoing laser beam measured by the outgoing laser beam monitor device 16 has the smallest value.

As described above, the opening angle of the laser beam becomes smaller and the diameter of the outgoing laser beam detected by the outgoing laser beam monitor device 16 becomes smaller when the focusability of the laser beam is increased. Accordingly, the most suitable laser beam incident condition may be set by using the configuration and the method of the optical transmission device 1100 of the embodiment 11.

In addition, in the optical transmission device 1100 of the embodiment 11, the focusability of the laser beam can be monitored at all time.

Moreover, in the optical transmission device 1100 of the embodiment 11, although the outgoing laser beam is directly transmitted to the laser beam splitter 14, it may be acceptable to transmit the outgoing laser beam after collimating the laser beam from the optical fiber 9 by a focussing lens which is placed at the outgoing side plane of the optical fiber 9 through which the outgoing laser beam is transmitted to outside of the optical fiber 9.

EMBODIMENT 12

Figure 14:
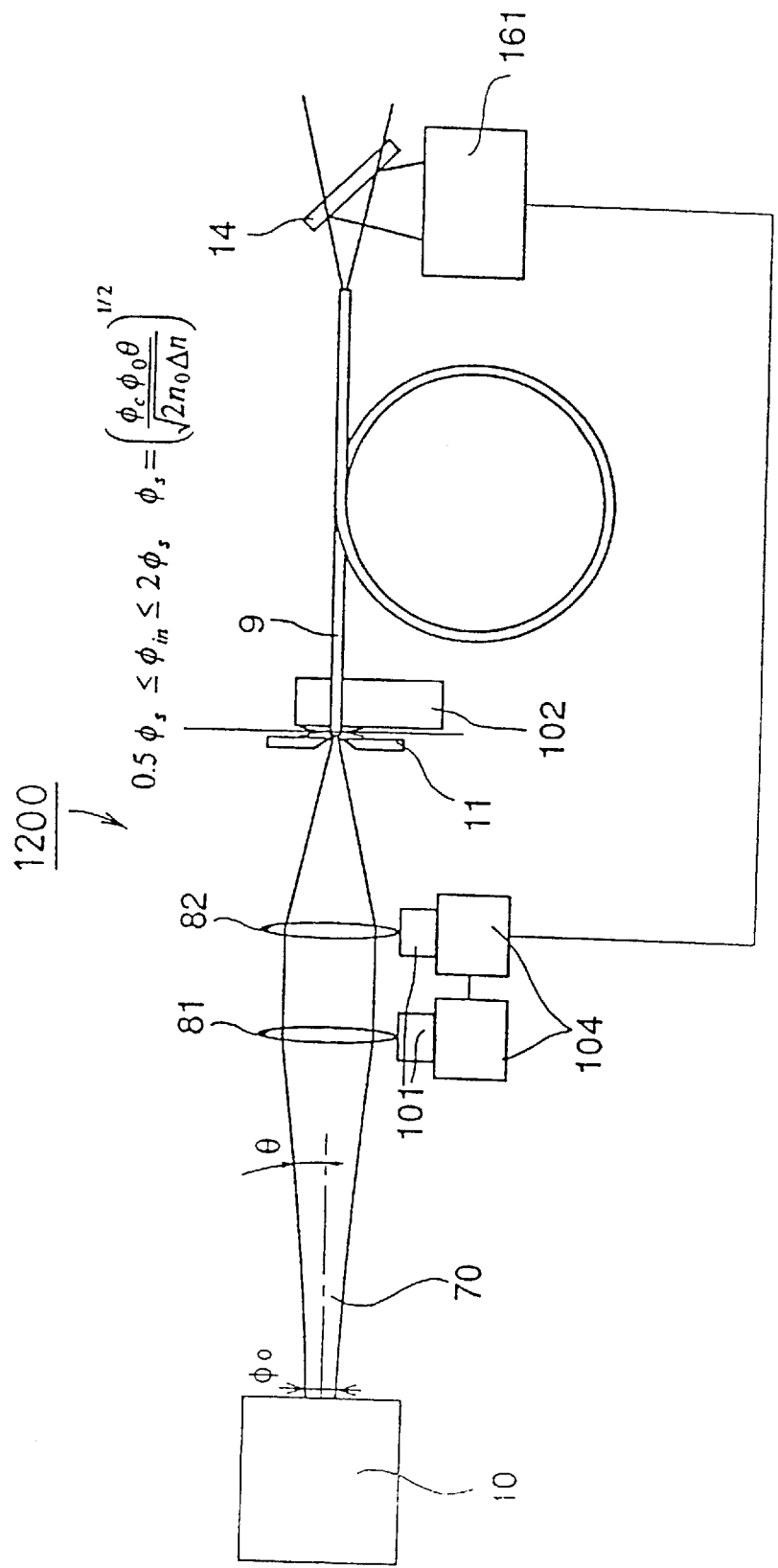
FIG. 14 is a configuration diagram showing a configuration of an optical transmission device as the embodiment 12 according to the present invention.

FIG. 14 is a configuration diagram showing a configuration of an optical transmission device 1200 of the embodiment 12 according to the present invention.

In the optical transmission device 1200 shown in FIG. 14, components which are the same components used in the optical transmission device 1100 of the embodiment 11 shown in FIG. 13 in configuration and function are referenced with the same reference numbers and the explanations for them are omitted here.

In the optical transmission device 1200 of the embodiment 12, a reference number 11 designates an aperture whose opening diameter is larger than the value $\phi_s$, sand smaller than the diameter $\phi_c$ of the core of the optical fiber 9. In addition, the center position of the opening of the aperture 11 is approximately equal to the center position of the core of the optical fiber 9. The aperture 11 is placed near the incident side plane of the optical fiber 9. A reference number 14 denotes a laser beam splitter for reflecting a part of the laser beam from the optical fiber 9, and a reference number 161 designates a power sensor.

In the optical transmission device 1200, the laser beam 70 emitted from the laser oscillator 10 having the diameter $\phi_0$ of the beam waist and the opening angle $\theta$ of the laser beam is transmitted to the focussing lenses 81 and 82 and the aperture 11, and then transmitted to the incident side plane of the optical fiber 9. The laser beam is focussed into the laser beam whose diameter is $\phi_{in}$ having a range of $0.5\phi_s$ to $2\phi_s$ by the focussing lenses 81 and 82 and irradiated onto the incident side plane of the optical fiber 9. Then, the laser beam is passed through the optical fiber 9 while keeping the focusability of the laser beam, and then transmitted to outside of the optical fiber 9. The laser beam whose optical axis is shifted from the center of the core of the optical fiber 9 is cut by the aperture 11. Most of the outgoing laser beam 70 from the optical fiber 9 is passed through the laser beam splitter 14 and other part of the outgoing laser beam is reflected by the laser beam splitter 14. The reflected laser beam by the splitter 14 is transmitted to the power sensor 161. The output data transmitted from the power sensor 161 is feed back to the optical lens holder 104 in order to adjust and move the positions of the focussing lenses 81 and 82 so that the output power of the laser beam has the maximum value.

In the optical transmission device 1200 of the embodiment 12, as clearly shown in FIG. 14, the position adjustment of the focussing lenses may be performed automatically with the simple configuration of the optical transmission device.

In addition, although it is omitted from the configuration shown in FIG. 14, it may be prevented to damage the optical fiber 9 if a feed back in order to stop the operation of the laser oscillator 10 is executed when the output power of the laser beam is decreased.

EMBODIMENT 13

Figure 15:
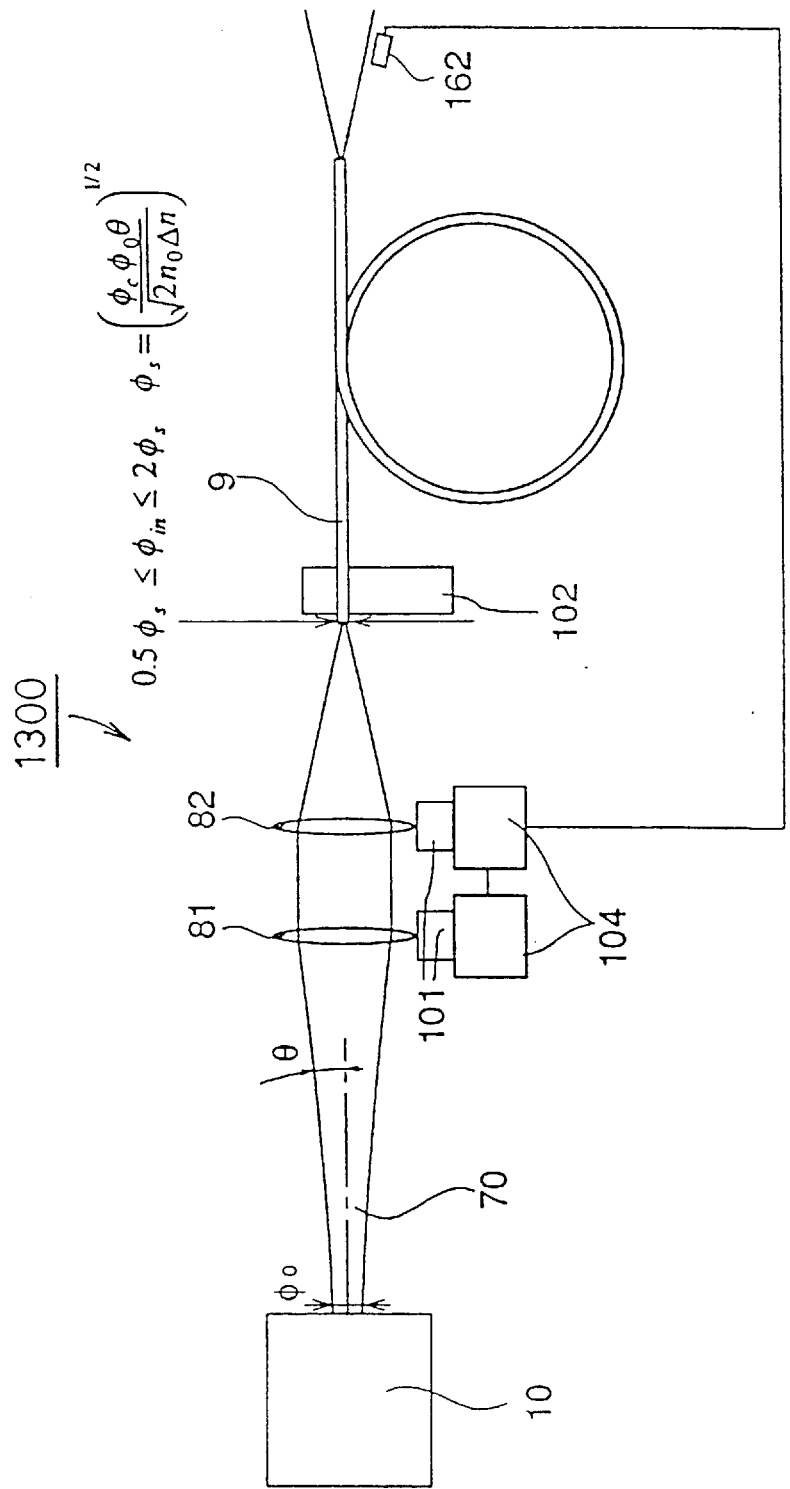
FIG. 15 is a configuration diagram showing a configuration of an optical transmission device as the embodiment 13 according to the present invention.

FIG. 15 is a configuration diagram showing a configuration of an optical transmission device 1300 of the embodiment 13 according to the present invention.

In the optical transmission device 1300 shown in FIG. 15, components which are the same components used in the optical transmission device 1100 of the embodiment 11 shown in FIG. 13 in configuration and function are referenced with the same reference numbers and the explanations for them are omitted here.

In the optical transmission device 1300 of the embodiment 13, a reference number 162 designates a photo diode placed at the position which is shifted from the optical axis of the optical fiber 9 at the outgoing side of the optical fiber 9.

In the optical transmission device 1300, the laser beam 70 emitted from the laser oscillator 10 having the diameter $\phi_0$ of the beam waist and the opening angle θ of the laser beam is transmitted to the focussing lens 81 and 82, and then transmitted to the incident side plane of the optical fiber 9 after through the focussing lenses 81 and 82. The laser beam is focussed to the laser beam whose diameter is $\phi_{in}$ having a range of $0.5\phi_s$ to $2\phi_s$ by the focussing lenses 81 and 82 and irradiated onto the incident side plane of the optical fiber 9. Then, the laser beam is passed through the optical fiber 9 while keeping the focusability of the laser beam, and then transmitted to outside of the optical fiber 9.

In this configuration of the optical transmission device 1300 shown in FIG. 15, most of the outgoing laser beam from the optical fiber 9 does not detected by the photo diode 162. However, if the incident condition to irradiate the laser beam 70 to the optical fiber 9 is different from the predetermined condition, power of the outgoing laser beam irradiated to the photo diode 162 is increased because the opening angle of the outgoing laser beam from the optical fiber 9 is enlarged. The output from the photo diode 162 is transmitted to the optical lens holder 104. The optical lens holder 104 receives the output from the photo diode 162 and adjusts and moves the position of the focussing lenses 61 and 62 so that the output of the photo diode 162 has the maximum value.

In the optical transmission device 1300 of the embodiment 13, the adjustment operation for the optical axis of the laser beam at the incident side of the optical fiber 9 may be performed with the simple configuration of the optical transmission device shown in FIG. 15.

EMBODIMENT 14

Figure 16:
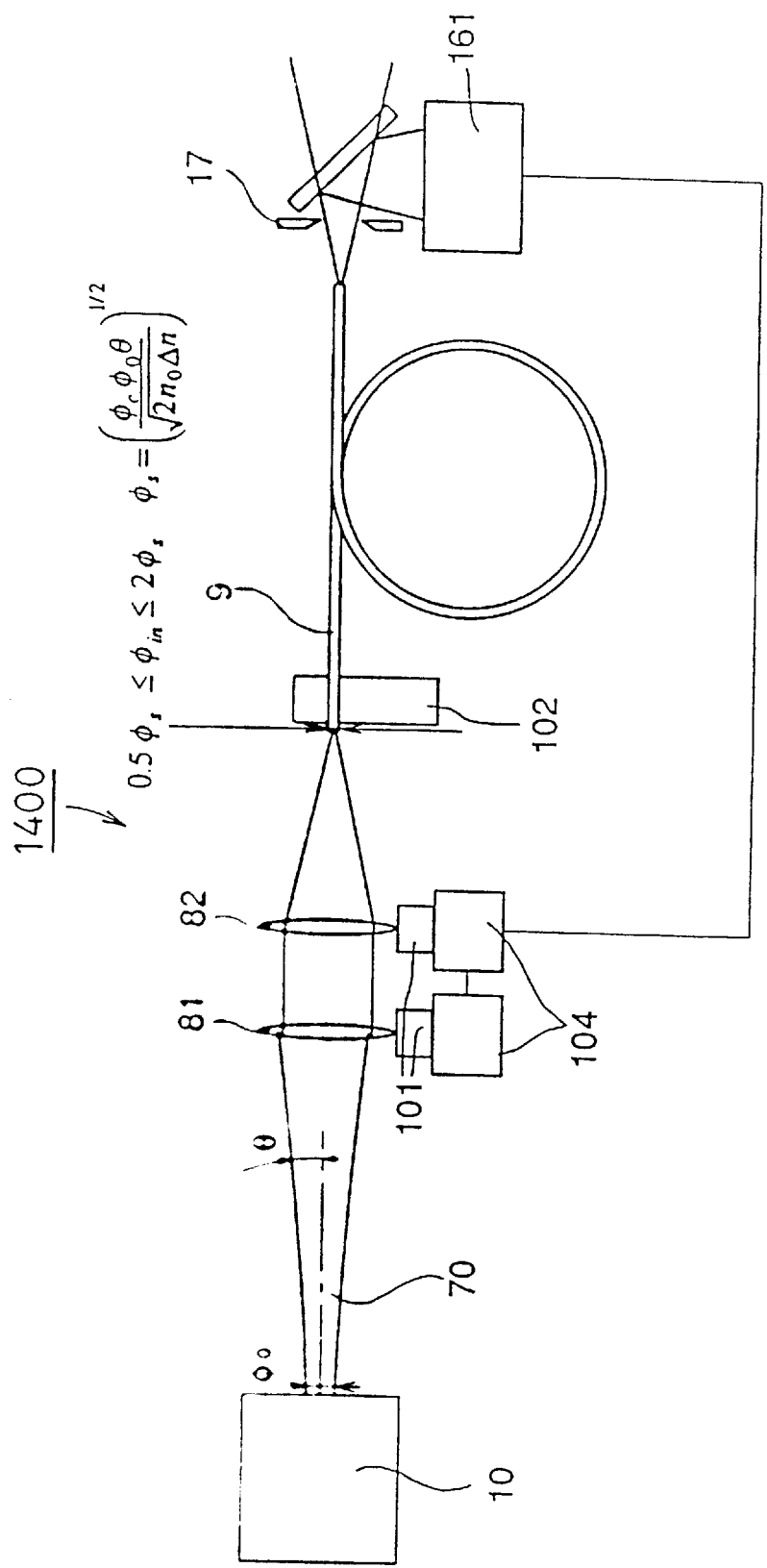
FIG. 16 is a configuration diagram showing a configuration of an optical transmission device as the embodiment 14 according to the present invention.

FIG. 16 is a configuration diagram showing a configuration of an optical transmission device 1400 of the embodiment 14 according to the present invention.

In the optical transmission device 1400 shown in FIG. 16, components which are the same components used in the optical transmission device 1100 of the embodiment 11 shown in FIG. 13 in configuration and function are referenced with the same reference numbers and the explanations for them are omitted here.

In the optical transmission device 1400 of the embodiment 14, a reference number 17 designates an aperture placed near the outgoing side of the optical fiber 9 and a reference number 161 denotes a power sensor.

The diameter of the aperture 17 is set so that the aperture 17 cuts a small amount of the laser beam from the optical fiber 9 when the laser beam 70 whose diameter is $\phi_{in}$ having a range of $0.5\phi_s$ to $2\phi_s$ is irradiated into the center of the core of the optical fiber 9.

In the optical transmission device 1400 of the embodiment 14, the magnitude of the power of the laser beam which is cut by the aperture 17 is increased because the output from the power sensor 161 is decreased when the incident position of the laser beam to the optical fiber 9 is shifted from the most suitable position.

By adjusting the position of the focussing lenses 61 and 62 by the optical lens holder 104 so that the output from the power sensor 161 has the maximum value, the laser beam diameter adjustment operation and the laser beam position adjustment operation may be performed with the simple configuration of the optical transmission device 1400 shown in FIG. 16.

EMBODIMENT 15

Figure 17:
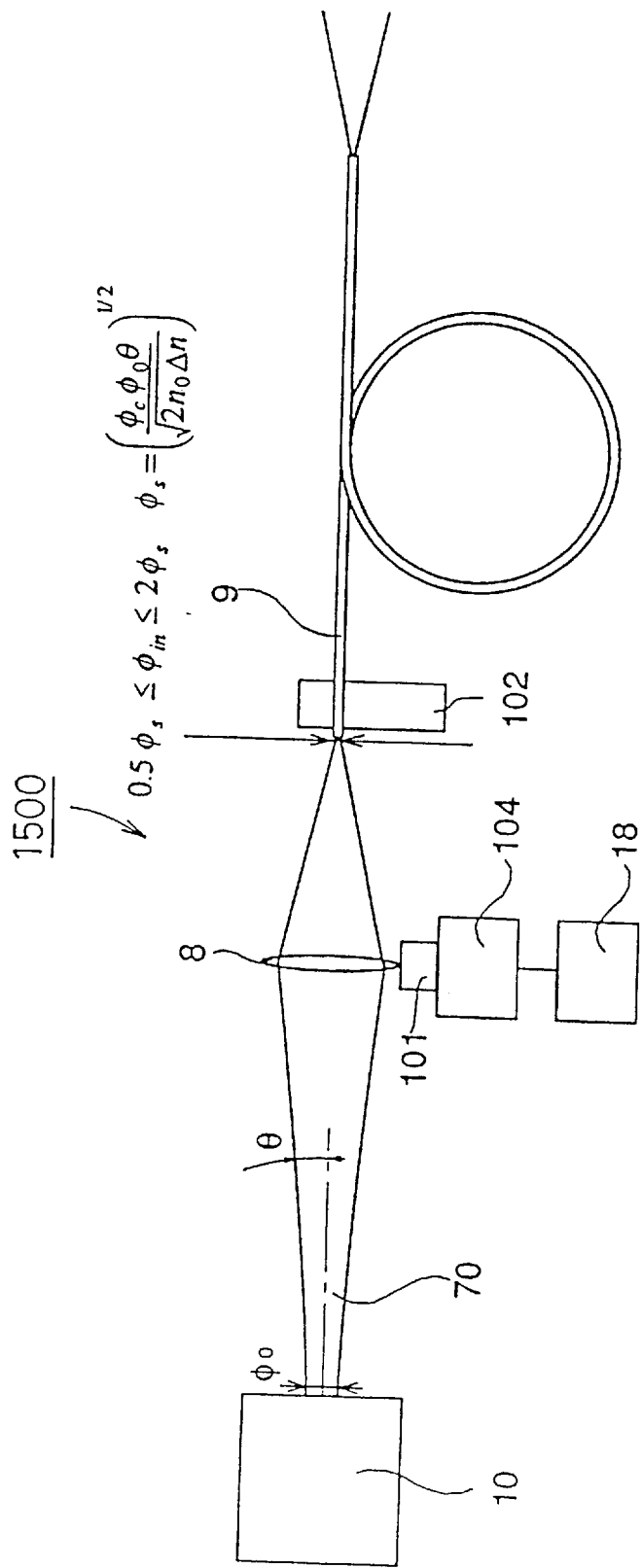
FIG. 17 is a configuration diagram showing a configuration of an optical transmission device as the embodiment 15 according to the present invention.

FIG. 17 is a configuration diagram showing a configuration of an optical transmission device 1500 of the embodiment 15 according to the present invention.

In the optical transmission device 1500 shown in FIG. 15, components which are the same components used in the optical transmission device 800 of the embodiment 8 shown in FIG. 10 in configuration and function are referenced with the same reference numbers and the explanations for them are omitted here.

In the optical transmission device 1500 of the embodiment 15 shown in FIG. 17, a reference number 18 designates a focusability setting system for setting the value M2 of the laser beam 70 by using a volume, rotating switch, a digital switch, and the like.

In the optical transmission device 1500 shown in FIG. 17, the laser beam 70 emitted from the laser oscillator 10 having the diameter $\phi_0$ of the beam waist and the opening angle θ of the laser beam is transmitted to the focussing lens 8 and transmitted to the incident side plane of the optical fiber 9 after passed through the focussing lens 8. The laser beam is focussed into the laser beam whose diameter is $\phi_{in}$ having a range of $0.5\phi_s$ to $2\phi_s$ by the focussing lens 8 and irradiated onto the incident side plane of the optical fiber 9. The laser beam 70 can be passed through the optical fiber 9 while keeping the highly focusability of the laser beam when this focussing condition of the laser beam is satisfied. However, when the optical axis of the laser beam is shifted from the center of the core of the optical fiber 9, the focusability of the laser beam is decreased.

Figure 18:
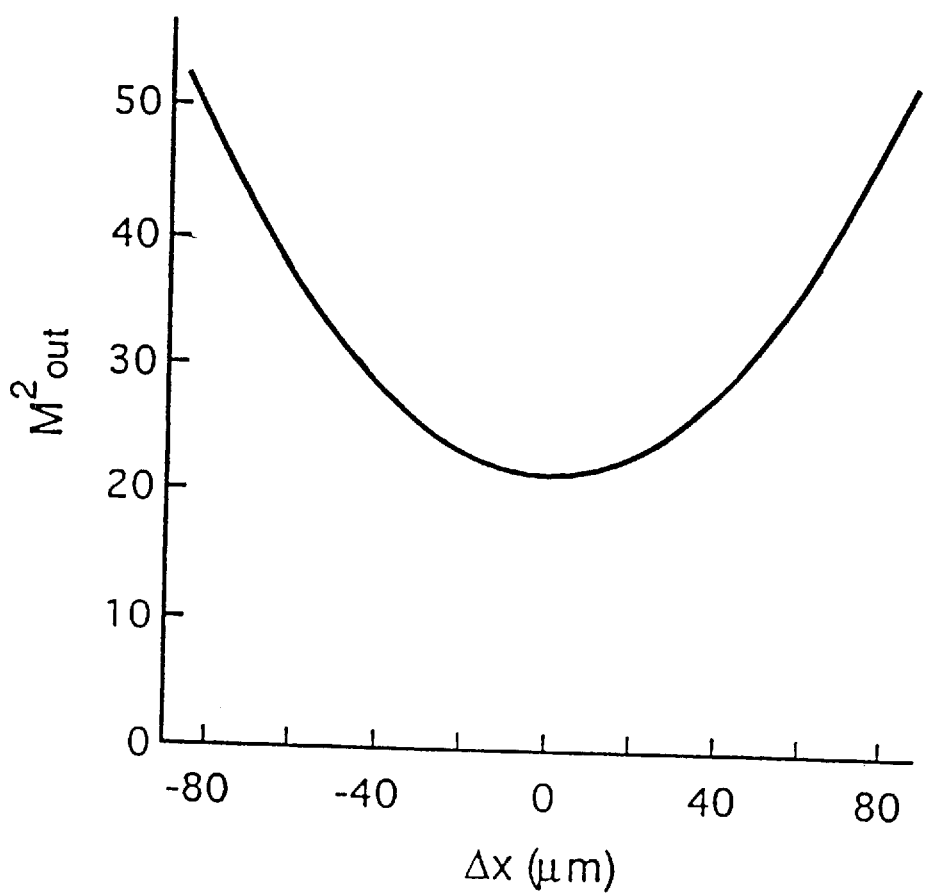
FIG. 18 is an explanately diagram showing the relationship between a shifted difference of incident displacement of a laser beam at an incident side of a graded index optical fiber and the focusability of an outgoing laser beam from the optical fiber.

FIG. 18 shows the relationship between the laser beam shifted value Δx at the incident side plane of the optical fiber 9 in the diameter direction of the core of the optical fiber 9 and the value $M^2_{out}$ of the outgoing laser beam from the optical fiber 9.

Because the value $\phi_s$ is 148 μm in this condition of the embodiment 17, all of the laser beam 70 is irradiated into the core of the optical fiber 9 even if the position of the incident laser beam is shifted by 80 μm from the center of the core of the optical fiber 9. In other word, there is no effect of the position shift of the incident laser beam and the power of the outgoing laser beam does not decreased. Thereby, it may be controlled to adjust the focusability of the laser beam by moving the position of the laser beam within a range of 80 μm. In other words, by using the value $M^2$, the laser beam having the value $M^2$ over the range of 20 to 50 may be obtained.

In the optical transmission device 1500 of the embodiment 15 shown in FIG. 17, it may be achieved to transmit the laser beam having a required focusability designated by the focusability setting system 18 from the optical fiber 9 by moving the position of the focussing lens 8 by the optical lens holder movable device 104 and the optical lens holder 101 based on the relationship between the predetermined shifted value $\Delta x$ of the laser beam and the value $M^2$ as the focusability value of the laser beam.

In the optical transmission device 1500 of the embodiment 15, the focusability of the laser beam may be changed easily in order to generate a laser beam having a most suitable power, so that the optical transmission device 1500 of the embodiment 15 may be applicable to various types processing such as welding, cutting and the like.

In the optical transmission device 1500 of the embodiment 15, we presents the relationship between the laser beam shifted value $\Delta x$ at the incident side plane of the optical fiber 9 in the diameter direction of the core of the optical fiber 9 and the value $M^2_{out}$ of the outgoing laser beam from the optical fiber 9. The value $M^2_{out}$ is changed when the minimum focussed point of the laser beam is shifted toward the optical axis direction of the optical fiber. By using this change of the value $M^2$ described above, the focussing lens 8 is shifted toward the optical axis direction of the optical fiber 9 by the optical lens holder movable device 104 and the optical lens holder 101 according to the predetermined value which has already been set in the focusability setting system 18 and the relationship between the shifted value in the predetermined axis direction and the focusability ($M^2$ value) of the outgoing laser beam so that the laser beam having the desired focusability is obtained.

In addition, in the optical transmission device 1500 of the embodiment 15, we explain the example of the laser beam which is focussed into the laser beam whose diameter $\phi_{in}$ has a range of $0.5\phi_s$ to $2\phi_s$ at or near the incident side plane of the optical fiber 9. However, the optical transmission device 1500 of the embodiment 15 is capable of applying and controlling another type of laser beam whose condition is different from the condition described above.

EMBODIMENT 16

Figure 19:
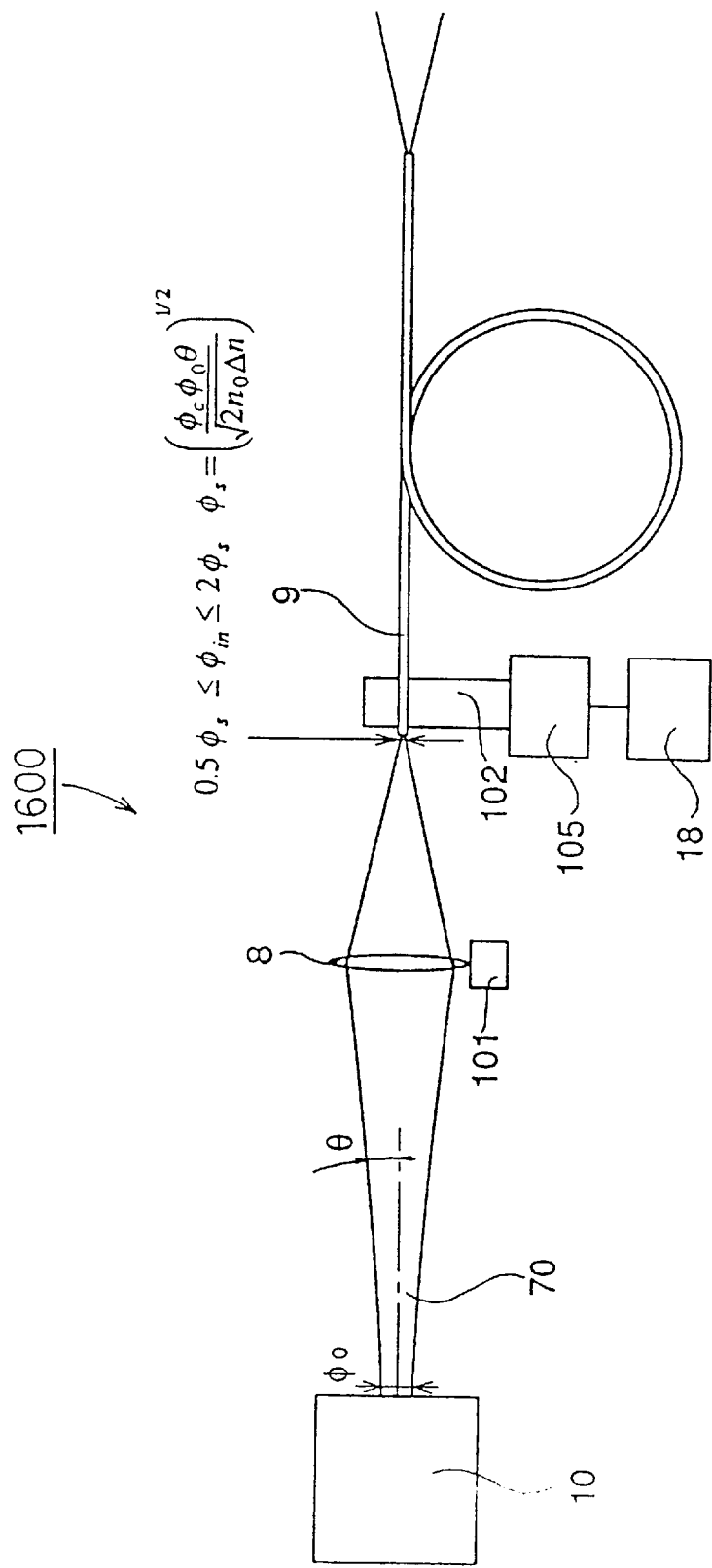
FIG. 19 is a configuration diagram showing a configuration of an optical transmission device as the embodiment 16 according to the present invention.

FIG. 19 is a configuration diagram showing a configuration of an optical transmission device 1600 of the embodiment 16 according to the present invention.

In the optical transmission device 1600 shown in FIG. 16, components which are the same components used in the optical transmission device 1500 of the embodiment 15 shown in FIG. 17 in configuration and function are referenced with the same reference numbers and the explanations for them are omitted here.

In the optical transmission device 1600 of the embodiment 16 shown in FIG. 17, a reference number 105 designates an optical fiber holder movable device. In the optical transmission device 1500 of the embodiment 15, the focussing lens 8 is moved by the optical lens holder movable device 104 and the optical lens holder 101 so that the laser beam having the required focusability indicated by the focusability setting system 18 is provided from the optical fiber 9. On the other hand, in the optical transmission device 1600, the incident side plane of the optical fiber 9 is moved by the optical fiber holder movable device 105 and the optical fiber holder 102 so that the laser beam having the required focusability indicated by the focusability setting system 18 may be also provided from the optical fiber 9. In addition, it is also acceptable to move both the focussing lens 8 and the incident side plane of the optical fiber which is the combination of the configurations of the embodiments 15 and 16 in order to control the power of the outgoing laser beam from the optical fiber 9.

EMBODIMENT 17

Figure 20:
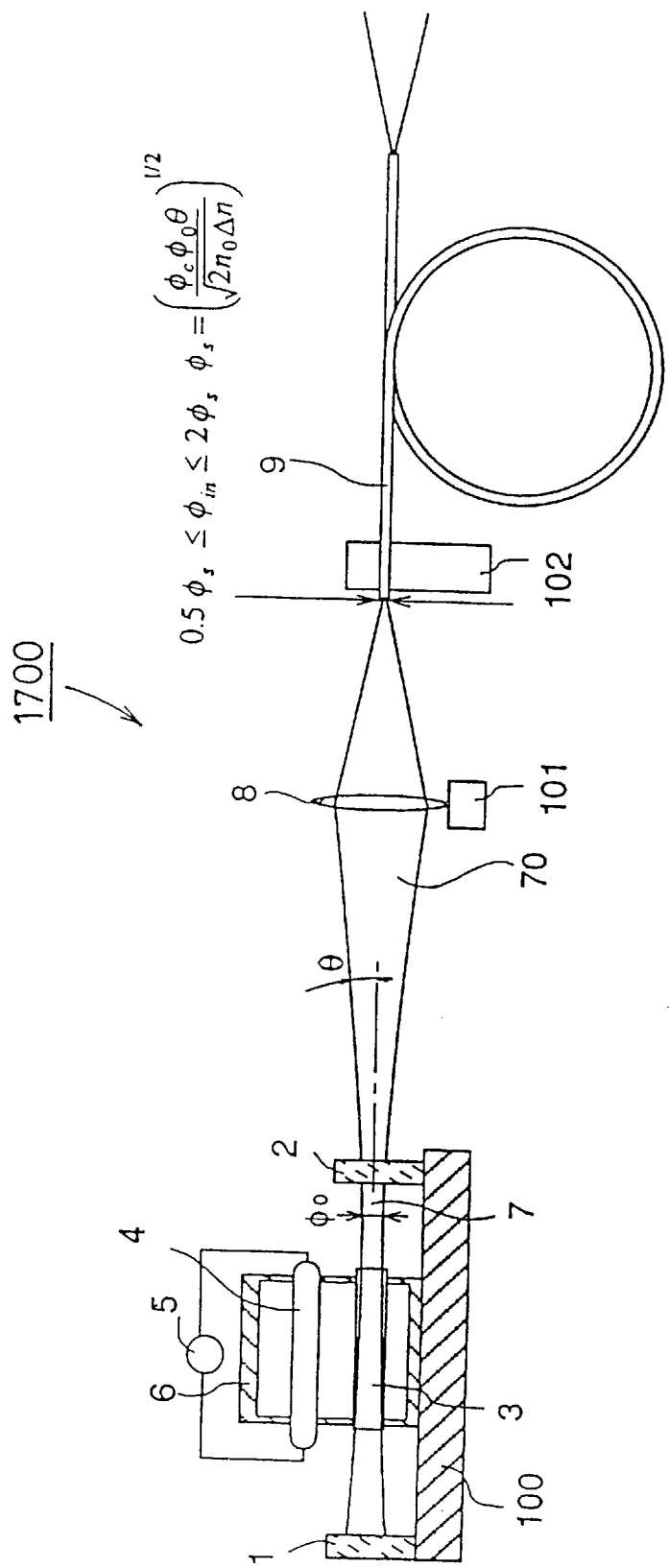
FIG. 20 is a sectional configuration diagram showing a configuration of a solid state laser device as the embodiment 17 according to the present invention.

FIG. 20 is a configuration diagram showing a configuration of a solid state laser device 1700 of the embodiment 17 according to the present invention.

In the solid state laser device 1700 shown in FIG. 20, a reference number 1 designates a total reflection mirror, a reference number 2 denotes a partial reflection mirror covered with a partial reflection coating as an output mirror, and a reference number 3 designates a solid state element having an active solid state medium, for example, the active solid state medium is Nd in YAG laser (Yttrium Aluminum Garnet laser). A reference number 4 designates a light source such as an arc lamp. A reference number 5 designates an electric power source supplying the voltage to the light source 4. A reference number 6 designates a focussing device whose sectional phase has an elliptical phase and whose internal surface comprises a light reflection plane, for example. A reference number 7 denotes a laser light generated in a laser resonator comprising the mirrors 1 and the output mirror 2. Thus, the laser resonator comprises the pair of the mirror 1 and the output mirror 2.

Other components have the same configuration and the function of the components in the optical transmission device 100 of the embodiment 1 according to the present invention. Accordingly, the explanations for other components are omitted here.

Next, the operation of the solid state laser device 1700 of the embodiment 17 having the configuration described above will be explained.

The light source 4 and the solid state element 3 are placed in the focussing device 6 whose internal surface is coated with a reflection material such as a white ceramic. When the electric power source 5 is turned on, the light from the light source 4 is directly irradiated to the solid state element 3 or is reflected by the focussing device 6 and then the reflected light is irradiated to the solid state element 3. A part of the light irradiated into the solid state element 3 is absorbed into the solid state element 3 itself. The absorbed light in the solid state element 3 excites the solid state element 3 so that the solid state element is changed to a laser medium. Spontaneous emission light generated in the laser medium is amplified between the mirror 1 and the output mirror 2 while transmitting the spontaneous emission light between the mirror 1 and the output mirror 2, and then the amplified spontaneous laser light is changed to the laser light 7. The laser light 7 is emitted, as the laser beam 70 having the diameter $\phi_0$ of the laser beam waist and the opening angle $2\theta$ of the laser beam, to the outside of the mirrors 1 and 2 in the laser resonator when the laser light 7 has more than a predetermined power. The laser beam 70 from the laser resonator is transmitted to the focussing lens 8. The laser beam passed through the focussing lens 8 is focussed into the laser beam whose diameter is $\phi_{in}$ having a range of 0.5 to $2\phi_s$ by the focussing lens 8 and irradiated onto the incident side plane of the optical fiber 9. Then, the laser beam is passed through the optical fiber 9 while keeping the focusability of the laser beam, and then transmitted to outside of the optical fiber 9.

In the explanation of the embodiment 17 described above, the output mirror 2 has a configuration wherein the output mirror 2 has a flat surface or is a mirror, the absolute value of the curvature of both surfaces of which are equal to each other, namely there is no power as the lens. However, it must be required to calculate the values $\phi_0$ and $\theta$ which are used for the calculation of the diameter of the standard laser beam at the incident side plane of the optical fiber 9 by using the distance from the focus distance f and from the output mirror 2 when the transparent characteristics of the output mirror 2 has the same characteristics of a lens whose focus distance has the value f, and the laser beam waist of the laser beam is in the laser resonant. Because these calculations are obtained by a simple optical geometric calculation, the detailed explanations for the calculations are omitted here.

By using the solid state laser device 1700 of the embodiment 17, the laser beam 70 may be transmitted through the optical fiber 9 while keeping the focusability of the laser beam 70 and provided to the outside of the optical fiber 9.

EMBODIMENT 18

Figure 21:
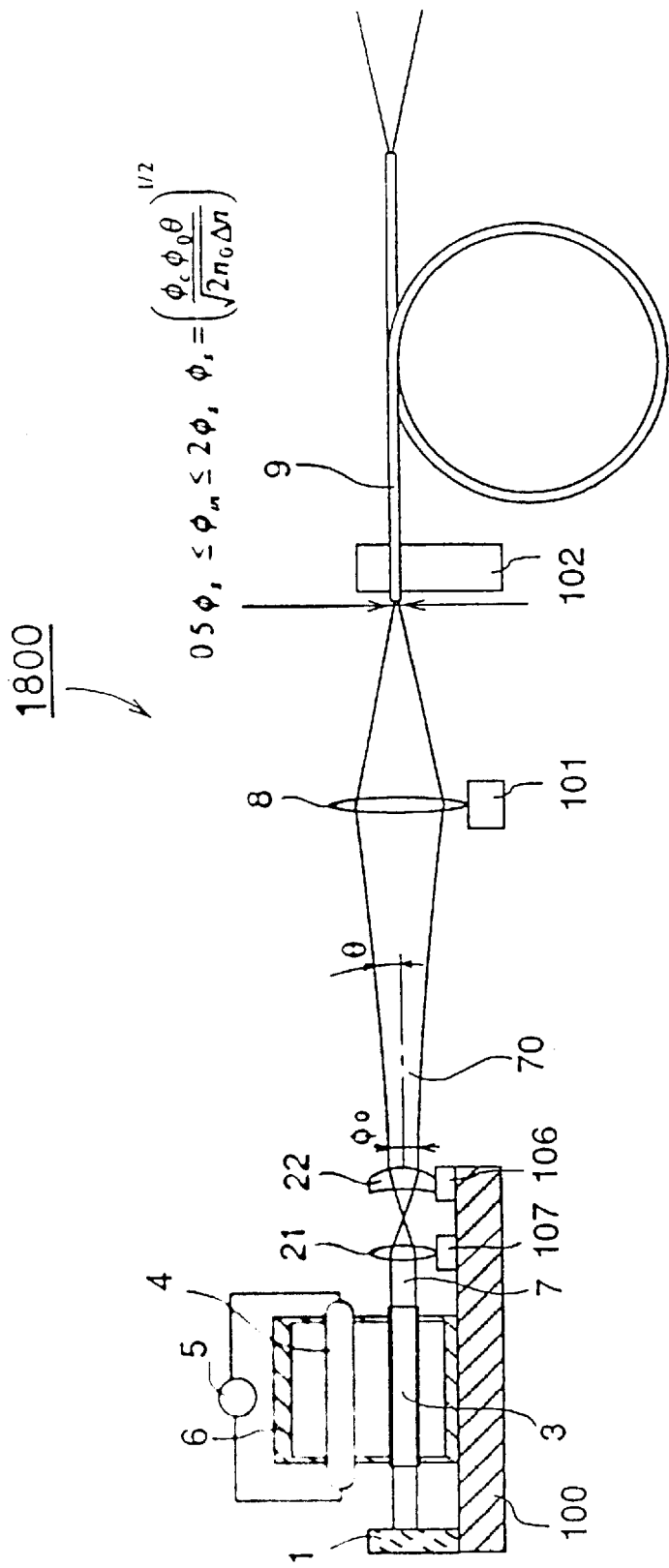
FIG. 21 is a sectional configuration diagram showing a configuration of a solid state laser device as the embodiment 18 according to the present invention.

FIG. 21 is a configuration diagram showing a configuration of a solid state laser device 1800 of the embodiment 18 according to the present invention.

In the solid state laser device 1800 shown in FIG. 21, components which are the same components used in the solid state laser device 1700 of the embodiment 17 shown in FIG. 20 in configuration and function are referenced with the same reference numbers and the explanations for them are omitted here.

In the solid state laser device 1800 of the embodiment 18 shown in FIG. 21, a reference number 21 designates a focussing lens, a reference number denotes a partial reflection mirror, and reference numbers 106 and 107 designates movable devices for moving the partial reflection mirror 22 and the focussing lens 21, respectively. In this case, the focussing lens 21 and the partial reflection mirror 22 form an image transfer optical system. In the image transfer optical system, the focus distance fr of the focussing lens 21 is as same as a curvature radius of the partial reflection mirror 22 and the distance between the focussing mirror 21 and the partial reflection mirror 22 is 2fr(1+Δ). In addition, the image transfer optical system is capable of being a changeable curvature mirror with a very wide range based on the value Δ. Accordingly, by closely and slightly adjusting the positions of the focussing lens 21 and the partial reflection mirror 22, the position of the laser beam waist and the opening angle of the laser beam can be adjusted over a very wide range. Thereby, it can be easily controlled that the diameter of the laser beam has a range of $0.5\phi_s$ to $2\phi_s$. Further, the optical fiber incident condition described above can also be kept with respect to the change of a thermal lens of the solid state medium, this change is caused when the voltage of the electric power source is changed for adjusting the magnitude of the output of the laser beam to a required value.

EMBODIMENT 19

Figure 22:
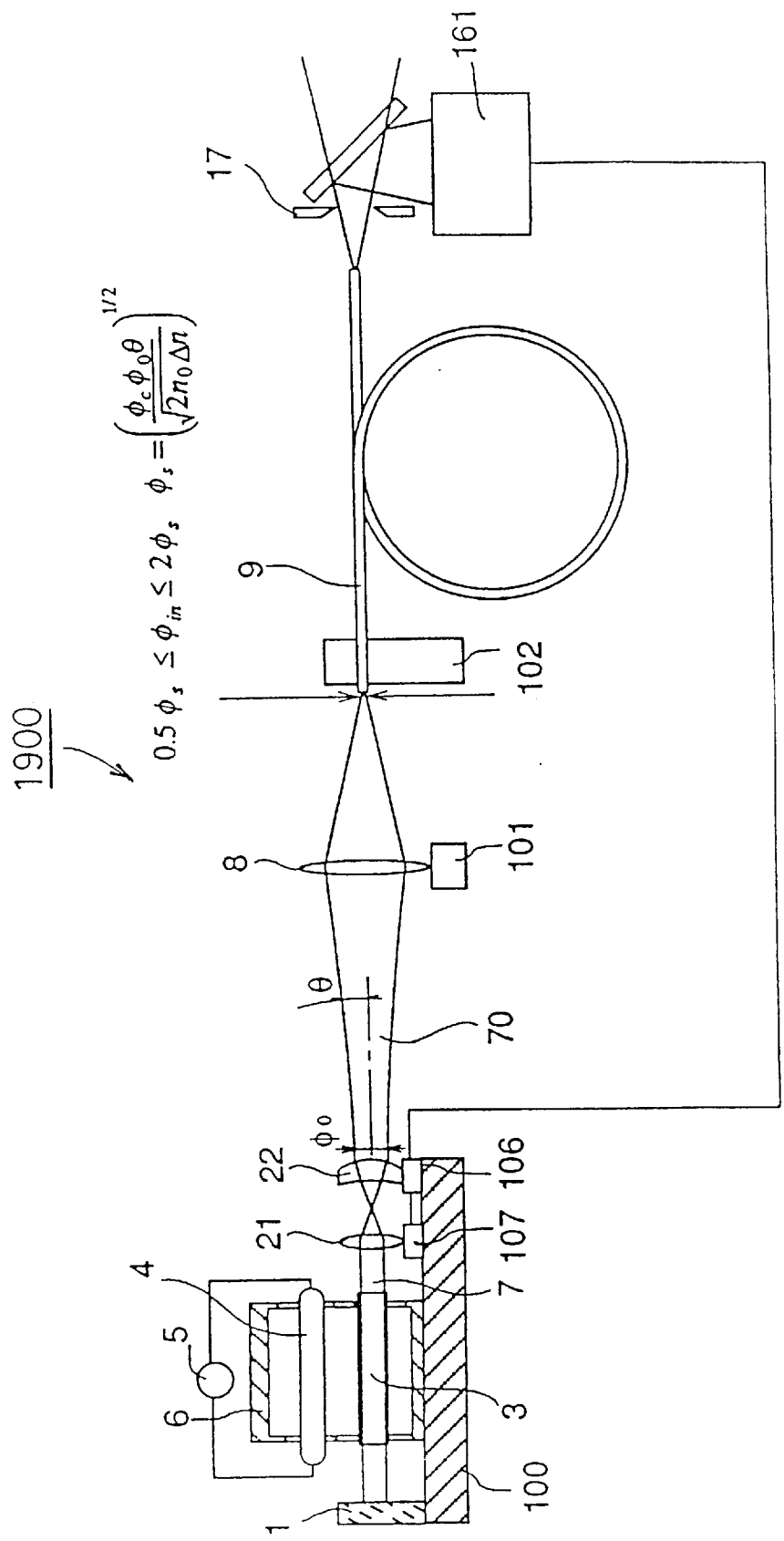
FIG. 22 is a sectional configuration diagram showing a configuration of a solid state laser device as the embodiment 19 according to the present invention.

FIG. 22 is a configuration diagram showing a configuration of a solid state laser device 1900 of the embodiment 19 according to the present invention.

In the solid state laser device 1900 shown in FIG. 22, components which are the same components used in the solid state laser device 1700 of the embodiment 17 shown in FIG. 20 in configuration and function are referenced with the same reference numbers and the explanations for them are omitted here.

In the solid state laser device 1900 of the embodiment 19 shown in FIG. 22, the aperture 17 and the power sensor 161 in the optical transmission device 1700 of the embodiment 17 shown in FIG. 16 are incorporated in addition to the image transfer optical system in the solid state laser device 1800. In the embodiment 19, the positions of both or one of the focussing lens 21 and the partial reflection mirror 22 are adjusted based on the output from the power sensor 161.

In the solid state laser device 1900 of the embodiment 19, the adjustment of the laser resonator can be performed while monitoring the actual focusability of the laser beam from the optical fiber 9. In addition, the adjustment for the position of the laser beam waist and the diameter of the laser beam can be performed certainly and automatically with respect to the change of the thermal lens of the solid state medium. Furthermore, there is an effect to monitor the focusability of the outgoing laser beam from the optical fiber at all time.

EMBODIMENT 20

Figure 23:
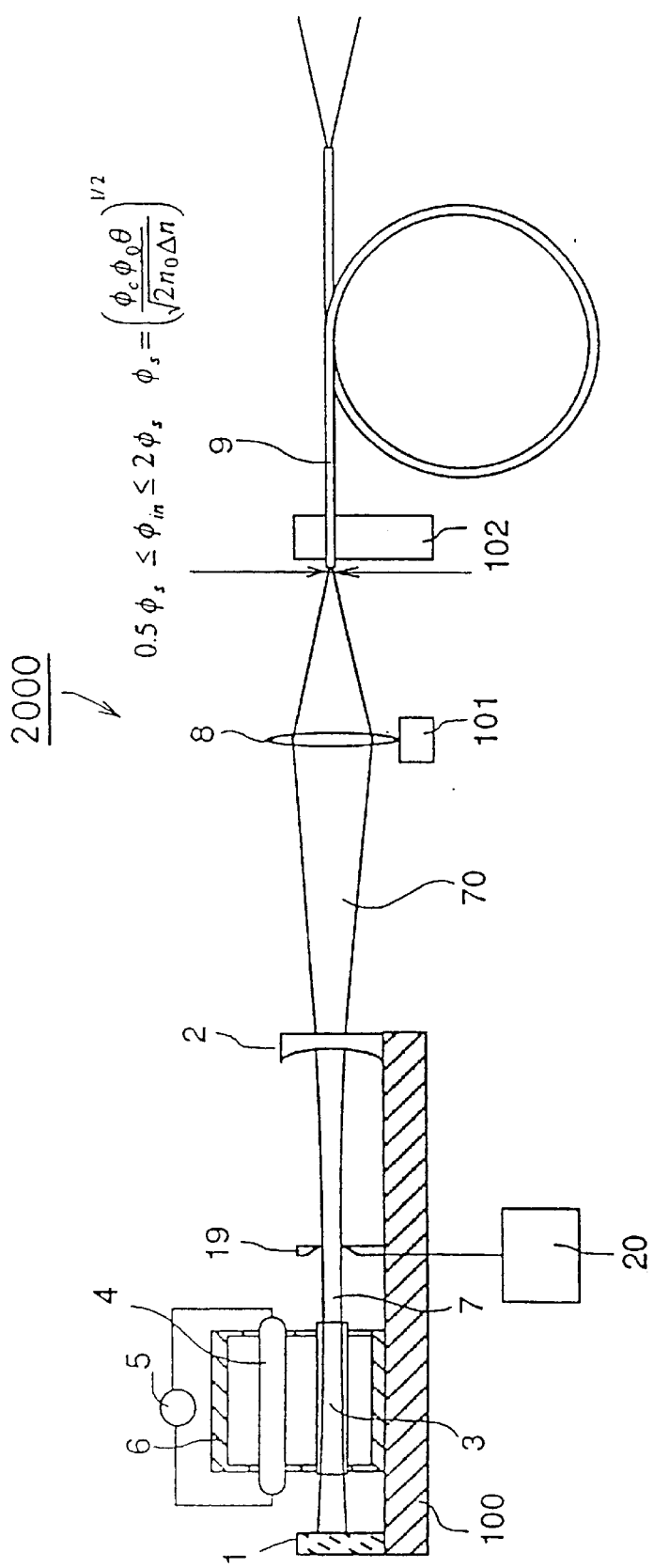
FIG. 23 is a sectional configuration diagram showing a configuration of a solid state laser device as the embodiment 20 according to the present invention.

FIG. 23 is a configuration diagram showing a configuration of a solid state laser device 2000 of the embodiment 20 according to the present invention.

In the solid state laser device 2000 shown in FIG. 23, components which are the same components used in the solid state laser device 1700 of the embodiment 17 shown in FIG. 20 in configuration and function are referenced with the same reference numbers and the explanations for them are omitted here.

In the solid state laser device 2000 of the embodiment 20 shown in FIG. 23, a reference number 19 designates an aperture, the size of the opening of which can be changed based on a control signal transmitted from outside. A reference number 20 denotes a output setting system for setting the magnitude of the laser beam output which is made up of one of a volume, a rotating switch, a digital input device and the like. The focus point and the position of the focussing lens 8 has the smallest focussed point near the incident side plane of the optical fiber 9, and the diameter of the smallest focussed point is set so that it is in a range of the value $0.5\phi_s$ to $2\phi_s$.

The adjustment of the laser beam output is performed by adjusting mechanically or electrically the diameter of the opening of the aperture 19 according to the indication from the output setting system 20. In this case, because the voltage of the electric power source 5 supplied to the lamp 4 does not change, a thermal lens effect of the solid state element is not changed. There is no change of the optical condition of the laser beam resonator except for cutting a part of the laser beam by the aperture 19, so that the position of the laser beam waist is not changed. Although the magnitude of the laser beam output, the diameter, the value $M^2$, and the opening angle of the laser beam are changed, the position of the laser beam waist and the curvature of the mirror are not changed. Under these conditions, it is known that the diameter of the laser beam and the opening angle of the laser beam are proportion to the following value:

$$\sqrt{M^2}.$$

In addition, because the image of the laser beam at the left side of the focussing lens 8 is focussed near the incident side plane of the optical fiber 9, the image position of the laser beam and the magnification of the laser beam are not changed unless the size of the laser beam waist is changed. Accordingly, the diameter of the laser beam waist near the incident side plane of the optical fiber 9 is proportion to the following value:

$$\sqrt{M^2}.$$

On the other hand, the value $\phi s$ is also proportion to the following value:

$\sqrt{M^2}$.

Therefore the laser beam 70 has always the smallest focussed point near the incident side plane of the optical fiber 9 and the diameter of the smallest focussed point has a range of the value $0.5\phi_s$ to $2\phi_s$ when the magnitude of the laser beam output is adjusted by changing the diameter of the opening of the aperture.

As described above, the solid state laser device 2000 of the embodiment 20 can supply the laser beam having a desired power passed through the optical fiber while keeping the focusability of the laser beam.

In the explanation described above, although the solid state laser device 2000 of the embodiment 20 comprises the conventional type laser beam resonator, but, the configuration of the solid state laser device 2000 can be applied to a solid state laser device having an image transfer optical system incorporated in the resonator. This case has the same effect of the solid state laser device 2000 of the embodiment 20.

EMBODIMENT 21

Figure 24:
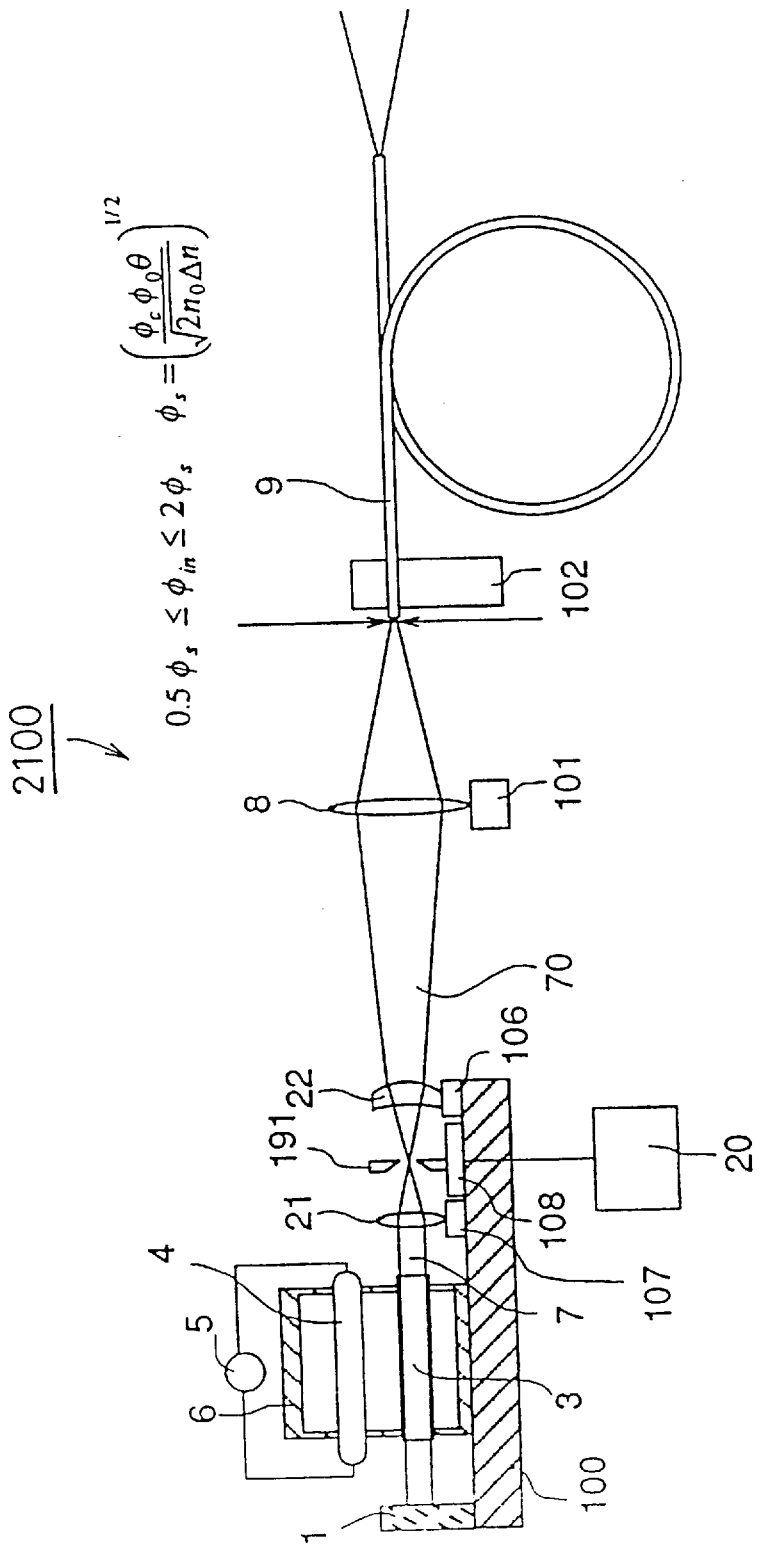
FIG. 24 is a sectional configuration diagram showing a configuration of a solid state laser device as the embodiment 21 according to the present invention.

FIG. 24 is a configuration diagram showing a configuration of a solid state laser device 2100 of the embodiment 21 according to the present invention.

In the solid state laser device 2100 shown in FIG. 24, components which are the same components used in the solid state laser device 1800 of the embodiment 18 shown in FIG. 21 in configuration and function are referenced with the same reference numbers and the explanations for them are omitted here.

In the solid state laser device 2100 of the embodiment 21 shown in FIG. 24, a reference number 191 designates an aperture which is placed between the focussing lens 21 and the partial reflection mirror 22 forming the image transfer optical system. A reference number 108 denotes an aperture movable device for moving the aperture 191 toward the optical axis direction.

The focus distance and the position of the focussing lens 8 is set so that the laser beam has the smallest focussed point near the incident side plane of the optical fiber and the diameter of the laser beam has a range of $0.5\phi_s$ to $2\phi_s$ with respect to a condition in which the solid state laser device 2100 can supply the laser beam output having the maximum power. The adjustment of the laser beam output is performed by moving the aperture 191 toward the optical axis direction of the optical fiber 9 by the aperture movable device 108 according to the indication of the output setting system 20 while shutting a peripheral region of the laser beam.

The solid state laser device 2100 of this embodiment 21, just like the solid state laser device 2000 of the embodiment 20, can supply the laser beam having a desired power passed through the optical fiber while keeping the focusability of the laser beam.

In addition, in the explanation described above, although the solid state laser device 2100 of the embodiment 21 comprises the laser beam resonator incorporating the image transfer optical system therein, it can be used for a solid state laser device incorporating a conventional type laser beam resonator and it has same effect of the solid state laser device 2100 of this embodiment 21.

EMBODIMENT 22

Figure 25:
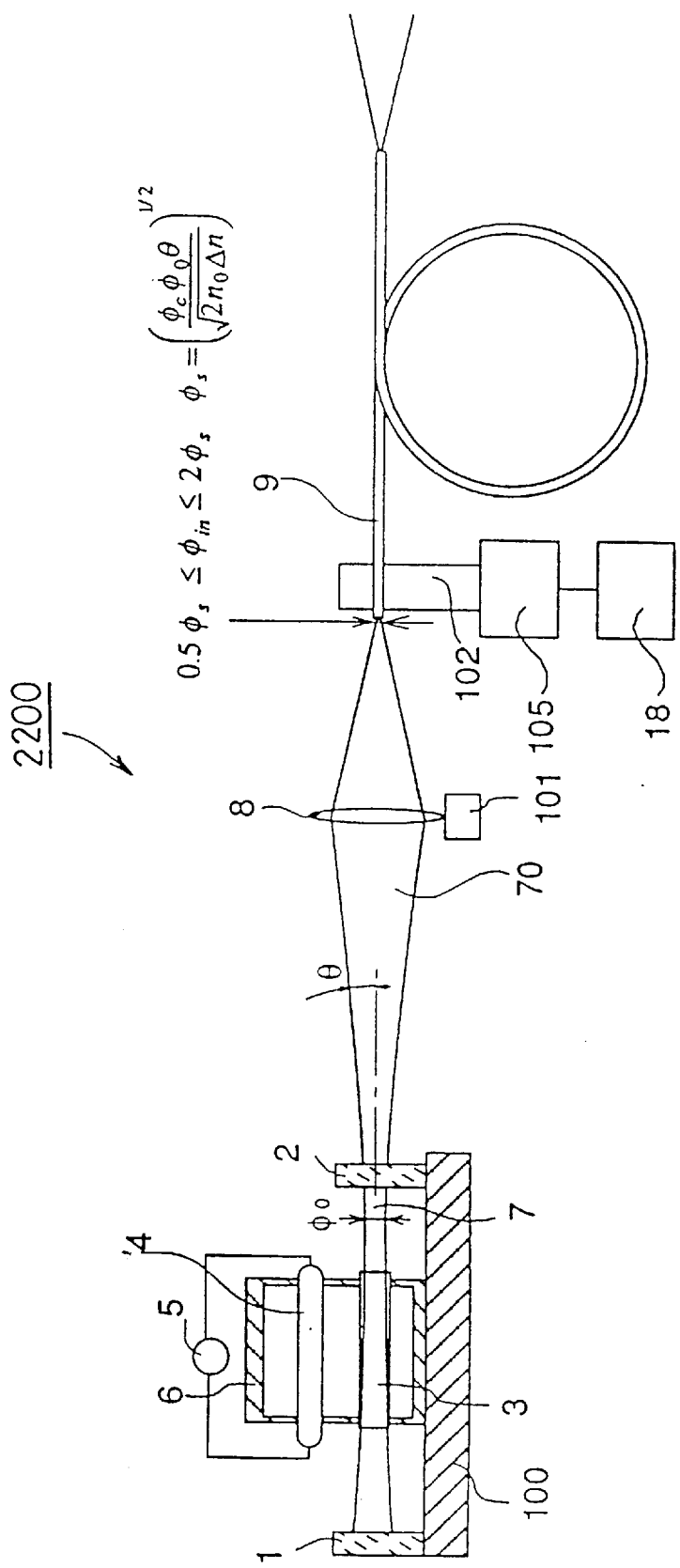
FIG. 25 is a sectional configuration diagram showing a configuration of a solid state laser device as the embodiment 22 according to the present invention.

FIG. 25 is a configuration diagram showing a configuration of a solid state laser device 2200 of the embodiment 22 according to the present invention.

In the solid state laser device 2200 shown in FIG. 25, components which are the same components used in the solid state laser device 1700 of the embodiment 17 shown in FIG. 20 in configuration and function are referenced with the same reference numbers and the explanations for them are omitted here.

In the solid state laser device 2200 of the embodiment 22 shown in FIG. 25, the light source 4 and the solid state element 3 are placed in the focussing device 6 whose internal surface is coated with a reflection material such as white ceramic. When the electric power source is turned on, the light from the light source 4 is directly irradiated to the solid state element 3 or is reflected by the focussing device 6 and then the reflected light is irradiated to the solid state element 3. A part of the light irradiated into the solid state element 3 is absorbed into the solid state element 3 itself. The absorbed light in the solid state element 3 excites the solid state element 3 so that the solid state element 3 is changed to a laser medium. Spontaneous emission light generated in the laser medium is amplified between the mirror 1 and the output mirror 2 while transferring the spontaneous emission light between the mirror 1 and the output mirror 2, and then the amplified spontaneous laser light is changed to the laser light 7. The laser light 7 is emitted, as the laser beam 70 having the diameter $\phi_0$ of the laser beam waist diameter and the opening angle $2\phi$ of the laser beam, to the outside of the mirrors 1 and 2 in the laser resonator when the laser light 7 has more than a predetermined power. The laser beam 70 from the laser resonator is transmitted to the focussing lens 8. The laser beam passed through the focussing lens 8 is focussed into the laser beam whose diameter is $\phi_{in}$ in having a range of $0.5\phi_s$ to $2\phi_s$ by the focussing lens 8 and irradiated onto the incident side plane of the optical fiber 9.

The optical fiber holder movable device 105 and the optical fiber holder 101 move the position of the incident side plane of the optical fiber 9 based on the relationship between a predetermined shift-value and the focusability of the outgoing laser beam in accordance with the value set by the focusability setting system 18 so that the solid state laser device 2200 provides the laser beam having the focusability specified by the focusability setting system 18 through the optical fiber 9.

In the solid state laser device 2200 of the embodiment 22, the focusability of the laser beam may be changed easily in order to generate a laser beam having a required power, so that the solid state laser device 2200 of the embodiment 22 may be applicable to various types processing such as welding, cutting and the like.

In addition, in the solid state laser device 2200 of the embodiment 22, the position of the incident side plane of the optical fiber 9 is changed by the optical fiber holder movable device 105, but it may be acceptable to move the position of the focussing lens 8 by using a focussing lens holder movable device which is added to the configuration of the solid state laser device 2200. In this case, the same effect can also be obtained.

Furthermore, although the conventional type laser beam resonant is used in the solid state laser device 2200 of the embodiment 22, but this invention is not limited to this, it can be applied to a solid state laser device having a laser beam resonator including an image transfer optical system or an aperture for controlling the magnitude of the laser beam. In this case, the same effect is also obtained.

EMBODIMENT 23

Figure 26:
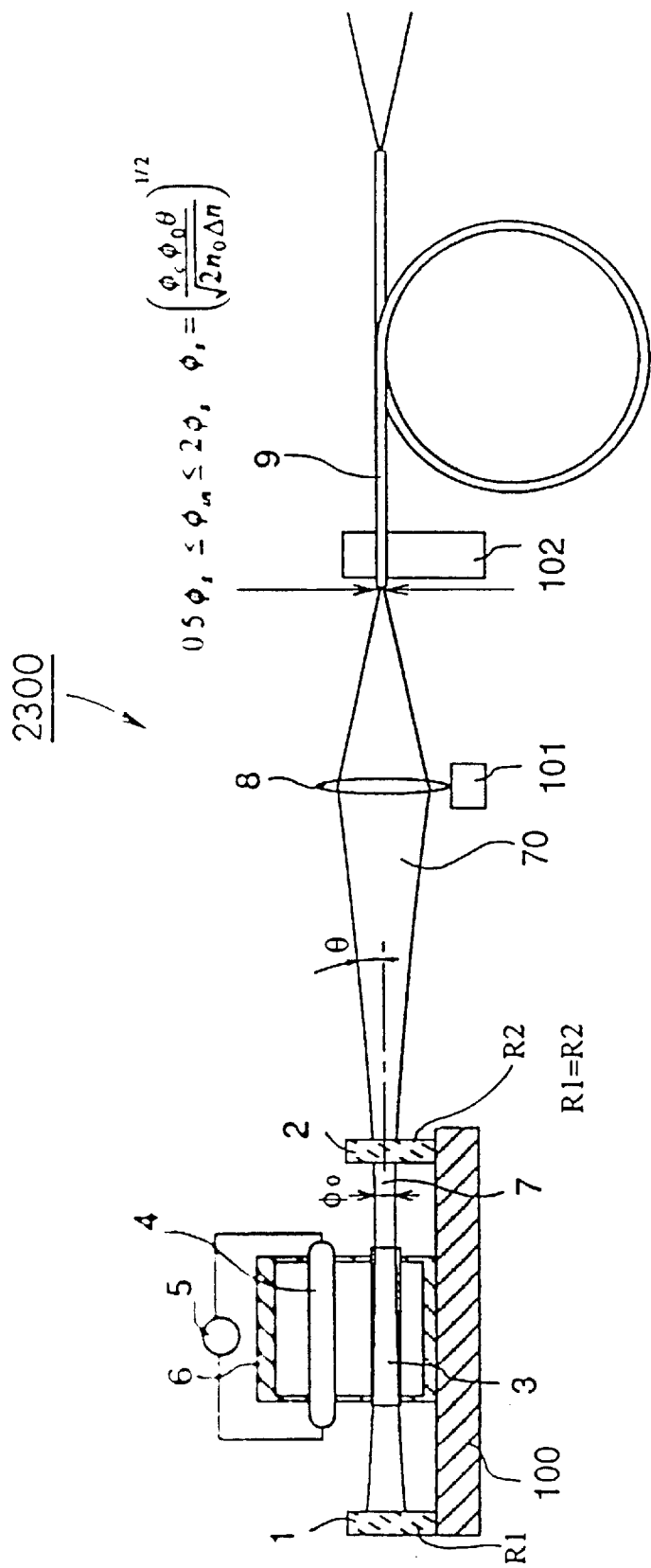
FIG. 26 is a sectional configuration diagram showing a configuration of a solid state laser device as the embodiment 23 according to the present invention.

FIG. 26 is a configuration diagram showing a configuration of a solid state laser device 2300 of the embodiment 23 according to the present invention.

In the solid state laser device 2300 shown in FIG. 26, components which are the same components used in the solid state laser device 2200 of the embodiment 22 shown in FIG. 25 in configuration and function are referenced with the same reference numbers and the explanations for them are omitted here.

In the solid state laser device 2300 of the embodiment 23 shown in FIG. 26, the total reflection mirror 1 and the output mirror 2 forming the laser resonator as a symmetrical type laser resonator, have the same curvature and the solid state element 3 is placed at approximately the intermediate point in the laser resonator.

The light source 4 and the solid state element 3 are placed in the focussing device 6 whose internal surface is coated with a reflection material such as a white ceramic. When the electric power source 5 is turned on, the light from the light source 4 is directly irradiated to the solid state element 3 or is reflected by the focussing device 6 and then the reflected light is irradiated to the solid state element 3. A part of the light irradiated into the solid state element 3 is absorbed into the solid state element 3 itself. The absorbed light in the solid state element 3 excites the solid state element 3 so that the solid state element 3 is changed to a laser medium. Spontaneous emission light generated in the laser medium is amplified between the mirror 1 and the output mirror 2 while transferring the spontaneous emission light between the mirror 1 and the output mirror 2, and then the amplified spontaneous laser light is changed to the laser light 7. The laser light 7 is emitted, as the laser beam 70 having the diameter $\phi_0$ of the laser beam waist diameter and the opening angle $2\theta$ of the laser beam, to the outside of the mirrors 1 and 2 in the laser resonator when the laser light 7 has more than a predetermined power.

Although the solid state laser device 2600 having the configuration described above can perform a very stable laser beam oscillating operation, it also has a feature of greatly changing the diameter and the opening angle of the laser beam according to the magnitude of the laser beam output. In this case, the value $\phi_0\theta$ and the value $M^2$ of the laser beam which is proportion to the value $\phi_0\theta$ is also changed greatly.

Figure 27:
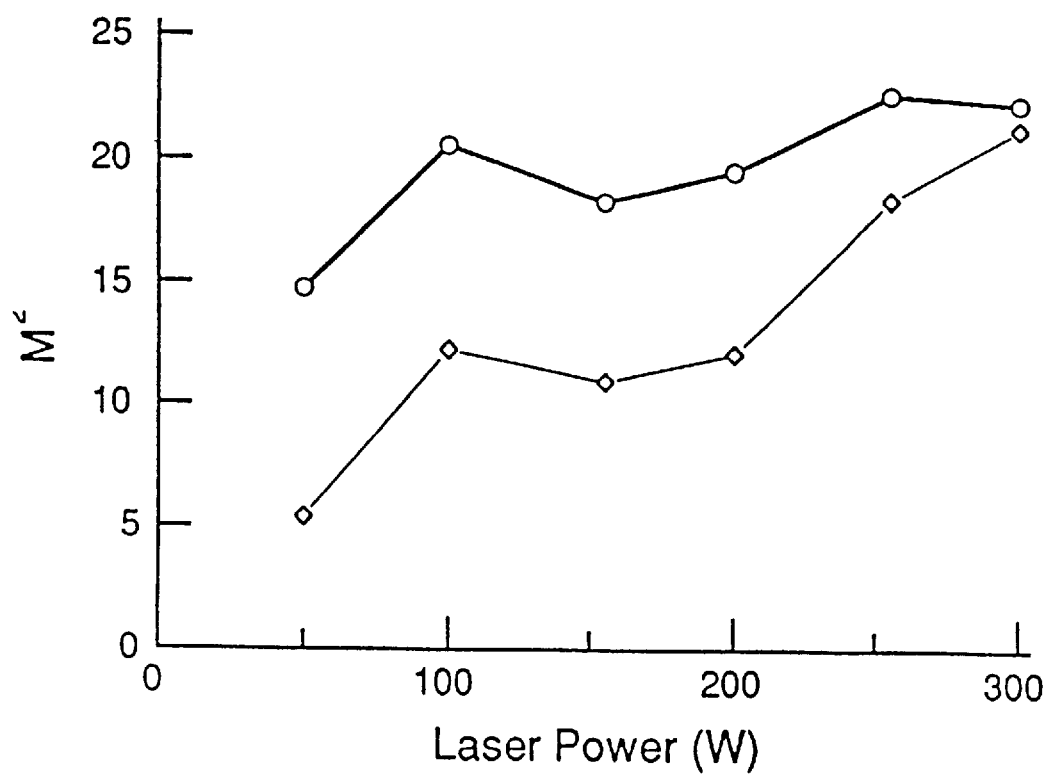
FIG. 27 is an explanately diagram showing the relationship between the M² value of an outgoing laser beam and an incident laser beam in the solid state laser device of the embodiment 23 shown in FIG. 26 according to the present invention.

FIG. 27 is a diagram showing the relationship between the laser beam output and the value $M^2$ of the laser beam in a solid state laser derive having a symmetrical resonator configuration with a thin line. When the magnitude of the laser beam output becomes smaller, the laser beam having the smaller value $M^2$ is generated. Thereby, it is apparently that the diameter of the laser beam for propagation is different corresponding to the magnitude of the laser beam output. In the solid state laser device 2300 of the embodiment 23, the laser beam 70 from the laser resonator is focused into a laser beam having the smallest focussed point near the incident side plane of the optical fiber 9 and having the diameter of the laser beam is the value: $0.5\phi_c\phi_0\theta(2n_0\Delta n)^{-1/2})^{1/2}$ to $2(\phi_c\phi_0\phi(2n_0\Delta n)^{-1/2})^{1/2}$ by the focussing lens 8 on the basis of the value $\phi_0\theta$ of the laser beam output 300 Watts which is the most largest $M^2$, not by moving the optical system in the magnitude of another laser beam output.

In the solid state laser device 2300 of the embodiment 23, the value $M^2$ of the laser beam after propagation is increased corresponding to the change of the laser beam diameter and the like when the laser beam output is not 300 W. However, the change of the value $M^2$ caused by the laser beam output is decreased because the value of $M^2$ of the original laser beam emitted from the laser resonator is smaller than 300 Watts, so that the solid state laser device can provide the laser beam having a stable focusability.

In FIG. 27, the solid line shows an experimental result of the propagation of the laser beam with the value $\phi_0\theta$ when the power of the laser beam is 300 Watts designated by the thin line, while adjusting the diameter of the incident laser beam 70 to the optical fiber 9. In FIG. 27, the change of the $M^2$ of the incident laser beam has the range of 5 to 22. On the other hand, the value $M^2$ of the outgoing laser beam from the optical fiber 9 has the range of 15 to 22. Accordingly, even if the output of the laser beam from the laser resonator is changed, we can provide the outgoing laser beam having a stable focusability by using the solid state laser device 2300 of the embodiment 23.

EMBODIMENT 24

Figure 28A:
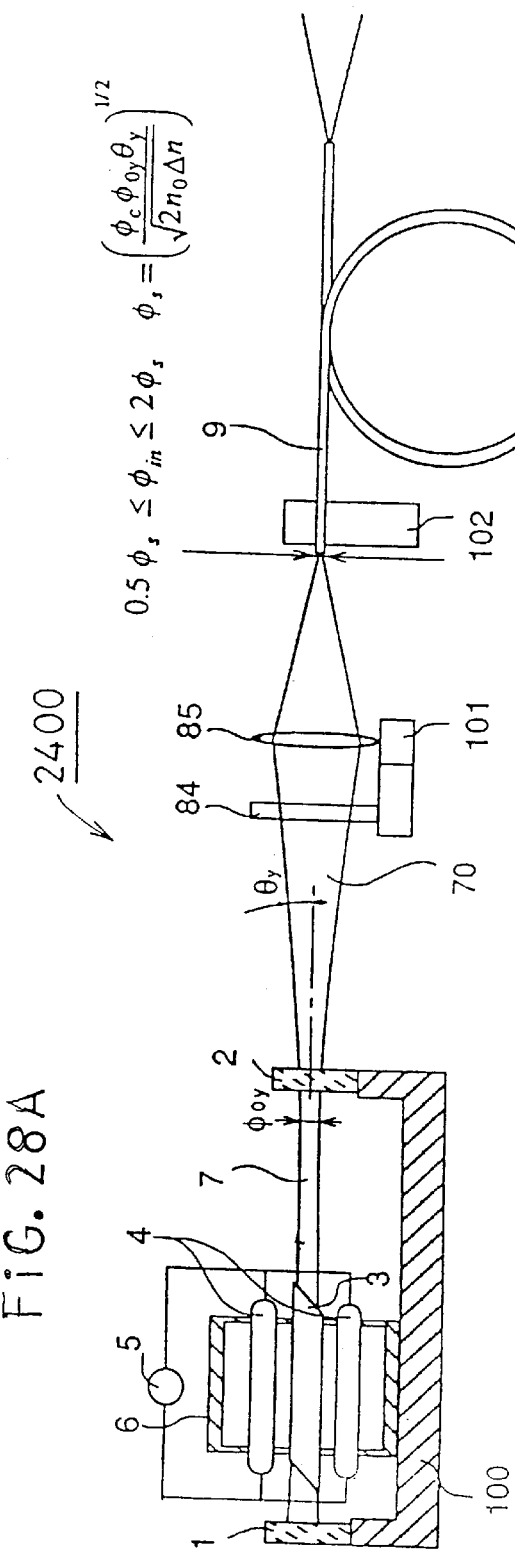
FIGS. 28A and 28B are configuration diagrams showing a configuration of a solid state laser device of the embodiment 24 according to the present invention.
Figure 28B:
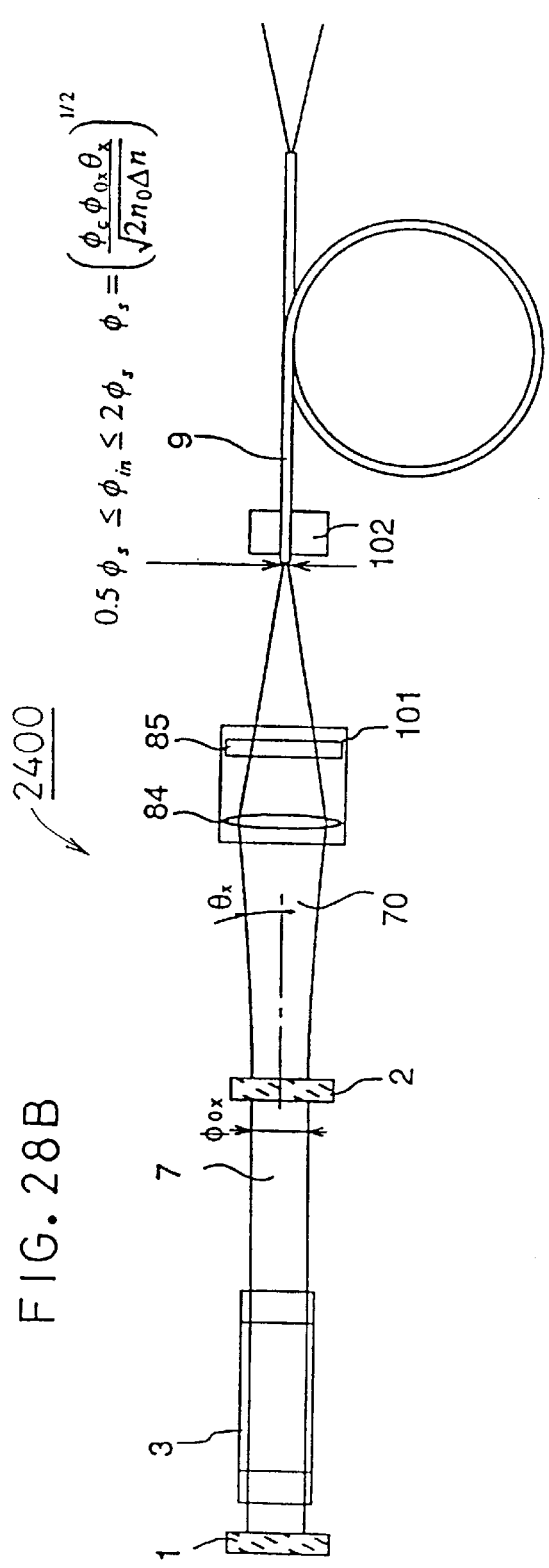

FIGS. 28A and 28B are a configuration diagram showing a configuration of a solid state laser device 2400 of the embodiment 24 according to the present invention. FIG. 28B is a plan view of the solid state laser device 2400 shown in FIG. 28A.

In the solid state laser device 2400 shown in FIGS. 28A and 28B, components which are the same components used in the solid state laser devices 2200 and 2300 of the embodiments 22 and 23 shown in FIGS. 25 and 26 in configuration and function are referenced with the same reference numbers and the explanations for them are omitted here.

In the solid state laser device 2400 of the embodiment 24 shown in FIGS. 28A and 28B, the solid state element 3 comprises a slab laser medium having a thin plate form. Because the slab laser medium has different values $\phi_{0x}\theta_x$ and $\phi_{0y}\theta_y$ in the X axis direction and the Y axis direction, respectively, these values $\phi_{0x}\theta_x$ and $\phi_{0y}\theta_y$ are greatly different to each other in the X axis direction and the Y axis direction when the laser reasoner comprises a usual spherical lens.

In the solid state laser device 2400 of the embodiment 24, laser beam components in the X axis direction and the Y axis direction are focussed independently by using cylindrical lenses. Specifically, the laser beam 70 from the laser resonator is focussed so that the component of the laser beam in the X axis direction has the smallest focussed point near the incident plane of the optical fiber and whose diameter has a range of $0.5(\phi_c\phi_{0x}\theta_x(2n_0\Delta n)^{-1/2})^{1/2}$ to $2(\phi_c\phi_{0x}\phi_x(2n_0\Delta n)^{-1/2})^{1/2}$ by the cylindrical lens 84, and the component of the laser beam in the Y axis direction has the smallest focussed point near the incident plane of the optical fiber and whose diameter has a range of $0.5(\phi_c\phi_{0x}\theta_x(2n_0\Delta n)^{-1/2}\ ^{1/2})$ to $2(\phi^c\phi_{0y}\phi_y(2n_0\Delta n)^{-1/2}\ ^{1/2}$ by the cylindrical lens 85.

In the solid state laser device 2400 of the embodiment 24, the value $M^2$ of the outgoing laser beam from the optical fiber 9 has a value between the value $M^2$ of the component of the incident laser beam in the X axis direction and the value $M^2$ in the Y axis direction. Accordingly, the solid state laser device for supplying a laser beam having a stable focusability can be provided even if the solid state laser device including the laser resonator having different focusability to each other in the X axis direction and the Y axis direction. In addition, the solid state laser device has another effect that during the propagation of the laser beam in the solid state laser device, the anisotropy of the laser beam can be improved.

EMBODIMENT 25

FIGS. 29A and 29B are a configuration diagram showing a configuration of a solid state laser device 2500 of the embodiment 25 according to the present invention. FIG. 29B is a plan view of the solid state laser device 2500 shown in FIG. 29A.

In the solid state laser device 2500 shown in FIGS. 29A and 29B, components which are the same components used in the solid state laser devices 2200, 2300, and 2400 of the embodiments 22, 23 and 24 shown in FIGS. 25, 26, 28A and 28B in configuration and function are referenced with the same reference numbers and the explanations for them are omitted here.

In the solid state laser device 2500 of the embodiment 25 shown in FIGS. 29A and 29B, the solid state element 3 comprises a slab laser medium, having a thin plate f, and the laser resonator is made up of a hybrid type laser resonator in which the X axis direction is stable and the Y axis direction is unstable. It is well known that this type laser resonator can generates a laser beam having a highly focusability theoretically. However, in general, the unstable type laser resonator can generate a laser beam with a more highly focusability. In this case, the value $\phi_{0x}\theta_x$ of the laser beam in the X axis direction is different from the value $\phi_{0y}\theta_y$ in the Y axis direction, so that the following relationship is obtained:

$$\phi_{0x}\theta_x < \phi_{0y}\theta_y.$$

In the solid state laser device 2500 of the embodiment 25, like the solid state laser device 2400 of the embodiment 24 described above, laser beam components in the X axis direction and the Y axis direction are focussed independently by using the cylindrical lenses. Specifically, the laser beam 70 from the laser resonator is focussed so that the component of the laser beam in the X axis direction has the smallest focussed point near the incident plane of the optical fiber and whose diameter has a range $(\phi_c\phi_{0x}\theta_x (2n_0\Delta n)^{1/2})^{1/2} \pm 50\%$ by the cylindrical lens 84, and the component of the laser beam in the Y axis direction has the smallest focussed point near the incident plane of the optical fiber and whose diameter has a range $0.5_c\phi_{0y}\theta_y(2n_0\Delta n)^{-1/2})^{1/2}$ to $2(\phi_c\phi_{0y}\theta_y(2n_0\Delta n)^{1/2})^{1/2}$ by the cylindrical lens 85.

In the solid state laser device 2500 of the embodiment 25, like the solid state laser devices 2300 and 2400 of the embodiments 23 and 24 described above, the value $M^2$ of the outgoing laser beam from the optical fiber 9 has a value between the value $M^2$ of the component of the incident laser beam in the X axis direction and the value $M^2$ in the Y axis direction. Accordingly, the solid state laser device for supplying a laser beam having a stable focusability can be provided.

EMBODIMENT 26

FIGS. 30A and 30B are a configuration diagram showing a configuration of a solid state laser device 260 of the embodiment 26 according to the present invention. FIG. 30B is a plan view of the solid state laser device 2600 shown in FIG. 30A.

In the solid state laser device 2600 shown in FIGS. 30A and 30B, components which are the same components used in the solid state laser devices 2200, 2300, 2400, and 2500 of the embodiments 22, 23, 24, and 25 shown in FIGS. 25, 26, 28A, 28B, 29A, and 29B in configuration and function are referenced with the same reference numbers and the explanations for them are omitted here.

In the solid state laser device 2600 of the embodiment 26 shown in FIGS. 30A and 30B, the solid state element 3 comprises a slab laser medium as the hybrid type laser resonator. The component in the X axis direction of the laser beam is focussed on the incident side plane of the optical fiber 9 by using a usual spherical lens, and the component in the Y axis direction of the laser beam is focussed so that this component has the smallest focussed point near the incident plane of the optical fiber and whose diameter has a range of $0.5(\phi_c\phi_{0y}\phi_y(2n_0\Delta n)^{-1/2})^{1/2}$ to $2(\phi_c\phi_{0y}\phi_y(2n_0\Delta n)^{1/2})^{1/2}$. In this case, it will be predicted that the position and the diameter of the smallest focussed point in the X axis direction are very shifted from the most suitable values. However, the relationship $\phi_{0x}\phi_x < \phi_{0y}\theta_y$ is satisfied in the laser resonator in the solid state laser device 2600 and the value $M^2$ of the outgoing laser beam is taken between the $M^2$ values in the X axis direction and the Y axis direction. Accordingly, even if the $M^2$ value of the X axis direction is slightly shifted from the most suitable value, the magnitude of the value $M^2$ of the outgoing laser beam in the X axis direction is not more than that in the Y axis direction, so that on the total outgoing laser beam has the superior highly focusability while propagating.

The solid state laser device 2600 which is capable of keeping the highly focusability during propagation as the embodiment 26 can be provided with the very simple configuration as shown in FIGS. 30A and 30B even though the solid state laser device has a laser resonator whose focusability is different in the X axis direction and the Y axis direction. In addition, the solid state laser device has another effect that during the propagation of the laser beam in the solid state laser device, the anisotropy of the laser beam can be improved.

EMBODIMENT 27

FIG. 31 is a configuration diagram showing a configuration of a laser processing device 2700 of the embodiment 27 according to the present invention.

In the laser processing device 2700 shown in FIG. 31, components which are the same components used in the optical transmission device 100 of the embodiment 1 shown in FIG. 1 in configuration and function are referenced with the same reference numbers and the explanations for them are omitted here.

In the laser processing device 2700 of the embodiment 27 shown in FIG. 31, a reference number 23 designates a focussing lens, a reference number 80 denotes a target work to be processed by irradiating a laser beam from the laser processing device 2700, a reference number 810 designates a processing nozzle, and a reference number 820 denotes an introduction inlet for a processing gas. In the laser processing device 2700 of the embodiment 27, the laser beam 70 emitted from the laser oscillator 10 having the diameter $\phi_0$ of the beam waist and the opening angle θ of the laser beam is transmitted to the focussing lens 8 and focussed to the laser beam whose diameter is $\phi_{in}$ having a range of $0.5\phi_s$ to $2\phi_s$ and irradiated onto the incident side plane of the optical fiber 9. Then, the laser beam is passed through the optical fiber 9 while keeping the focusability of the laser beam, and then transmitted to outside from the outlet of the optical fiber 9. The outgoing laser beam is focussed by the focussing lens 23. The target work is processed by using the focussed laser beam.

Thus, the laser processing device can provide a highly focussed laser beam than the laser beam from the optical fiber 9 for high accuracy laser processing operation because the laser beam from the optical fiber 9 s further focussed by the focussing lenses 23.

In the laser processing device 2700 of the embodiment 27, the optical transmission device 100 of the embodiment 1 as shown in FIG. 1 is used, but the scope of the present invention is not limited by this, it may be acceptable and it may get the same effect by incorporating the optical transmission devices 1400, 1700, and 2100 of the embodiments 14, 17, and 21 as shown in FIGS. 16 20, and 21.

EMBODIMENT 28

FIG. 32 is a configuration diagram showing a configuration of a laser processing device 2800 of the embodiment 28 according to the present invention.

In the laser processing device 2800 shown in FIG. 32, components which are the same components used in the solid state laser device 2200 of the embodiment 22 shown in FIG. 25 in configuration and function are referenced with the same reference numbers and the explanations for them are omitted here.

In the laser processing device 2800 of the embodiment 28 shown in FIG. 32, the light source 4 and the solid state element 3 are placed in the focussing device 6 whose internal surface is coated with a reflection material such as white ceramic. When the electric power source 5 is turned on, the light from the light source 4 is directly irradiated to the solid state element 3 or is reflected by the focussing device 6 and then the reflected light is irradiated to the solid state element 3. A part of the light irradiated into the solid state element 3 is absorbed into the solid state element 3 itself. The absorbed light in the solid state element 3 excites the solid state element 3 so that the solid state element 3 is changed to a laser medium. Spontaneous emission light generated in the laser medium is amplified between the mirror 1 and the output mirror 2 while transferring the spontaneous emission light between the mirror 1 and the output mirror 2, and then the amplified spontaneous laser light is changed to the laser light 7. The laser light 7 is emitted, as the laser beam 70 having the diameter $\phi_0$ of the laser beam waist diameter and the opening angle $2\theta$ of the laser beam, to the outside of the mirrors 1 and 2 in the laser resonator when the laser light 7 has more than a predetermined power. The laser beam 70 from the laser resonator is transmitted to the focussing lens 8. The laser beam passed through the focussing lens 8 is focussed to the laser beam whose diameter is $\phi_{in}$ having a range of $0.5\phi_s$ to $2\phi_s$ by the focussing lens 8 and irradiated onto the incident side plane of the optical fiber 9.

The optical fiber holder movable device 105 and the optical fiber holder 101 move the position of the incident side plane of the optical fiber 9 based on the relationship between a predetermined shift-value and the focusability of the outgoing laser beam in accordance with the value set by the focusability setting system 18 so that the solid state laser device provides the laser beam having the focusability specified by the focusability setting system 18 through the optical fiber 9. The laser beam obtained is further focussed by the focussing lens 23. The target work is processed by using the focussed laser beam.

In the laser processing device 2800 of the embodiment 28, the focusability of the laser beam may be changed easily to a laser beam having another focusability level, so that it may be applicable to various types of processing such as a highly precision processing, a wide area processing in welding, cutting and the like.

In addition, in the laser processing device 2800 of the embodiment 28, the solid state laser device 2200 of the embodiment 22 shown in FIG. 25 is used, but the scope of the present invention is not limited by this, it may be acceptable and it may get the same effect by incorporating the optical transmission devices 1500 and 1600 of the embodiments 15 and 16 as shown in FIGS. 17 and 19.

EMBODIMENT 29

FIG. 33 is a configuration diagram showing a configuration of a laser processing device 2900 of the embodiment 29 according to the present invention.

In the laser processing device 2900 shown in FIG. 33, components which are the same components used in the optical transmission device 100 of the embodiment 1 shown in FIG. 1 in configuration and function are referenced with the same reference numbers and the explanations for them are omitted here.

In the laser processing device 2900 of the embodiment 29, the laser beam having the diameter $\phi_0$ of the laser beam waist diameter and the opening angle $2\theta$ from the laser oscillator 10 is focussed to the laser beam whose diameter is $\phi_{in}$ having a range of $0.5\phi_s$ to $2\phi_s$ by the focussing lens 8 and irradiated onto the incident side plane of the optical fiber 9.

In the laser processing device 2900 of the embodiment 29, the outgoing laser beam is directly irradiated onto a target work for processing without further focussing it. Because the laser beam is transmitted through the optical fiber 9 to the target work while keeping the focusability of the laser beam, the opening angle of the outgoing laser beam from the optical fiber is relatively smaller than that of conventional laser processing devices, and it can be performed without any focussing lens in order to process a laser processing operation for a wide area, for example, for a laser hardening, with the very simple configuration shown in FIG. 33.

In the laser processing device 2900 of the embodiment 29, the optical transmission device 100 of the embodiment 1 shown in FIG. 1 is used, but the scope of the present invention is not limited by this, it may be acceptable and it may get the same effect by incorporating the optical transmission devices 200 and 1600 of the embodiments 2 and 16 as shown in FIGS. 4 and 19. In a case that the optical transmission device 200 of the embodiment 2 shown in FIG. 4 is used, the laser beam 70 having the opening angle $2\theta$ is focussed to the laser beam whose diameter is $\phi_{in}$ having a range of $0.5\phi_s$ to $2\phi_s$ by the focussing lens 8 and the aperture 11 and irradiated onto the incident side plane of the optical fiber 9. Then, the laser beam is transmitted through the optical fiber 9 while keeping the focusability of it, and provided from the optical fiber outgoing side to the target work.

EMBODIMENT 30

FIG. 34 is a configuration diagram showing a configuration of a laser processing device 3000 of the embodiment 30 according to the present invention.

In the laser processing device 3000 shown in FIG. 34, components which are the same components used in the optical transmission device 1700 of the embodiment 17 shown in FIG. 20 in configuration and function are referenced with the same reference numbers and the explanations for them are omitted here.

In the laser processing device 3000 of the embodiment 30, the light source 4 and the solid state element 3 are placed in the focussing device 6 whose internal surface is coated with a reflection material such as a white ceramic. When the electric power source 5 is turned on, the light from the light source 4 is directly irradiated to the solid state element 3 or is reflected by the focussing device 6 and then the reflected light is irradiated to the solid state element 3. A part of the light irradiated into the solid state element 3 is absorbed into the solid state element 3 itself. The absorbed light in the solid state element 3 excites the solid state element 3 so that the solid state element 3 is changed to a laser medium. Spontaneous emission light generated in the laser medium is amplified between the mirror 1 and the output mirror 2 while transferring the spontaneous emission light between the mirror 1 and the output mirror 2, and then the amplified spontaneous laser light is changed to the laser light 7. The laser light 7 is emitted, as the laser beam 70 having the diameter $\phi_0$ of the diameter of the laser beam waist and the opening angle $2\theta$ of the laser beam, to the outside of the mirrors 1 and 2 in the laser resonator when the laser light 7 has more than a predetermined power. The laser beam 70 from the laser resonator is transmitted to the focussing lens 8. The laser beam 70 from the laser resonator is transmitted to the focussing lens 8. The laser beam passed through the focussing lens 8 is focussed to the laser beam whose diameter is $\phi_{in}$ having a range of $0.5\phi_s$ to $2\phi_s$ by the focussing lens 8 and irradiated onto the incident side plane of the optical fiber 9. Then, the laser beam 70 is passed through the optical fiber 9 while keeping the focusability of the laser beam. The laser beam is provided from the outgoing side of the optical fiber 9, and the outgoing laser beam is directly irradiated onto a target work for processing without any focussing.

In the laser processing device 3000 of the embodiment 30, like the laser processing device 2900 of the embodiment 29, the opening angle of the outgoing laser beam from the optical fiber is relatively smaller than conventional laser processing devices, for example, it can be performed in order to process a laser processing operation for a wide area, for example, for a laser hardening, with the very simple configuration shown in FIG. 34, because the laser beam transmission can be performed while keeping the focusability of the laser beam.

In the laser processing device 3000 of the embodiment 34, the solid state laser device 1700 of the embodiment 17 shown in FIG. 20 is used for the explanation, but the scope of the present invention is not limited by this, it may be acceptable and it may get the same effect by incorporating the solid state laser devices 1800 and 2200 of the embodiments 18 and 22 as shown in FIGS. 21 and 25.

As described above in detail, in the optical transmission device of the present invention, the optical fiber comprises a graded index optical fiber having a diameter $\phi_c$ of a core of the optical fiber, a refraction index $n_0$ at a center of the core of the optical fiber, and a difference $\Delta n$ between refraction indexes of the center of the core and a peripheral section of the core of the optical fiber. By the optical fiber incident optical system, the laser beam has the smallest focussed point at an incident side plane in the optical fiber through which the laser beam is introduced into the optical fiber or near the incident side plane of the optical fiber, and a diameter $\phi_{in}$ of the laser beam at the incident side plane of the optical fiber having a following relationship:

$$0.5\phi_s \leq \phi_{in} \leq 2\phi s.$$

and $$\phi_s = (\phi_c \phi_0 \theta (2n_0 \Delta n)^{-\frac{1}{2}})^{1/2},$$

where, the diameter of the laser beam waist of the laser beam is $\phi_0$, and an opening angle of the laser beam is $2\theta$.

Accordingly, the laser beam generated in the laser resonator or the laser oscillator can be provided from the outgoing side of the optical fiber while keeping the highly focusability of the laser beam.

In addition, in the optical transmission device of the present invention, when the laser beam is a multi mode laser beam, the same effect can be obtained even if a high power laser beam is used.

Moreover, in the optical transmission device of the present invention, because the value $\pi\theta\phi_0/\lambda$ is not more than 100 when a wavelength of the laser beam is $\lambda$, the laser beam having the highly focusability can be provided while keeping the highly focusability.

Furthermore, the optical transmission device of the present invention further comprises an aperture which is placed near the incident side plane of the optical fiber in order to prevent irradiation of the laser beam to a peripheral section near the incident side of the optical fiber.

In addition, the optical transmission device of the present invention further comprises an aperture which is placed near the outgoing side plane of the optical fiber in order to prevent the irradiation of a reflected laser beam to a clad and the like in the optical fiber. Thereby, an adversely effect caused by the reflected laser beam can be reduced to a minimum value.

Moreover, in the optical transmission device of the present invention, the optical fiber incident system further comprises focussing lenses comprising two focussing lenses or a pair of focussing lenses. Accordingly, the laser beam diameter at the incident side plane of the optical fiber may be easily changed and adjusted based on the feature of the laser beam by adjusting a position of the two focussing lenses or the pair of focussing lenses.

In the optical transmission device of the present invention, because a graded index lens is used as one of the focussing lenses and placed near the incident side of the optical fiber or connected to said optical fiber, the laser beam diameter at the incident side plane of the optical fiber may be adjusted and changed corresponding to the feature of the laser beam by changing slightly the position of the graded index optical fiber.

Moreover, because the optical transmission device of the present invention, further comprises an aperture placed near an incident side plane of said graded index lens, the aperture placed near the graded index lens prevents to irradiate unnecessary laser beam onto the graded index lens and a peripheral section of the incident side of the optical fiber.

In addition, because the optical transmission device of the present invention further comprises an incident laser beam monitor device for measuring a magnitude of an incident laser beam at the incident side plane of the optical fiber and a movable device, the position of the focussing lens may be adjusted and changed to a most suitable position, and the most suitable focussing of the laser beam can be performed automatically.

In addition, because the optical transmission device of the present invention further comprises an incident laser beam monitor device for measuring a magnitude of an outgoing laser beam at the outgoing side of the optical fiber and a movable device, the position of the focussing lens may be adjusted and changed to a most suitable position, and the most suitable focussing of the laser beam can be performed automatically.

In the optical transmission device of the present invention, the outgoing laser beam monitor device placed at the outgoing side of the optical fiber comprises a power sensor, an aperture is placed near the incident side of the optical fiber, and a position of the optical fiber incident system is adjusted so that the output of the laser beam detected by the power sensor becomes the maximum value. Therefore a laser beam having the most suitable focusability can be obtained with a very simple configuration.

In addition, the optical transmission device of the present invention, the outgoing laser beam monitor device comprises a photo diode which is placed at a point which is shifted from an optical axis of said outgoing side plane of the optical fiber. Accordingly, the laser beam having the most suitable focusability can be obtained automatically.

Moreover, in the optical transmission device of the present invention, the outgoing laser beam monitor device comprises an aperture which is placed at the outgoing side of the optical fiber and a power sensor for detecting the laser beam which is passed through the aperture. Accordingly, the laser beam having the most suitable focusability can be obtained automatically with a very simple configuration. Further, the optical transmission device has the effect that the focusability of the outgoing laser beam can be always monitored.

Furthermore, the optical transmission device of the present invention further comprises the movable means for moving both of or one of the focussing lens and the optical fiber in order to adjust the position relationship between them, the present invention can provide the laser beam having any degree of focusability of the laser beam.

Moreover, the solid state laser device of the present invention, comprising the solid state element as the laser beam medium, the laser resonator, and the optical transmission device. In the laser resonator, the image transfer optical system comprising the mirror, the focussing lens, and the movable devices for moving the mirror and the focussing lens are incorporated. Accordingly, the laser beam having the highly focusability can be oscillated by the image transfer optical system, and at the same time, the diameter of the laser beam at the incident side of the optical fiber can be adjusted over the range of $0.5\phi_s$ to $2\phi_s$.

In addition, the solid state laser device of the present invention comprises the monitor device for detecting the outgoing laser beam from the optical fiber. Accordingly, the adjustment of the resonator can be performed automatically for transmitting the laser beam while keeping the highly focusability.

Furthermore, in the solid state laser device of the present invention, the laser resonator comprises the aperture and the adjustment means for changing the opening diameter of the aperture. Accordingly, without adjusting the laser optical system, the laser beam having any output power level can be provided while keeping the focusability of the laser beam.

In addition, in the solid state laser device of the present invention, the laser resonator comprises the aperture and movable means for moving the aperture toward an optical axis of the laser resonator. Accordingly, without adjusting the laser beam optical system, the output from the laser beam resonant may be controlled by moving the position of the aperture placed in order to transmit all types of laser beams through the optical fiber while keeping the high quality characteristics.

Furthermore, in the solid state laser device of the present invention, the laser beam from the symmetric type laser resonator is focussed into the laser beam having the smallest focussed point near the incident side plane of the optical fiber and the diameter of the laser beam having the range of $0.5\phi_s$ to $2\phi_s$. Accordingly, the solid state laser device can provide the laser beam in which the change of the focusability is small even if the output of the laser beam is changed.

Moreover, in the solid state laser device of the present invention, the solid state element comprises the slab laser medium. The components of the laser beam 70 from the laser resonator are focussed in the X axis direction and the Y axis direction, independently. Each of the components in the X axis direction and the Y axis direction has the smallest focussed point near the incident side plane of the optical fiber and whose diameter is over the range $0.5(\phi_c\phi_{0x}\phi_x(2n_0\Delta n)^{-1/2})^{1/2}$ to $2(\phi_c\phi_{0x}\phi_x(2n_0\Delta n)^{-1/2})^{1/2}$ and $0.5(\phi_c\phi_{0x}\phi_x(2n_0\Delta n)^{-1/2})^{1/2}$ to $2(\phi_c\phi_{0x}\phi_x(2n_0\Delta n)^{-1/2})^{1/2}$, respectively. Accordingly, even if the laser resonator generating the laser beam having the different focusability in the X axis direction and the Y axis direction is used, the solid state laser device can provide the laser beam without any change of the focusability while propagation of the laser beam.

Moreover, in the solid state laser device of the present invention, the solid state element comprises the slab laser medium. The component of the laser beam 70 having the highly focusability in one direction is focussed into the laser beam having the smallest focussed point near the incident side plane of the optical fiber and the diameter of the range $0.5(\phi_c\phi_0\theta(2n_0\Delta n)^{-1/2})^{1/2}$ to $2(\phi_c\phi_0\theta(2n_0\Delta n)^{-1/2})^{1/2}$. Accordingly, even if the laser resonator generating the laser beam having the different focusability in the X axis direction and the Y axis direction is used, the solid state laser device can provide the laser beam without any change of the focusability while propagation of the laser beam with a very simple configuration.

In addition, in the laser beam processing device of the present invention, the laser beam from the optical transmission device or the solid state laser device of the present invention is focussed by the focussing optical system and then irradiate it to a target work after further focussing the outgoing laser beam from the optical fiber in the laser processing operation. Accordingly, because the laser beam is passed through the optical fiber while keeping the focusability of the laser beam, it can be performed to process the target work in simple and highly accuracy by the laser beam processing device.

Moreover, in the laser beam processing device of the present invention, the laser beam from the optical transmission device or the solid state laser device of the present invention is focussed by the focussing optical system and then irradiate directly it to a target work in the laser processing operation. Accordingly, because the laser beam is passed through the optical fiber while keeping the focusability of the laser beam, it can be performed to process the target work, for example in a hardening process, in simple and highly accuracy by the laser beam processing device.

What is claimed is:

1. An optical transmission device for transmitting a laser beam, comprising:
   a optical fiber comprising an graded index optical fiber having a diameter $\phi_c$ of a core of said optical fiber, a refraction index $n_0$ at a center of said core of said optical fiber, and a difference $\Delta n$ between refraction indexes of the center of said core of said optical fiber and a peripheral section of said core of said optical fiber; and
   an optical fiber incident system having a smallest focussed point at an incident side plane in said optical fiber through which the laser beam being introduced into said optical fiber or near said incident side plane of said optical fiber, and a diameter $\phi_{in}$ of the laser beam at said incident side plane of said optical fiber having a following relationship:

$$0.5\phi_s \leq \phi_{in} \leq 2.\phi_s,$$

and $$\phi_s = (\phi_c\phi_0\theta(2n_0\Delta n)^{-1/2})^{1/2},$$

where a diameter of the laser beam waist of the laser beam is $\theta_0$, and an opening angle of the laser beam is $2\theta$.

2. An optical transmission device as claimed in claim 1, wherein the laser beam is a multi-mode laser beam.

3. An optical transmission device as claimed in claim 1, wherein the value $\pi\theta\phi_0/\lambda$ is not more than 100 when a wavelength of the laser beam is $\lambda$.

4. An optical transmission device as claimed in claim 2, wherein the value $\pi\theta\phi_0/\lambda$ is not more than 100 when a wavelength of the laser beam is $\lambda$.

5. An optical transmission device as claimed in claim 1, further comprising an aperture which is placed near said incident side plane of said optical fiber, and a diameter of which is smaller than the diameter $\phi_c$ of said core of said optical fiber and greater than said value $\phi_s$.

6. An optical transmission device as claimed in claim 2, further comprising an aperture which is placed near said incident side plane of said optical fiber, and a diameter of which is smaller than the diameter $\phi_c$ of said core of said optical fiber and greater than said value $\phi_s$.

7. An optical transmission device as claimed in claim 3, further comprising an aperture which is placed near said incident side plane of said optical fiber, and a diameter of which is smaller than the diameter $\phi_c$ of said core of said optical fiber and greater than said value $\phi_s$.

8. An optical transmission device as claimed in claim 1, further comprising an aperture which is placed near an outgoing side plane of said optical fiber through which the laser beam is outgoing, and a diameter of which is smaller than the diameter $\phi_c$ of said core of said optical fiber and greater than said value $\phi_s$.

9. An optical transmission device as claimed in claim 2, further comprising an aperture which is placed near an outgoing side plane of said optical fiber through which the laser beam is outgoing, and a diameter of which is smaller than the diameter $\phi_c$ of said core of said optical fiber and greater than said value $\phi_s$.

10. An optical transmission device as claimed in claim 3, further comprising an aperture which is placed near an outgoing side plane of said optical fiber through which the laser beam is outgoing, and a diameter of which is smaller than the diameter $\phi_c$ of said core of said optical fiber and greater than said value $\phi_s$.

11. An optical transmission device as claimed in claim 1, wherein said optical fiber incident system further comprising focussing lenses comprising a pair of focussing lenses.

12. An optical transmission device as claimed in claim 2, wherein said optical fiber incident system further comprises focussing lenses comprising a pair of focussing lenses.

13. An optical transmission device as claimed in claim 3, wherein said optical fiber incident system further comprises focussing lenses comprising a pair of focussing lenses.

14. An optical transmission device as claimed in claim 5, wherein said optical fiber incident system further comprises focussing lenses comprising a pair of focussing lenses.

15. An optical transmission device as claimed in claim 8, wherein said optical fiber incident system further comprises focussing lenses comprising a pair of focussing lenses.

16. An optical transmission device as claimed in claim 11, wherein said lenses placed at or near the incident side plane of said optical fiber comprises a graded index lens, and said graded index lens is placed near said optical fiber or joined to said optical fiber.

17. An optical transmission device as claimed in claim 16, further comprising an aperture which is placed near an incident side plane of said graded index lens.

18. An optical transmission device as claimed in claim 1, further comprising an incident laser beam monitor device for measuring a magnitude of an incident laser beam at said incident side plane of said optical fiber and a movable device, on which said optical fiber incident system is mounted, for moving said optical fiber incident system,
wherein a position of said optical fiber incident system is adjusted based on output transmitted from said incident beam monitor device.

19. An optical transmission device as claimed in claim 11, further comprising an incident laser beam monitor device for measuring a magnitude of an incident laser beam at said incident side plane of said optical fiber and a movable device, on which said optical fiber incident system is mounted, for moving said optical fiber incident system,
wherein a position of said optical fiber incident system is adjusted based on output transmitted from said incident beam monitor device.

20. An optical transmission device as claimed in claim 1, further comprising an outgoing laser beam monitor device for measuring a magnitude of an outgoing laser beam from an outgoing side plane of said optical fiber and a movable device, on which said optical fiber incident system is mounted, for moving said optical fiber incident system,
wherein a position of said optical fiber incident system is adjusted based on output transmitted from said incident beam monitor device.

21. An optical transmission device as claimed in claim 11, further comprising an outgoing laser beam monitor device for measuring a magnitude of an outgoing laser beam from an outgoing side plane of said optical fiber and a movable device, on which said optical fiber incident system is mounted, for moving said optical fiber incident system,
wherein a position of said optical fiber incident system is adjusted based on output transmitted from said incident beam monitor device.

22. An optical transmission device as claimed in claim 20, wherein said outgoing laser beam monitor device comprises a power sensor, an aperture is placed near said incident side plane of said optical fiber, and a position of said optical fiber incident system is adjusted so that the output of the laser beam detected by said power sensor becomes the maximum value.

23. An optical transmission device as claimed in claim 20, wherein said outgoing laser beam monitor device comprises a photo diode which is placed at a point which is shifted from an optical axis of said outgoing side plane of said optical fiber, and a position of said optical fiber incident system is adjusted so that an output from said photo diode is the maximum value.

24. An optical transmission device as claimed in claim 20, wherein said outgoing laser beam monitor device comprises an aperture which is placed at an outgoing side of said optical fiber and a power sensor for detecting a laser beam which is transmitted through said aperture, and a position of said optical fiber incident system is adjusted so that a power of the laser beam through said aperture becomes the maximum power.

25. An optical transmission device comprising an optical fiber incident system comprising:
a laser emitting device for emitting a laser beam;
an optical fiber incident system comprising:
a focusing lens for focussing the laser beam emitted from said laser emitting device, and
optical fiber through which the laser beam is transmitted,
wherein said optical fiber incident system focuses the laser beam concentrated by said focussing lens at an incident side plane of said optical fiber, and
said optical fiber comprises a graded index optical fiber; and
said optical transmission device further comprises:
moving means for selectively moving both of or one of said optical fiber incident system and said optical fiber,
wherein a focus of the laser beam is adjusted by selectively moving both of or one of said optical fiber incident system and said optical fiber using said moving means.

26. A solid state laser device comprising:
said optical transmission device as claimed in claim 1;
a solid state element for changing into a laser medium when said solid state element is excited by a light from a light source and for emitting a light;
a laser resonator for generating a laser beam by using the light generated in said laser medium;
an image transfer optical system comprising: a mirror and a focussing lens which is placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

27. A solid state laser device comprising:

said optical transmission device as claimed in claim 11;

a solid state element for changing into a laser medium when said solid state element is excited by a light from a light source and for emitting a light;

a laser resonator for generating a laser beam by using the light generated in said laser medium;

an image transfer optical system comprising: a mirror and a focussing lens which being placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

28. A solid state laser device comprising:

said optical transmission device as claimed in claim 18;

a solid state element for changing into a laser medium when said solid state element is excited by a light from a light source and for emitting a light;

a laser resonator for generating a laser beam by using the light generated in said laser medium;

an image transfer optical system comprising: a mirror and a focussing lens which is placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

29. A solid state laser device comprising:

said optical transmission device as claimed in claim 20;

a solid state element for changing into a laser medium when said solid state element is excited by a light from a light source and for emitting a light;

a laser resonator for generating a laser beam by using the light generated in said laser medium;

an image transfer optical system comprising: a mirror and a focussing lens which being placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

30. A solid state laser device comprising:

said optical transmission device as claimed in claim 25;

a solid state element operating as a laser medium when said solid state element is excited by a light from a light source and for emitting a light;

a laser resonator for generating a laser beam by using the light generated in said laser medium;

an image transfer optical system comprising: a mirror and a focussing lens which is placed in said laser resonator; and movable means for moving said mirror and said focussing lens toward an optical axis direction of said laser resonator, wherein a magnitude of a laser beam diameter at said incident side plane of said optical fiber is adjusted by moving a position of both of or one of said mirror and said focussing lens.

31. A solid state laser device as claimed in claim 27, further comprising an outgoing laser beam monitor device for measuring a magnitude of said outgoing laser beam from said optical fiber, wherein both of or one of said mirror and said focussing lens are moved based on an output from said outgoing laser beam monitor device.

32. A solid state laser device comprising:

said optical transmission device as claimed in claim 1;

a solid state element for changing into a laser medium when said solid state element being excited by a light from a light source and for emitting a light;

a laser resonator for generating a laser beam by using the light generated in said laser medium;

an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source for exciting the solid state element.

33. A solid state laser device comprising:

said optical transmission device as claimed in claim 11;

a solid state element for changing into a laser medium when said solid state element is excited by a light from a light source and for emitting a light;

a laser resonator for generating a laser beam by using the light generated in said laser medium;

an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source for exciting the solid state element.

34. A solid state laser device comprising:

said optical transmission device as claimed in claim 18;

a solid state element for changing into a laser medium when said solid state element is excited by a light from a light source and for emitting a light;

a laser resonator for generating a laser beam by using the light generated in said laser medium;

an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source for exciting the solid state element.

35. A solid state laser device comprising:

said optical transmission device as claimed in claim 20;

a solid state element for changing into a laser medium when said solid state element is excited by a light from a light source and for emitting a light;

a laser resonator for generating a laser beam by using the light generated in said laser medium;

an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source for exciting the solid state element.

36. A solid state laser device comprising:

said optical transmission device as claimed in claim 25;

a solid state element operating as a laser medium when said solid state element is excited by light from a light source and emitting light;

a laser resonator for generating a laser beam by using the light generated in said laser medium;

an aperture placed in said laser resonator; and adjustment means for adjusting a value of an opening diameter of said aperture, wherein a laser power of said laser beam is changed by changing the value of the opening diameter of said aperture while keeping a constant magnitude of the light from said light source.

37. A solid state laser device comprising:

said optical transmission device as claimed in claim 1;

a solid state element for changing into a laser medium when said solid state element is excited by a light from a light source and for emitting a light;

a laser resonator for generating a laser beam by using the light generated in said laser medium;

an aperture placed in said laser resonator; and movable means for moving said aperture toward an optical axis of said laser resonator, wherein a laser power of said laser beam is adjusted by moving a position of said aperture by said movable means while keeping a constant magnitude of the light from said light source for exciting the solid state element.

38. A solid state laser device comprising:

said optical transmission device as claimed in claim 11;

a solid state element for changing into a laser medium when said solid state element is excited by a light from a light source and for emitting a light;

a laser resonator for generating a laser beam by using the light generated in said laser medium;

an aperture placed in said laser resonator; and movable means for moving said aperture toward an optical axis of said laser resonator, wherein a laser power of said laser beam is adjusted by moving a position of said aperture by said movable means while keeping a constant magnitude of the light from said light source for exciting the solid state element.

39. A solid state laser device comprising:

said optical transmission device as claimed in claim 18;

a solid state element for changing into a laser medium when said solid state element is excited by a light from a light source and for emitting a light;

a laser resonator for generating a laser beam by using the light generated in said laser medium;

an aperture placed in said laser resonator; and movable means for moving said aperture toward an optical axis of said laser resonator, wherein a laser power of said laser beam is adjusted by moving a position of said aperture by said movable means while keeping a constant magnitude of the light from said light source for exciting the solid state element.

40. A solid state laser device comprising:

said optical transmission device as claimed in claim 20;

a solid state element for changing into a laser medium when said solid state element is excited by a light from a light source and for emitting a light;

a laser resonator for generating a laser beam by using the light generated in said laser medium;

an aperture placed in said laser resonator; and movable means for moving said aperture toward an optical axis of said laser resonator, wherein a laser power of said laser beam is adjusted by moving a position of said aperture by said movable means while keeping a constant magnitude of the light from said light source for exciting the solid state element.

41. A solid state laser device comprising:

said optical transmission device as claimed in claim 25;

a solid state element operating as a laser medium when said solid state element is excited by light from a light source and for emitting light;

a laser resonator for generating a laser beam using the light generated in said laser medium;

an aperture placed in said laser resonator; and movable means for moving said aperture along an optical axis of said laser resonator, wherein a laser power of said laser beam is adjusted by moving a position of said aperture using said movable means while keeping a constant magnitude of the light from said light source.

42. A solid state laser device comprising:

a solid state element for changing into a laser medium when said solid state element is excited by a light from a light source and for emitting a light;

a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index $n_0$ at a center of said core of said optical fiber, and a difference $\Delta n$ between refraction indexes of the center of said core of said optical fiber and a peripheral section of said core of said optical fiber;

said laser resonator comprises a total internal reflection lens and an output mirror whose curvature are same values, said solid state element is placed near an intermediate point between said total internal reflection mirror and said output mirror, and said total internal reflection mirror is faced to said output mirror as a symmetric resonator, and said solid state laser device further comprises:

an optical fiber incident system having a smallest focussed point at an incident side plane in said optical fiber through which the laser beam being introduced into said optical fiber or near said incident side plane of said optical fiber, and a diameter $\phi_{in}$ of the laser beam at said incident side plane of said optical fiber having a following relationship:

$$0.5\phi_s \leq \phi_{in} \leq 2_s,$$

and $$\phi_s = (\phi_c \phi_0 \theta (2n_0 \Delta n)^{-1/2})^{1/2},$$

where a diameter of the laser beam waist of the laser beam at an output level is $\phi_0$, and an opening angle of the laser beam is $2\theta$.

43. A solid state laser device comprising:

a solid state element for changing into a laser medium when said solid state element is excited by a light from a light source and for emitting a light;

a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index $n_0$ at a center of said core of said optical fiber, and a difference $\Delta n$ between refraction indexes of the center of said core of said optical fiber and a peripheral section of said core of said optical fiber;

the laser beam generated by said solid state resonator has an anisotropic characteristic in which focussing characteristics of the laser beam are different in a first direction (X axis direction) and a second direction (Y axis direction), and said solid state laser device further comprises:

an optical fiber incident system has smallest focussed points in the X axis direction and the Y axis direction at an incident side plane in said optical fiber through which the laser beam being introduced into said optical fiber or near said incident side plane of said optical fiber, and diameters $\phi_{inx}$, $\phi_{iny}$ of the laser beam in the X axis direction and the Y axis direction at said incident side plane of said optical fiber has a following relationship:

$$0.5\phi_{sx} \leq \phi_{inx} \leq 2\phi_{sx},$$

$$0.5\phi_{sy} \leq \phi_{iny} \leq 2\phi_{sy},$$

$$\phi_{sx}=(\phi_c\phi_{0x}\theta_x(2n_0\Delta n)^{-1/2})^{1/2},$$

and $$\phi_{sy}=(\phi_c\phi_{0y}\theta_y(2n_0\Delta n)^{-1/2})^{1/2},$$

where diameters of the laser beam waist of the laser beam in the X axis direction and the Y axis direction at an output level are $\phi_{0x}$ and $\phi_{0y}$, and opening angles of the laser beam in the X axis direction and the Y axis direction are $2\theta_x$ and $2\theta_y$, respectively.

44. A solid state laser device comprising:

a solid state element for changing into a laser medium when said solid state element is excited by a light from a light source and for emitting a light;

a laser resonator for generating a laser beam by using the light generated in said laser medium; and an optical transmission device comprising an optical fiber through which the laser beam is transmitted, wherein said optical fiber comprises a graded index optical fiber having a diameter $\phi_c$ of a core of said optical fiber, a refraction index $n_0$ at a center of said core of said optical fiber, and a difference $\Delta n$ between refraction indexes of the center of said core of said optical fiber and a peripheral section of said core of said optical fiber;

the laser beam generated by said solid state resonator has an anisotropic characteristic in which focussing characteristics of the laser beam are different in a first direction (X axis direction) and a second direction (Y axis direction), and said solid state laser device further comprises:

an optical fiber incident system has a smallest focussed point at the incident side plane in said optical fiber through which the laser beam being introduced into said optical fiber or near said incident side plane of said optical fiber, and a diameters $\phi_{in}$ having the largest value in $\phi_{0x}\theta_x$ of the X axis direction and $\phi_{0y}\theta_y$ in the Y axis direction at said incident side plane of said optical fiber has a following relationship:

$$0.5\phi_s \leq \phi_{in} \leq 2_s,$$

$$\phi_s=(\phi_c\phi_0\theta(2n_0\Delta n)^{-1/2})^{1/2},$$

and $$\phi_0\theta=\max(\phi_{0x}\theta_x, \phi_{0y}\theta_y),$$

where diameters of the laser beam waist of the laser beam in the X axis direction and the Y axis direction at an output level are $\phi_{0x}$ and $\phi_{0y}$, and opening angles of the laser beam in the X axis direction and the Y axis direction are $2\theta_x$ and $2\theta_y$, respectively.

45. A laser processing device for processing a target work, comprising:

said optical transmission device as claimed in claim 1; and a focussing optical system for focussing the laser beam transmitted from said optical transmission device and for irradiating a focussed laser beam to said target work.

46. A laser processing device for processing a target work, comprising:

said solid state laser device as claimed in claim 26; and a focussing optical system for focussing the laser beam transmitted from said solid state laser device and for irradiating a focussed laser beam to said target work.

47. A laser processing device for processing a target work, comprising:

said optical transmission device as claimed in claim 1, wherein an outgoing laser beam from said optical transmission device is directly irradiated to said target work for processing said target work.

48. A laser processing device for processing a target work, comprising:

said solid state laser device as claimed in claim 26, wherein an outgoing laser beam from said solid state laser device is directly irradiated to said target work for processing said target work.

* * * * *